United States Patent [19]

Ajito et al.

[11] Patent Number: 5,602,106
[45] Date of Patent: Feb. 11, 1997

[54] 16-MEMBERED MACROLIDE DERIVATIVES

[75] Inventors: Keiichi Ajito; Osamu Hara; Ken-ichi Kurihara; Nobue Kikuchi; Minako Araake; Akira Shimizu; Tsuneo Okonogi; Shigeharu Inouye; Seiji Shibahara, all of Kanagawa, Japan

[73] Assignee: Meiji Seika Kaisha, Ltd., Tokyo, Japan

[21] Appl. No.: 271,996

[22] Filed: Jul. 8, 1994

[30] Foreign Application Priority Data

| Jul. 8, 1993 | [JP] | Japan | 5-169418 |
| Nov. 30, 1993 | [JP] | Japan | 5-300686 |
| May 19, 1994 | [JP] | Japan | 6-105096 |
| Jun. 8, 1994 | [JP] | Japan | 6-126654 |
| Jun. 27, 1994 | [JP] | Japan | 6-145125 |

[51] Int. Cl.$^6$ .................. A61K 31/70; C07H 17/08
[52] U.S. Cl. .................. 514/30; 536/7.1
[58] Field of Search .................. 536/7.1; 514/30

[56] References Cited

U.S. PATENT DOCUMENTS

| 5,032,581 | 7/1991 | Lukacs et al. | 536/7.1 |
| 5,444,174 | 8/1995 | Ajito et al. | 536/7.1 |

*Primary Examiner*—Elli Peselev
*Attorney, Agent, or Firm*—Sughrue, Mion, Zinn, Macpeak & Seas

[57] ABSTRACT

16-membered macrolide derivatives represented by the formula (I):

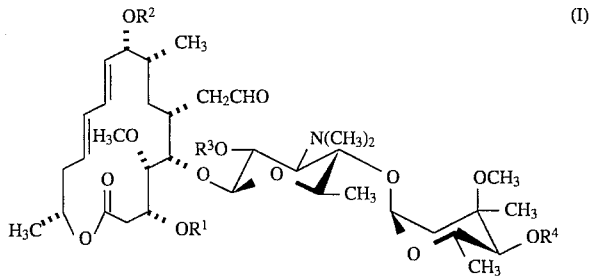

wherein $R^1$ represents a hydrogen atom or a substituent group which protects a hydroxyl group; $R^2$ represents a hydrogen atom or a substituent group which protects a hydroxyl group; $R^3$ represents a hydrogen atom or a straight-chain aliphatic acyl group having 2 to 4 carbon atoms; and $R^4$ represents a hydrogen atom or a straight-chain aliphatic or aromatic acyl group having 1 to 10 carbon atoms;

or a pharmaceutically acceptable salt thereof are disclosed.

A novel process for producing these 16-membered macrolide derivatives is also disclosed.

26 Claims, No Drawings

16-MEMBERED MACROLIDE DERIVATIVES

FIELD OF THE INVENTION

This invention relates to novel 16-membered macrolide derivatives effective on Gram-positive bacteria and other bacteria and to a novel process for producing the same.

BACKGROUND OF THE INVENTION

Macrolide antibiotics effective on, for example, Gram-positive bacteria, Mycoplasma and Chlamydia, are regarded as clinically important antimicrobial drugs since they can be orally administered and have low toxicity. In order to improve their clinical availability, research groups in various countries have been positively conducting studies on derivatives of 16-membered macrolide antibiotics. Several derivatives of 16-membered macrolides have been synthesized by acylating hydroxyl groups at specific positions for improving their antimicrobial activities in vitro and/or pharmacokinetics. Particularly, miokamycin [Journal of Antibiotics, 29(5), 536 (1976) and Japanese Journal of Antibiotics, 35(6), 1462 (1982)] has been frequently used clinically, mainly in the field of pediatrics, as a semisynthetic 16-membered macrolide antibiotic, because of its excellent pharmacokinetics and little bitterness in comparison with natural compounds. Recently, studies on the development of the derivatives have been directed mostly toward introduction of substituted amino groups into a lactone ring a 16-membered macrolide [Journal of Antibiotics, 44(4), 448 (1991)], deoxylation of specific hydroxyl groups [Journal of antibiotics, 45(1), 144 (1992)] or alkylation of hydroxyl groups which is significant in terms of pharmacokinetics. The 16-membered macrolide antibiotics are advantageous in that: (1) resistance to these antibiotics is scarcely induced; (2) they exert less interaction with other drugs; (3) they show less affect on the intestinal tract; and (4) they give little irritation at the oral administration. In view of these characteristics, the present inventors have selected 16-membered macrolide antibiotics as a research subject and have conducted studies on the screening of a compound which shows excellent effects on various Gram-positive bacteria, by means of synthetic chemical and biochemical approaches.

Firstly, the present inventors have found a synthetic process for introducing a methyl group to a tertiary hydroxyl group at the 3"-position of a 16-membered macrolide as a methodology for the improvement of its antimicrobial activity in vitro based on the chemical structure of L-chladinose which is a constituent sugar of erythromycin. Tatsuta et al. have reported the synthesis of another 16-membered macrolide having a methylated hydroxyl group at the 3"-position which has been prepared by a glycosylation method differing from the process provided by the present inventors [Chemistry Letters, 769 (1977)]. According to this report, 3"-O-methylcarbomycin B shows higher antimicrobial activity than carbomycin B against certain bacteria, for example, a species of acid-fast bacteria. The derivatives described in these reports, in which a hydroxyl group at the 3"-position is methylated, have a carbonyl group, an $sp^2$ carbon, at the 9-position. No information is available to date concerning a 16-membered macrolide derivative having an $sp^3$ carbon at the 9-position and a methylated tertiary hydroxyl group at the 3"-position.

Secondly, with regard to a microbial conversion in which a carbonyl group at the 9-position of 16-membered macrolide is reduced to a hydroxyl group having a natural configuration, its application example and efficacy obtained thereby have already reported by the present inventors (EP-A-0 595 303). In order to clarify the correlation among structures of 16-membered macrolide compounds, to study biosynthesis of these compounds and to analyze the structures thereof, there have been known methods for reducing a carbonyl group at the 9-position of a 16-membered macrolide compound into a hydroxyl group through a synthetic chemical approach [Journal of Organic Chemistry, 39(16), 2474 (1974); Journal of Antibiotics, 34(12), 1577 (1981); and ibid., 39(12), 1784 (1986)] and through a biochemical approach [JP-A-50-126880; Journal of Antibiotics, 32(7), 777 (1979); JP-A-54-8793; and Journal of Antibiotics, 33(8), 911 (1980)] (The term "JP-A" as used herein means an "unexamined published Japanese patent application").

Thirdly, with regard to a microbial conversion for specifically cleaving an acyl group binding to a hydroxyl group at the 3-position of a lactone ring of a 16-membered macrolide to form a free hydroxyl group, the present inventors have reported its details including studies on substrate specificity of the conversion reaction [EP-A-526,906 (1993), U.S. Pat. No. 5,219,736 (1993) and JP-A-6-16691]. On the other hand, similar biochemical reactions effected by *Bacillus subtilis*, or an enzyme produced thereby, have been already reported [Journal of Fermentation Technology, 57(6), 519 (1979) and JP-A-54-28892].

Fourthly, an investigation has been made on derivatives of Medemycin (midecamycin $A_1$) [Journal of Antibiotics, 24(7), 452 (1971)], a naturally occurring 16-membered macrolide antibiotic, in order to improve its in vivo effect. As a result, several excellent medemycin derivatives have been obtained, including a 16-membered macrolide derivative in which a hydroxyl group at the 3"-position in the neutral sugar moiety is converted into a methylthiomethyl ($—CH_2SCH_3$) group, which is used as a key intermediate of the present invention. A synthetic method of the derivative is reported in Journal of Antibiotics, 33(1), 61 (1980). In the field of carbohydrate chemistry, it has been known since 1960 that a methylthiomethyl group introduced into a secondary hydroxyl group is reduced to a methoxy group [Carbohydrate Research, 7, 474 (1968)].

Fifthly, the present inventors have already provided a synthetic method in which a 16-membered macrolide antibiotic having a free hydroxyl group at the 3-position of a lactone ring is used as a starting material and an alkyl group is introduced by turns into the 4"-position and 3"-position hydroxyl groups in the neutral sugar moiety (EP-A-0 595 303).

Sixthly, as to protection of a hydroxyl group at the 3-position of a lactone ring of a 16-membered macrolide derivative, there is a report on protection of a hydroxyl group at the 3-position of a lactone ring of spiramycins and tylosins with an acetal base substituent group having an asymmetric carbon atom. However, except for spiramycins, there are no synthetic intermediate compound having a platenolide skeleton (a lactone ring of leucomycin), in which a hydroxyl group at the 3-position of a lactone ring is substituted with an acetal group having an asymmetric carbon atom.

It has been reported that 16-membered macrolide antimicrobial agents cause little side effects but their antimicrobial activities in vitro are generally weak in comparison with those of 14-membered counterparts [*Antimicrobial Agents and Chemotherapy*, 32(11), 1710 (1988)]. In consequence, great concern has been directed in the first place toward the development of an excellent derivative of a 16-membered macrolide antibiotic, whose antimicrobial activities against the genus Streptococcus as one of the main causative bacteria of clinically important upper respiratory infection and *Enterococcus feacalis* as one of the causative bacteria of multiple infection with MRSA (The 461th Special Member Meeting of Japan Antibiotics Research Association, Feb. 22, 1991) are improved to the level of 14-membered new macrolides, while keeping the 16-membered macrolide's superior features to cause little side effects and drug interaction.

On the other hand, cost and time required for the production of such derivatives are not always satisfactory, because it is necessary to perform a chemical reaction consisting of a plural number of steps involving regio- and stereo-selective glycosylation for introducing a neutral sugar and two continuous steps of microbial conversion in the practice of the preparation of these derivatives. Furthermore, an activator, which is dangerous and to be handled with care, should be stoichiometrically used in the aforementioned glycosylation reaction, and there are some problems in scaling up thereof such as many days required for the production. Accordingly, it has been secondly required to establish a process for the production of a 16-membered macrolide derivative in which the 3"-position hydroxyl group in the neutral sugar moiety of the present invention is methylated, by pure chemical synthesis through less steps without using any glycosylation reaction.

SUMMARY OF THE INVENTION

An object of the present invention is to provide 16-membered macrolide derivatives which have excellent antimicrobial activities.

Another object of the present invention is to provide processes for efficiently producing these derivatives.

In order to attain the above objects, the inventors of the present invention have conducted a series of synthetic chemical and biochemical studies. Firstly, using microorganisms having various pertinent conversion functions, biochemical reactions were applied to 3"-O-methylmidecamycin $A_3$ is a 16-membered macrolide derivative having a modified constituent sugar of erythromycin, L-chladinose, linked by a glycoside bonding, and, as the result, the present inventors have succeeded in preparing various 16-membered macrolide derivatives in which the 9-position is an $sp^3$ carbon and, at the same time, a tertiary hydroxyl group at the 3"-position is methylated. Thereafter, the first aspect of the present invention was completed by finding in some of these derivatives a strong growth inhibitory activities against clinically important Gram-positive bacteria, especially the species of Streptococcus, *Enterococcus feacalis* and certain erythromycin resistant strains, similar to the case of 14-membered new macrolides.

Next, the present inventors have succeeded in establishing an efficient process for the production of one of the 16-membered macrolide derivatives prepared by the above invention, a derivative in which the 3-position hydroxyl group of a lactone ring is acylated, the 3"-position tertiary hydroxyl group in a neutral sugar moiety is methylated and the 4"-position hydroxyl group is acylated, without employing glycosylation reaction, using, as a starting material, a natural 16-membered macrolide antibiotic having an acyl group on a hydroxyl group at the 3-position of a lactone ring, and via a synthetic intermediate whose 3"-position is methylthiomethylated. Thus, the second aspect of the present invention has been accomplished. In addition, in the course of the studies on this invention, an excellent method has been found useful for the protection and deprotection of a hydroxyl group at the 9-position of a lactone ring of 16-membered macrolide derivatives.

Also, the third aspect of the present invention has been accomplished on the basis of a success in producing a leucomycin derivative in which the 3- and 9-positions of a lactone ring are both free hydroxyl groups, the 3"-position tertiary hydroxyl group in a neutral sugar moiety is methylated and the 4"-position hydroxyl group is acylated, which is also one of the 16-membered macrolide derivatives prepared by the above first invention, by a purely synthetic chemical manner and without employing glycosylation reaction, using a naturally occurring leucomycin Fr group such as leucomycin $A_5$ [*Journal of Antibiotics*, Ser.A. 20(4), 234 (1967)] as a starting material, and via a synthetic intermediate whose hydroxyl group at the 3-position of a lactone ring is protected by an acetal base substituent group having an asymmetric carbon and whose hydroxyl group at the 3"-position is methylthiomethylated.

In addition, the fourth aspect of the present invention has been accomplished on the basis of a success in developing a synthetic process for the production of the above-mentioned leucomycin derivative in which the 3- and 9-positions of a lactone ring are both free hydroxyl groups, the 3"-position tertiary hydroxyl group in a neutral sugar moiety is methylated and the 4"-position hydroxyl group is acylated, using, for example, leucomycin $A_7$ [*Journal of Antibiotics*, Ser.A. 20(4), 234 (1967)] as a starting material, and via a synthetic intermediate whose 9-, 3- and 18-positions of a lactone ring are protected by a silyl group and the like and whose hydroxyl group at the 3"-position is methylthiomethylated. This process has such a high degree of freedom that any acyl side chain of interest can be introduced into the 4"-position independent of the structure of an acyl side chain at the 4"-position neutral sugar moiety of the starting material (either natural or synthetic). In this way, studies on the screening of chladinose analog 16-membered macrolide derivatives have been completed.

The present invention mainly relates to a novel compound represented by the formula (I):

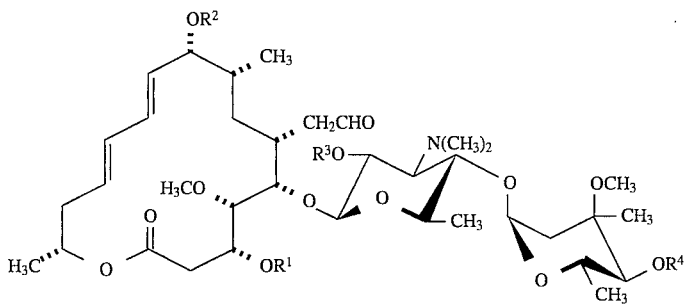

(I)

wherein $R^1$ represents a hydrogen atom or a substituent group which modifies (protects) a hydroxyl group; $R^2$ represents a hydrogen atom or a substituent group which modifies (protects) a hydroxyl group; $R^3$ represents a hydrogen atom or a straight-chain aliphatic acyl group having 2 to 4 carbon atoms; and $R^4$ represents a hydrogen atom or a straight- or branched-chain aliphatic or aromatic acyl group having 1 to 10 carbon atoms, or a pharmaceutically acceptable salt thereof and to a process for producing the same.

DETAILED DESCRIPTION OF THE INVENTION

The gist of the first aspect of the present invention resides in a compound represented by the above formula (I). In the formula (I), a substituent group which modifies (protects) a hydroxyl group represented by $R^1$ and $R^2$ is preferably an aliphatic acyl group having 2 to 4 carbon atoms. $R^1$ preferably represents a hydrogen atom, an acetyl group, a propionyl group and a 1-ethoxyethyl group. $R^2$ preferably represents a hydrogen atom, an acetyl group, a propionyl group, a butyryl group and a 1-ethoxyethyl group. $R^3$ preferably represents a hydrogen atom and an aliphatic acyl group having 2 to 3 carbon atoms such as an acetyl group and a propionyl group. $R^4$ preferably represents a hydrogen atom and an aliphatic or aromatic acyl group having 2 to 7 carbon atoms such as an acetyl group, a propionyl group, a normal butyryl group, an isobutyryl group, a normal valeryl group, an isovaleryl group and a benzoyl group.

The gist of the second aspect of the present invention resides in a novel compound represented by the formula (IX) which is one of the compounds of the formula (I):

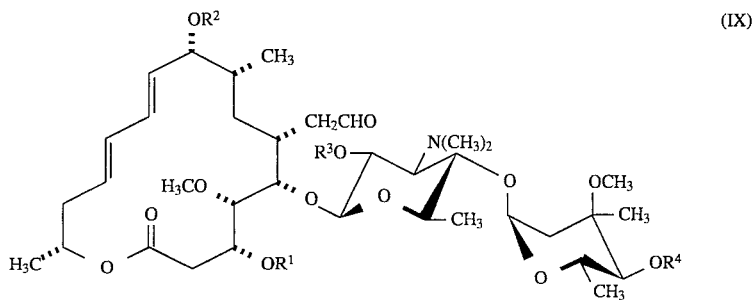

wherein $R^1$ represents a hydrogen atom or a straight-chain aliphatic acyl group having 2 to 4 carbon atoms; $R^2$ represents a hydrogen atom or a substituent group which modifies a hydroxyl group; $R^3$ represents a hydrogen atom or a straight-chain aliphatic acyl group having 2 to 4 carbon atoms; and $R^4$ represents a hydrogen atom or a straight- or branched-chain aliphatic or aromatic acyl group having 1 to 10 carbon atoms, or a pharmaceutically acceptable salt thereof.

The compound of the formula (IX) can be produced by subjecting a compound represented by the formula (X)

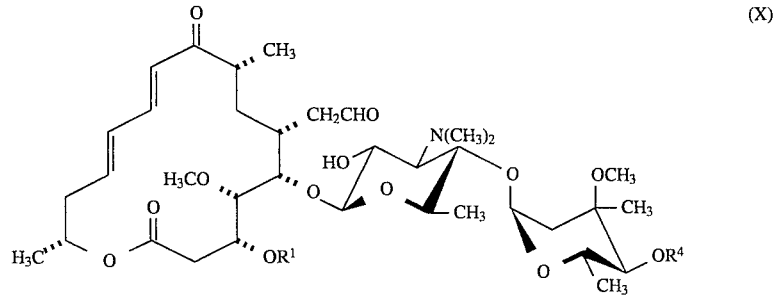

wherein $R^1$ represents a straight-chain aliphatic acyl group having 2 to 4 carbon atoms and $R^4$ represents a straight- or branched-chain aliphatic or aromatic acyl group having 1 to 10 carbon atoms or a salt thereof, to a biochemical conversion using a single microorganism or continuously using a plurality of microorganisms and, if necessary, applying a selective synthetic chemical reaction to the 9- and/or 2'-position hydroxyl group.

The compound represented by the formula (X) can be synthesized by a sugar component introducing reaction, namely glycosylation. More illustratively, it can be produced by subjecting a sugar component donor (glycosyl donor) derived from L-chladinose or the like to glycosylation using, as a sugar component acceptor (glycosyl acceptor), a protected synthetic intermediate in which D-mycaminose is linked to a hydroxyl group at the 5-position of a 16-membered lactone ring by β-glycoside bonding, followed by a synthetic chemical reaction. That is, the compound represented by the formula (X) can be produced either by a production process in which the process is effected via glycosylation and using a thio-sugar or by a known synthetic process including glycosylation using a glycal [*Chemistry Letters,* 769 (1977)]. According to the former process, it can produce 3"-O-methylmidecamycin $A_3$ (a compound of the formula (X) in which $R^1$ represents a propionyl group and $R^4$ represents a propionyl group) and the like, and the latter process can produce 3"-O-methylcarbomycin B (a compound of the formula (X) in which $R^1$ represents an acetyl group and $R^4$ represents an isovaleryl group) and the like. In addition, in either case of the production of the compound of formula (X) by these processes, any desired acyl group can be introduced into the 3-position side chain $R^1$ and the 4"-position side chain $R^4$ of the compound (X), by properly selecting respective acyl side chains at the 3-position of a sugar component acceptor and at the 4-position (4"-position after glycosylation) of a sugar component donor at the time of the glycosylation reaction (it is desirable to use a natural type acyl group with regard to the 3-position side chain $R^1$).

The following reaction scheme 1 shows an illustrative reaction path for the production of 4 compounds represented by formulae (XI) to (XIV) as principal compounds of the compound represented by the formula (IX), from the compound of formula (X) as a starting material by means of microbial conversion.

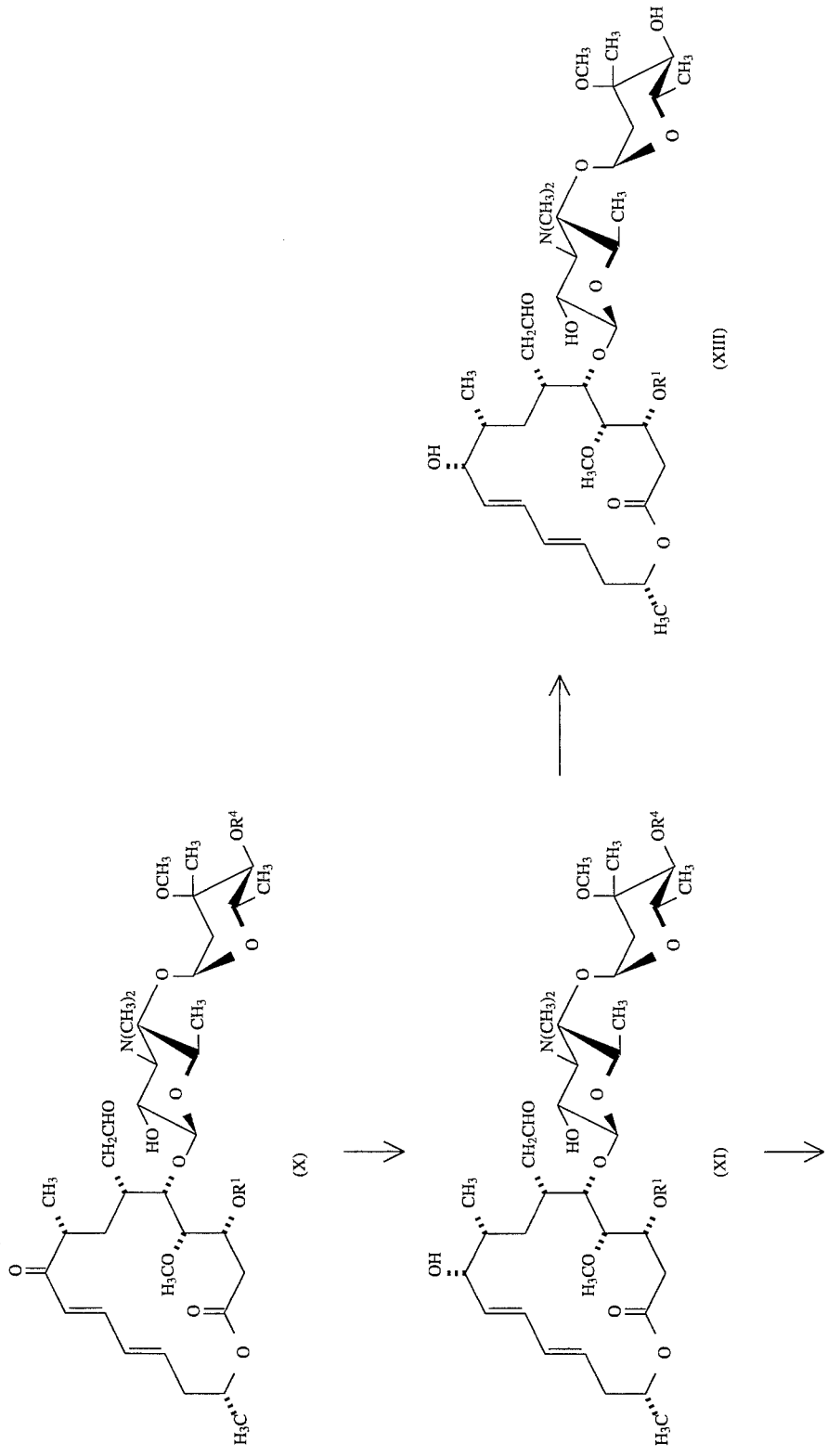

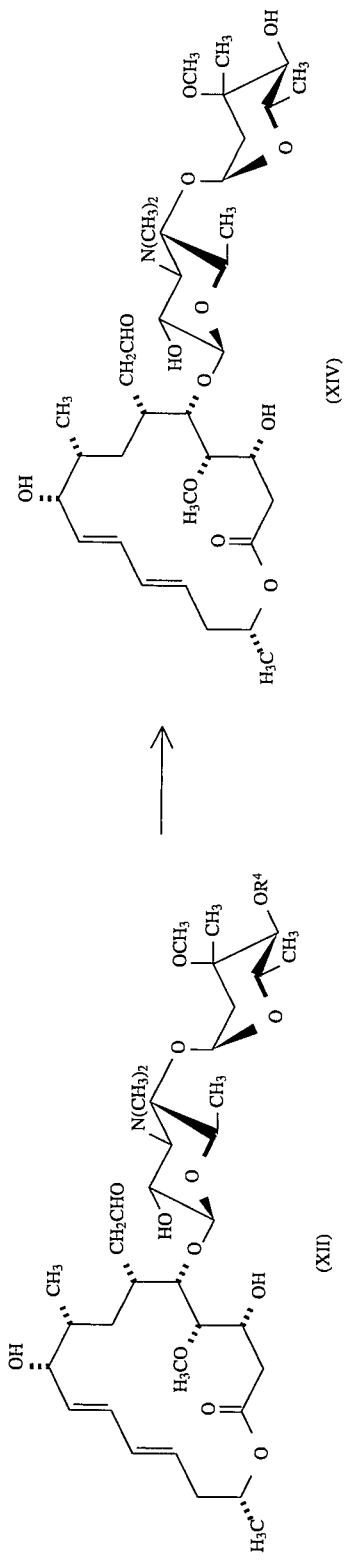

Firstly, a microbial conversion by *Streptomyces mycarofaciens* SF2772 strain, which is one of actinomycetes, disclosed by the present inventors in EP-A-0 595 303 was selected as a process for the production of a novel compound represented by the formula (XI),

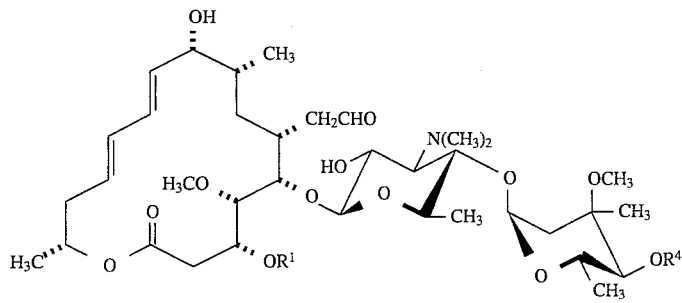

(XI)

wherein $R^1$ represents a straight-chain aliphatic acyl group having 2 to 4 carbon atoms and $R^4$ represents a straight- or branched-chain aliphatic or aromatic acyl group having 1 to 10 carbon atoms or a salt thereof, from the compound of formula (X) or a salt thereof. That is, the compound represented by formula (XI) was efficiently prepared by subjecting the compound of formula (X) to microbial conversion with the strain SF2772 to effect reduction of a carbonyl group at the 9-position of the starting material into a hydroxyl group having a natural type configuration. For example, 3"-O-methylmidecamycin $A_3$ (a compound of the formula (X) in which $R^1$ represents a propionyl group and $R^4$ represents a propionyl group) is converted into 3"-O-methylmidecamycin $A_1$ (a compound of the formula (XI) in which $R^1$ represents a propionyl group and $R^4$ represents a propionyl group) through the biochemical conversion by the strain SF2772. In this instance, the process itself for the reduction of a carbonyl group at the 9-position into a hydroxyl group by a biochemical reaction for use in the conversion of a 16-membered macrolide is a known art (cf. "Prior Art" in JP-A-54-8793 for example).

The above microbial conversion process will be described later in detail in EXAMPLES. The biochemical reaction having such a conversion function is not limited to the SF2772 microbial conversion, and not only a conversion reaction in which a microorganism other than the strain SF2772 is used but also a biochemical reaction in which a non-microbial conversion function is used may be used. *Streptomyces mycarofaciens* SF2772 has been deposited by the present inventors in National Institute of Bioscience and Human Technology, Agency of Industrial Science and Technology, since Oct. 28, 1992 under the accession number FERM BP-4465 in accordance with the Budapest treaty.

The process for the production of the novel compound represented by the formula (XI) from the compound of formula (X) is not particularly limited to a biochemical means such as a microbial conversion, a reaction using an enzyme produced by a living organism or the like, and it may be produced also by a synthetic chemical means which includes steps for the protection and deprotection of an aldehyde group at the 18-position [*Journal of Organic Chemistry*, 39(16), 2474 (1974)]. However, results of the reduction of a carbonyl group at the 9-position into a hydroxyl group having a natural type configuration by the synthetic chemical means may not always be satisfactory, taking account of stereo-selectivity of the reaction and yield of the above protection and deprotection steps (especially a step for the introduction of an acetal at the 18-position). In consequence, the inventors of the present invention have further continued preparation of new derivatives making use of reduction reaction at the 9-position by biochemical means.

Next, a process for the production of a novel compound represented by the formula (XII),

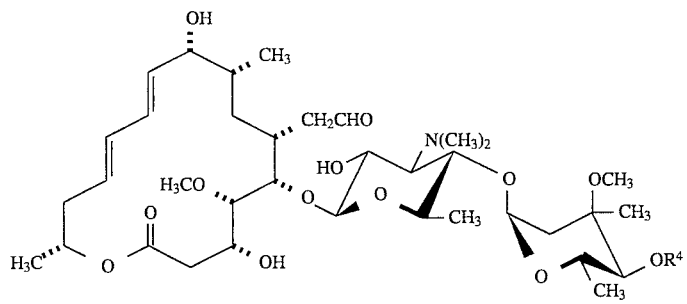

(XII)

wherein $R^4$ represents a straight- or branched-chain aliphatic or aromatic acyl group having 1 to 10 carbon atoms or a salt thereof, from the compound of formula (XI) or a salt thereof has been accomplished by carrying out a known microbial conversion process in which one of fungal strains belonging to the genus Phialophora, the strain PF1083, discovered by the present inventors [European Patent 526,906 (1993), U.S. Pat. No. 5,219,736 (1993) and JP-A-6-16691] is used. That is, the compound represented by formula (XII) was efficiently prepared by subjecting the compound of formula (XI) to a microbial conversion with the strain PF1083 to specifically cleave an acyl group linked to a hydroxyl group at the 3-position of a lactone ring of the starting material to thereby form a free hydroxyl group. For example, 3"-O-methylmidecamycin $A_1$ (a compound (1) of the formula (XI) in which $R^1$ represents a propionyl group and $R^4$ represents a propionyl group) is converted into 3"-O-methylleucomycin $A_7$ (a compound (2) of the formula (XII) in which $R^4$ represents a propionyl group) through the biochemical conversion by the strain PF1083.

The above microbial conversion process will be described later in detail in EXAMPLES. The biochemical reaction having such a conversion function is not limited to the PF1083 microbial conversion, and not only a conversion reaction in which a microorganism other than the strain PF1083 is used but also a biochemical reaction in which a non-microbial conversion function is used may be used. However, little is known about the biochemical reaction for specific cleavage of an acyl group linked to a hydroxyl group at the 3-position of a lactone ring of a 16-membered macrolide compound. Phialophora sp. PF1083 has been deposited by the present inventors in National Institute of Bioscience and Human Technology, Agency of Industrial Science and Technology, since May 28, 1991 under the accession number FERM BP-3960 in accordance with the Budapest treaty.

The process for the production of the novel compound represented by the formula (XII) from the compound of formula (XI) is not particularly limited to the biochemical means so far described, but there are no reports on the synthetic chemical means for specifically cleaving an acyl group linked to a hydroxyl group at the 3-position of a lactone ring of a 16-membered macrolide compound in a high yield, except for the deacylation in compounds having tylonolide skeletons.

Next, a novel compound represented by the formula (XIII), a neutral sugar) of each starting material to thereby form a free hydroxyl group. For example, 3"-O-methylmidecamycin $A_1$ (a compound (1) of the formula (XI) in which $R^1$ represents a propionyl group and $R^4$ represents a propionyl group) and 3"-O-methylleucomycin $A_7$ (a compound (2) of the formula (XII) in which $R^4$ represents a propionyl group) are converted respectively into 3"-O-methylmidecamycin $M_1$ (a compound (3) of the formula (XIII) in which $R^1$ represents a propionyl group) and 3"-O-methylleucomycin V (a compound (4) of the formula (XIV)) through the biochemical conversion by the strain of the genus Mucor or the like. An example of the strain is *Mucor spinescens* IAM 6071 (JP-A-48-72389). The above microbial conversion process will be described later in detail in EXAMPLES.

There are many reports on biochemical reactions for the cleavage of an acyl group linked to a hydroxyl group at the 4-position (4"-position) of a neutral sugar of a 16-membered macrolide compound [*Hakko to Kogyo*, 37(8), 1749 (1979)]. Such a conversion reaction in midecamycin $A_1$ [medemycin; *Journal of Antibiotics*, 24(7), 452 (1971)] has been studied for a long time (JP-B-48-29148), and it has been reported that considerably varied types of naturally occurring microbial species, especially fungi, are possessed of the deacylation ability.

On the other hand, nothing has been known about biochemical deacylation at the 4"-position in a 16-membered

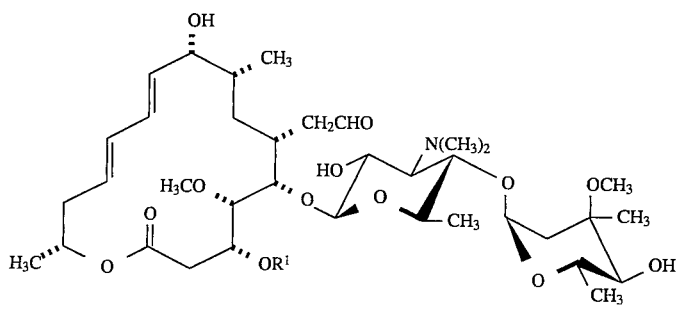

(XII)

wherein $R^1$ represents a straight-chain aliphatic acyl group having 2 to 4 carbon atoms or a salt thereof, and another novel compound represented by the formula (XIV)

macrolide derivative whose tertiary hydroxyl group at the 3"-position was methylated. Thereafter, the present inventors have confirmed that efficient progress in the desired

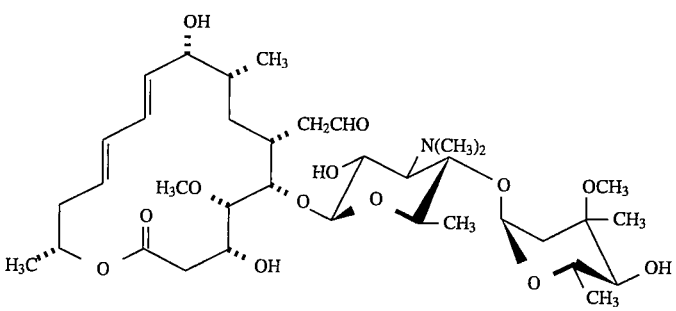

(XIV)

or a salt thereof, were produced respectively from the compound of formula (XI) or a salt thereof and the compound of formula (XII) or a salt thereof making use of a known biochemical reaction (JP-B-48-29148; the term "JP-B" as used herein means an "examined published Japanese patent application"). That is, the compounds represented by formulae (XIII) and (XIV) were efficiently prepared by respectively subjecting the compounds of formulae (XI) and (XII) to microbial conversion for example with a strain belonging to the genus Mucor of the order Mucorales, the subdivision Zygomycota to specifically cleave an acyl group linked to a hydroxyl group at the 4"-position (4-position of conversion reaction can be obtained by the use of a plurality of fungal strains. In this connection, the biochemical reaction having such a conversion function is not limited to the microbial conversion by a strain belonging to the genus Mucor or the like, and not only a conversion reaction in which a microorganism other than fungi is used but also a biochemical reaction in which a non-microbial conversion function is used may be used.

As has been described in the foregoing, the compounds represented by formulae (XI) to (XIV) or salts thereof were prepared using the compound of formula (X) or a salt thereof as a starting material in accordance with the reaction path shown in the reaction scheme 1. In this connection, when a plurality of microbial species having desired conversion functions are used in a continuous manner, order of the conversion reactions is not always limited by the reaction path shown in the reaction scheme 1 and can be set relatively freely, though there is a possibility of receiving certain restrictions such as substrate specificity and the like. For example, it is possible to produce the compound represented by formula (XIV) not only by the conversion of the compound of formula (XII) but also by using the compound of formula (XIII) as a conversion substrate.

In the aforementioned processes, the compounds represented by formulae (XI) to (XIV) were prepared efficiently by applying biochemical reactions to the compound of formula (X) using a single microorganism or by continuous use of a plurality of microorganisms. The thus obtained 16-membered macrolide derivatives in which an $sp^3$ carbon is located at the 9-position and, at the same time, a methyl group is introduced into a tertiary hydroxyl group at the 3"-position can be treated with most of the selective and non-selective synthetic chemical reactions which are applicable to usual 16-membered macrolide derivatives whose 9-position is $sp^3$ carbon (except for reactions upon the 3"-position).

For example, novel and useful substances can be created based on the present invention by selectively acylating a hydroxyl group at the 9- or 2'-position of each of the compounds represented by the formulae (XI) to (XIV) or salts thereof in accordance with a known method [*Hakko to Kogyo*, 37(12), 1171 (1979)], by subjecting the hydroxyl group at the 9-position of the compound to allylic rearrangement into the 11- or 13-position in the presence of a dilute acid in accordance with a known method [*Chemical and Pharmaceutical Bulletin*, 18(8), 1501 (1970); *Scientific Report of Meiji Seika Kaisha*, 12, 85 (1972); and *Journal of Antibiotics*, 35(11), 1521 (1982)] or by selectively oxidizing the hydroxyl group at the 9-position in accordance with a known method [*Journal of Antibiotics*, 24(8), 526 (1971)]. As an example, a compound (5) (a compound of the formula (I) in which $R^1$ is a propionyl group, $R^2$ is an acetyl group, $R^3$ is a hydrogen atom and $R^4$ is a propionyl group) and a compound (6) (a compound of the formula (I) in which $R^1$ is a hydrogen atom, $R^2$ is an acetyl group, $R^3$ is a hydrogen atom and $R^4$ is a propionyl group) are synthesized by selectively acetylating the hydroxyl group at the 9-position of lactone rings of the compounds (1) and (2) in accordance with a known method (JP-A-48-13380).

Since reduction at the 9-position, deacylation at the 3-position and deacylation at the 4"-position of 16-membered macrolide compounds by the use of microorganisms belonging to the genus Streptomyces, Phialophora or Mucor were confirmed to be useful by the present invention, various processes for the production of the inventive compounds could be designed based on these biochemical techniques. On the other hand, various other processes for the production of the inventive compounds may also be designed making use of different types of biochemical means such as direct fermentation or other types of biochemical conversion reactions which are not described in the present invention. In addition, various processes for the production of the inventive compounds (1) to (6) and the like may also be designed making use of synthetic chemical techniques. In consequence, the present invention is not restricted by these inventive examples and includes not only modifications of the examples but also all synthesis, production, extraction and purification processes which are carried out by known techniques based on the properties of the compounds (1), (2), (3), (4), (5) and (6) represented by the formula (I) of the present invention.

The gist of the third aspect of the present invention resides in a novel chemical synthetic process for efficiently producing a compound represented by the formula (III):

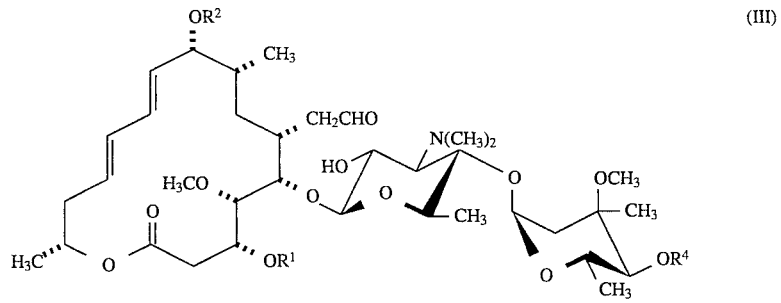

wherein $R^1$ represents a straight-chain aliphatic acyl group having 2 to 4 carbon atoms; $R^2$ represents a hydrogen atom or a substituent group which modifies (or protects) a hydroxyl group; and $R^4$ represents a straight- or branched-chain aliphatic acyl group having 2 to 5 carbon atoms, or a salt thereof, via a synthetic intermediate having methylthiomethyl ether at the 3"-position, from a compound represented by the formula (II)

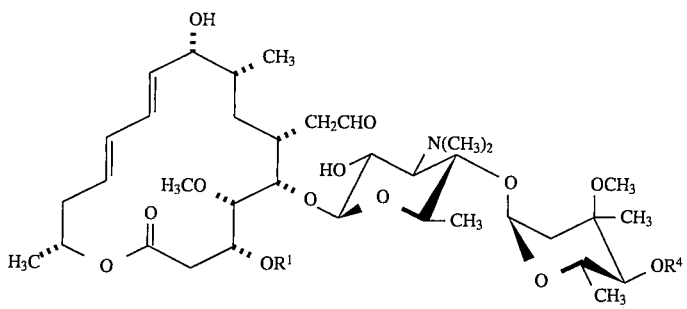
(II)

wherein $R^1$ represents a straight-chain aliphatic acyl group having 2 to 4 carbon atoms and $R^4$ represents a straight- or branched-chain aliphatic acyl group having 2 to 5 carbon atoms, or a salt thereof as a starting material. The compound of the present invention represented by the formula (III) can be produced in accordance with the procedure shown in the following reaction scheme 2 (in the reaction scheme 2, the compound of formula (III) is shown by formula (XIX) or (xx)).

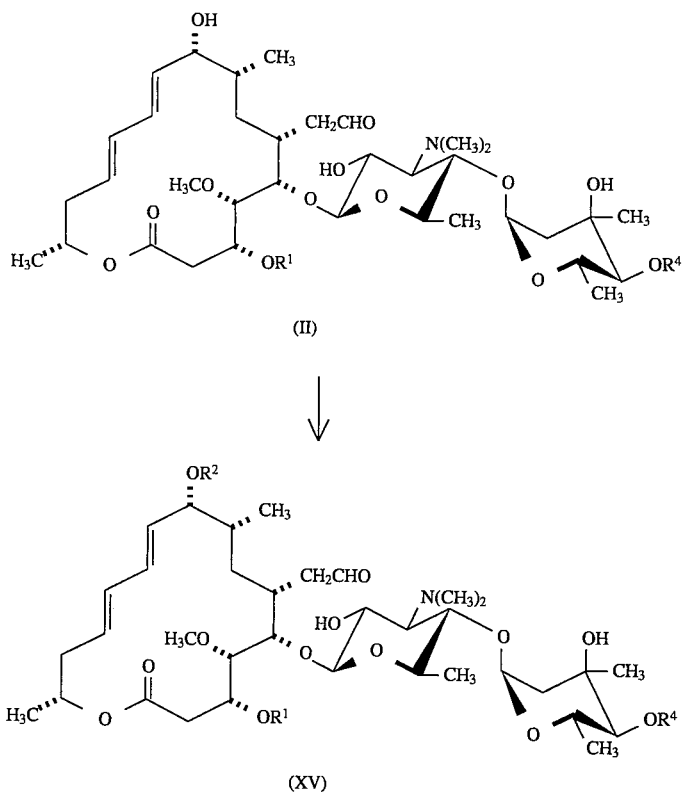

-continued
Reaction scheme 2-1
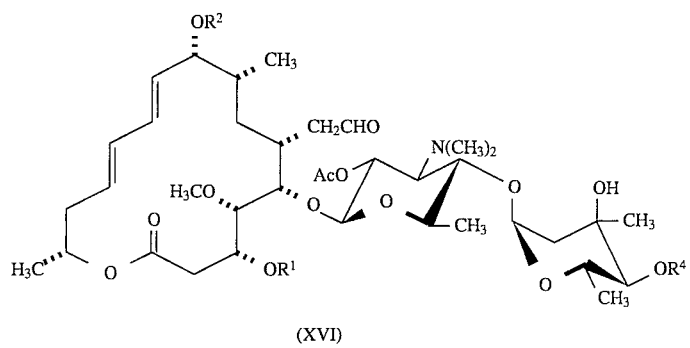
(XVI)
↓
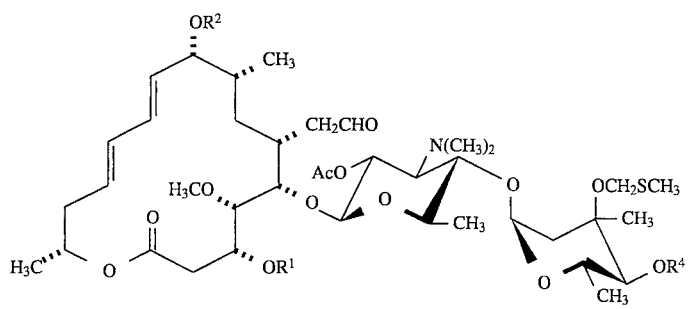
(XVII)
Reaction scheme 2-2
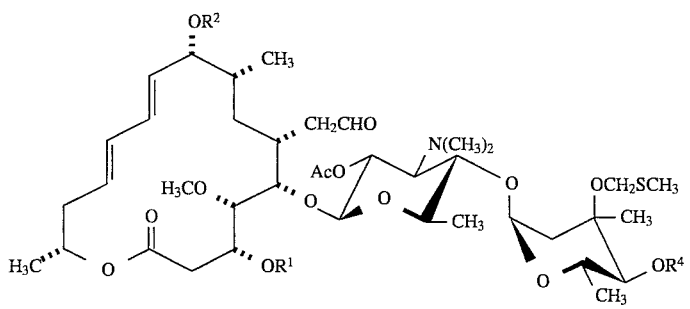
(XVII)

-continued
Reaction scheme 2-2

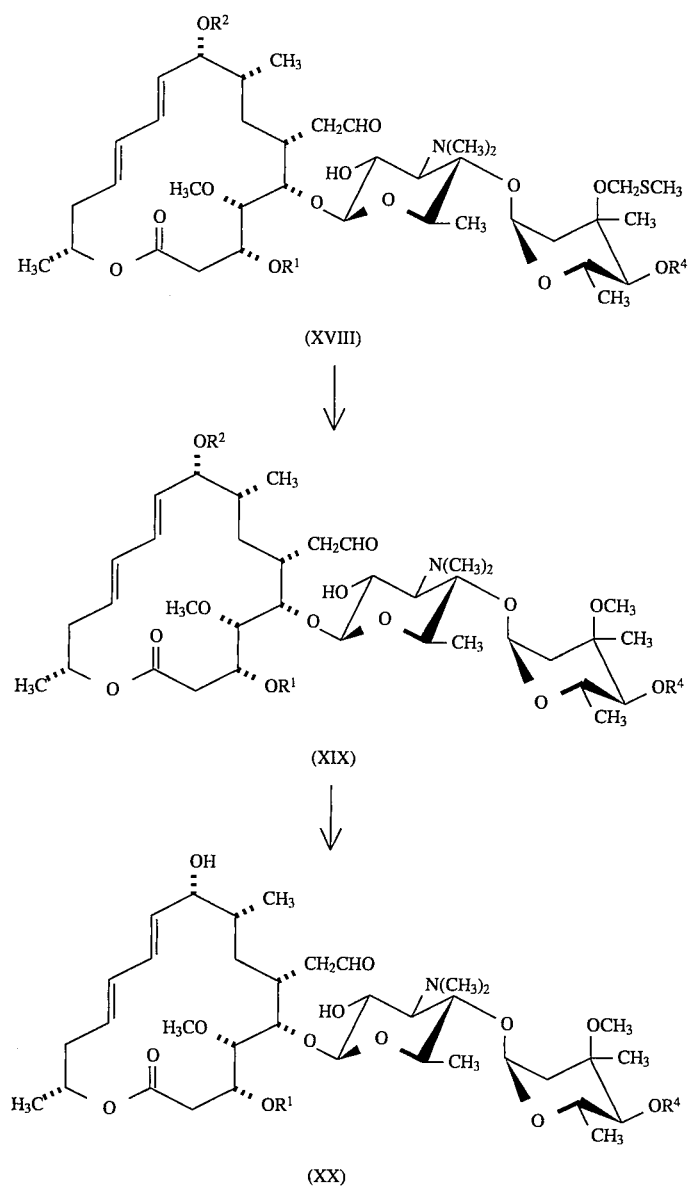

(XVIII)

(XIX)

(XX)

Firstly, the following describes a method for introducing a methyl group indirectly into a tertiary hydroxyl group at the 3"-position in a neutral sugar moiety of a compound whose hydroxyl group at the 3-position in a lactone ring and hydroxyl group at the 4"-position in a neutral sugar moiety are both acylated. Before describing the synthetic method, correlation among structure, antimicrobial activity in vitro and pharmacokinetics is briefly described with regard to a hydroxyl group at the 9-position of a lactone ring of a 16-membered macrolide derivative. When the hydroxyl group at the 9-position of said derivative is selectively acylated, or acetylated, the resulting compound shows an antimicrobial activity similar to or slightly lower than that of the intact derivative, with almost no reports on the significant increase in the activity. On the other hand, when an in vivo test is carried out using small animals such as mice, some of the compounds whose hydroxyl group at the 9-position is selectively acetylated show improved pharmacokinetics in the body or infection curing effect, but the others do not. Thus, influence of different structures at the 9-position upon the in vivo effects is greatly concerned in the structure of corresponding 16-membered macrolide derivative itself.

Hence, in designing a synthetic method for use in the efficient production of a 16-membered macrolide derivative, it is desirable to construct a production line which can separately produce a compound whose hydroxyl group at the 9-position is modified with a certain substituent group and a compound whose hydroxyl group at the 9-position is in the free form.

In this connection, it may be relatively convenient, from the viewpoint of reaction conditions in the protection step, to design the production process making use of an acyl group such as acetyl group as a protecting group of the hydroxyl group at the 9-position. However, in the chemical synthesis related to 16-membered macrolide derivatives, little is known about techniques for regenerating free hydroxyl group by removing an acyl group linked to the 9-position hydroxyl group in a high yield, while completely inhibiting other side reactions. Though a process has been reported in which an acetyl group linked to a hydroxyl group at the 9-position of a lactone ring of a 16-membered macrolide derivative is removed by a microbial conversion making use of a strain of actinomycetes [*Journal of Fermentation and Bioengineering,* 71(5), 370 (1991)], the conversion ratio seems to need to be improved.

In addition to a synthetic method in which a methyl group is introduced into a tertiary hydroxyl group at the 3"-position in a neutral sugar moiety of a 16-membered macrolide derivative under mild conditions to the utmost, the present inventors have found a method for quantitative protection and deprotection of the lactone ring 9-position hydroxyl group of the 16-membered macrolide derivative. Details of the method are described in the following with reference to the reaction scheme 2. Though a natural 16-membered macrolide antibiotic having an $sp^3$ carbon at the 9-position of a lactone ring is used as a starting material in the reaction scheme 2, it is possible to introduce a methyl group efficiently and indirectly into a tertiary hydroxyl group at the 3"-position based on the same methodology, when a compound having a carbonyl group at the 9-position is used as a starting material.

Firstly, a compound represented by the formula (XVI) is obtained by introducing a substituent group into two hydroxyl groups other than the 3"-position, namely hydroxyl groups at the 9- and 2'-positions, among free hydroxyl groups of a compound represented by the formula (II). In the first step, a hydroxyl group at the 9-position of a lactone ring of the compound of formula (II) (in this formula, $R^1$ is a straight-chain aliphatic acyl group having 2 to 4 carbon atoms and $R^4$ is a straight- or branched-chain aliphatic acyl group having 2 to 5 carbon atoms) is modified (or protected) with an appropriate substituent group to obtain a compound represented by the formula (XV) (in this formula, $R^1$ is a straight-chain aliphatic acyl group having 2 to 4 carbon atoms, $R^2$ is a substituent group which modifies (or protects) a hydroxyl group and $R^4$ is a straight- or branched-chain aliphatic acyl group having 2 to 5 carbon atoms).

Examples of the substituent group $R^2$ include not only lower aliphatic acyl groups [*Hakko to Kogyo,* 37(12), 1171 (1979)] but also other substituent groups which can be used for the usual hydroxyl group modification, such as methoxymethyl, ethoxyethyl and the like groups. In addition, when the substituent group $R^2$ is planned to be used as a protecting group of a hydroxyl group of a 16-membered macrolide derivative, it may be convenient to use an acetal base substituent group having an asymmetric carbon, such as 1-ethoxyethyl, tetrahydrofuranyl, tetrahydropyranyl or the like group. Protection of the hydroxyl group at the 9-position can be carried out by reacting the compound of the formula (II) with a 1 to 2 equivalent amount of a reagent such as dihydropyran, dihydrofuran or ethyl vinyl ether in methylene chloride (20 to 30 v/w) in the presence of acid catalyst such as p-toluenesulfonic acid or pyridinium p-toluenesulfonate (PPTS) at 20° to 40° C. for 1 to 24 hours.

As an example, a compound (12) (a compound of formula (XV) in which $R^1$ is a propionyl group, $R^2$ is a 1-ethoxyethyl group and $R^4$ is a propionyl group) was synthesized in a high yield by allowing medemycin (a compound of formula (II) in which $R^1$ is a propionyl group and $R^4$ is a propionyl group) to react with ethyl vinyl ether in dry methylene chloride in the presence of PPTS. In this instance, kinds of the substituent group to be used in this step and reaction conditions at the time of the introduction of the substituent group are not limited to those described herein, and not only substituent groups generally used as hydroxyl group-protecting groups (Theodora W. Greene and Peter G. M. Wuts, *Protective Groups in Organic Synthesis,* 2nd ed., Wiley: New York, 1991) but also other substituent groups which can hardly be used as protecting groups, as well as reaction conditions for their introduction, are all included in the scope of the present invention.

In this connection, when an acetal base protecting group having an asymmetric carbon, such as 1-ethoxyethyl group or the like, is introduced into a hydroxyl group at the 9-position of a lactone ring, the derivative exists as a mixture of two diastereomer while said substituent group is introduced. These isomers, however, may be separated or not separated. Also, these isomers may or may not be separated when said substituent group is regarded as a modifying group of a hydroxyl group at the 9-position of a lactone ring.

Next, a hydroxyl group at the 2'-position in the mycaminose (amino sugar) moiety of the compound of formula (XV) is protected with an acetyl group to obtain a compound represented by the formula (XVI) (in this formula, $R^1$ is a straight-chain aliphatic acyl group having 2 to 4 carbon atoms, $R^2$ is a substituent group which modifies (or protects) a hydroxyl group and $R^4$ is a straight- or branched-chain aliphatic acyl group having 2 to 5 carbon atoms). For example, a compound (13) (a compound of the formula (XVI) in which $R^1$ is a propionyl group, $R^2$ is a 1-ethoxyethyl group and $R^4$ is a propionyl group) was obtained quantitatively, by allowing the compound (12) to react with acetic anhydride in dry acetonitrile. In this case, a member of the compound of formula (XVI) in which $R^2$ is an acetyl group can be prepared from the compound of formula (II) by a single step. In addition, the compound of formula (XVI) can also be prepared easily, by selectively acetylating the 2'-position hydroxyl group in the mycaminose moiety of the compound of formula (II) and then introducing a substituent group into the 9-position hydroxyl group of a lactone ring. The acylation reaction at the 2'-position can be carried out by reacting the compound of the formula (XV) with a 1 to 2 equivalent amount of acid anhydride in an aprotic solvent such as acetonitrile in the absence of a base at about 20° C. for about 24 hours.

Secondly, process for the preparation of a methylthiomethyl ether synthetic intermediate to be used as a key compound is described. As a first step, a methylthiomethyl group is introduced into a tertiary hydroxyl group at the 3"-position in a neutral sugar moiety. It has been known since 1960's that methylthiomethyl ether is obtained as a by-product when dimethyl sulfoxide (DMSO) is reacted with acetic anhydride in order to oxidize a secondary hydroxyl group into a carbonyl group [*Journal of American Chemical Society,* 89(10), 2416 (1967)]. It has been reported in the middle of 1970's by a Japanese research group that methylthiomethyl group is most suitable as a protecting group of tertiary hydroxyl groups for the synthesis of natural organic compounds [*Tetrahedron Letters,* 65 (1976)]. In the latter half of 1970's, a theoretical interpretation has been reported concerning effect of the addition of acetic acid to a reaction system on the progress of methylthiomethylation in preference to oxidation [*Australian Journal of Chemistry,* 31, 1031 (1978)].

As a first step, a hydroxyl group at the 3"-position of the compound of formula (XVI) is methylthiomethylated in accordance with a method reported by a research group of the present applicant [*Journal of Antibiotics,* 33(1), 61 (1980)] to obtain a compound represented by (XVII) (in this formula, $R^1$ is a straight-chain aliphatic acyl group having 2 to 4 carbon atoms, $R^2$ is a substituent group which modifies (or protects) a hydroxyl group and $R^4$ is a straight- or branched-chain aliphatic acyl group having 2 to 5 carbon atoms) in a yield of about 60 to 70%. The reaction can be carried out by reacting the compound of the formula (XVII) with 20 to 30 v/w of DMSO in the presence of 3 to 15 v/w of acetic anhydride at 20° to 40° C. for about 24 hours. As an example, a compound (14) (a compound of formula (XVII) in which $R^1$ is a propionyl group, $R^2$ is a 1-ethoxyethyl group and $R^4$ is a propionyl group) was synthesized by allowing the compound (13) to react with DMSO and acetic anhydride. Since there are many known methods with regard to the introduction of methylthiomethyl group into hydroxyl group. (Theodora W. Greene and Peter G. M. Wuts, *Protective Groups in Organic Synthesis,* 2nd ed., Wiley: New York, 1991), the inventive production process is not limited by the above methylthiomethyl group-introducing method and all known methods related to said introducing methods are included in the scope of the present invention.

Next, an acetyl group linked to a hydroxyl group at the 2'-position of the compound of formula (XVII) is deprotected to obtain a key compound represented by the formula (XVIII) (in this formula, $R^1$ is a straight-chain aliphatic acyl group having 2 to 4 carbon atoms, $R^2$ is a substituent group which modifies (or protects) a hydroxyl group and $R^4$ is a straight- or branched-chain aliphatic acyl group having 2 to 5 carbon atoms), namely a methylthiomethyl ether synthetic intermediate, in a quantitative yield. For example, a compound (15) (a compound of the formula (XVIII) in which $R^1$ is a propionyl group, $R^2$ is a 1-ethoxyethyl group and $R^4$ is a propionyl group) was obtained by allowing the compound (14) to react in a protic solvent such as methanol (20 to 50 v/w) at about 20° C. for about 24 hours.

Thirdly, the methylthiomethyl group introduced into a tertiary hydroxyl group at the 3"-position in a neutral sugar moiety of the key intermediate represented by formula (XVIII) is selectively reduced, thereby effecting efficient synthesis of a 16-membered macrolide derivative whose tertiary hydroxyl group at the 3"-position is methylated. Triggered by a report in the field of carbohydrate chemistry on the chemical conversion of a methylthiomethylated secondary hydroxyl group into a methoxy group by its reduction with Raney nickel [*Carbohydrate Research,* 7,474 (1968)], similar reactions have been reported [*Tetrahedron Letters,* 43 (1969); and *Carbohydrate Research,* 15, 101 (1970)]. Relatively recently, it has been reported that primary and secondary hydroxyl groups into which an arylthiomethyl group has been introduced as a substituent group in stead of a methylthiomethyl group were chemically converted into methoxy groups when radical reduction and the like were applied [*Journal of Organic Chemistry,* 54(25), 5998 (1989)].

As described above, the methodology itself for reducing a methylthiomethylated hydroxyl group into a methoxy group is not novel, but most of the reduction reactions have been applied to secondary hydroxyl groups. In addition, most of the reaction substrates so far reported have no functional groups which show reactivity to catalytic reduction, such as double bond, free aldehyde group and the like.

The present inventors have found a practical preparation method in which a compound represented by the formula (XIX) (in this formula, $R^1$ is a straight-chain aliphatic acyl group having 2 to 4 carbon atoms, $R^2$ is a substituent group which modifies (or protects) a hydroxyl group and $R^4$ is a straight- or branched-chain aliphatic acyl group having 2 to 5 carbon atoms) is selectively synthesized using Raney nickel whose activity is controlled at a proper level, by chemically converting a methylthiomethylated tertiary hydroxyl group at the 3"-position into a methoxy group without causing reduction of double bond and free aldehyde group in the compound represented by formula (XVIII). The reduction reaction can be carried out in a solvent such as ethanol or dioxane (20 to 30 v/w) in the presence of 10 to 30 v/w of Raney Nickel at about 20° C. for about 1 hour with vigorous stirring. For example, a compound (16) (a compound of the formula (XIX) in which $R^1$ is a propionyl group, $R^2$ is a 1-ethoxyethyl group and $R^4$ is a propionyl group) was selectively synthesized by stirring the compound (15), for a short period at room temperature, in ethanol together with Raney nickel whose activity was controlled at a proper level. This selective reduction reaction progresses efficiently also when $R^2$ is modified (or protected) with a substituent group other than acetal base groups, such as an acetyl group in the case of a compound (7) (a compound of the formula (XVIII) in which $R^1$ is a propionyl group, $R^2$ is an acetyl group and $R^4$ is a propionyl group) (cf. Example 7).

Conditions for this selective reduction reaction, such as control of Raney nickel activity, reaction solvent and treatment after the reaction, will be described later in Example 7, but the production process of the present invention is not limited by these reaction conditions and their modifications are also included in the inventive production process.

That is, the Raney nickel activity may be controlled not only by the acetone-aided method described in Example 7 of the present invention but also by the use of ethyl acetate, hot water and the like. Alternatively, selectivity of the reaction may be improved by supplementing the reaction system with a certain organic or inorganic compound which contains nitrogen, sulfur or the like atom. Also, the reaction solvent is not limited to a lower alcohol such as ethanol, and the reaction may be effected by the use of an ethereal organic solvent such as 1,4-dioxane. The treatment after the reaction is also not limited, provided that the reaction product can be separated from Raney nickel with a high efficiency without causing decomposition of the product.

The compound represented by formula (XIX) thus prepared in the aforementioned manner is by itself capable of inhibiting growth of clinically important Gram-positive bacteria and showing excellent effects in vivo. In this connection, when $R^2$ is a certain acetal base substituent group such as 1-ethoxyethyl, tetrahydrofuranyl, tetrahydropyranyl or the like group, it can be deprotected in a high yield.

That is, a compound represented by the formula (XX) (in this formula, $R^1$ is a straight-chain aliphatic acyl group having 2 to 4 carbon atoms and $R^4$ is a straight- or branched-chain aliphatic acyl group having 2 to 5 carbon atoms) can be obtained quantitatively, by deprotecting a substituent group introduced into a hydroxyl group at the 9-position of a lactone ring of the compound of formula (XIX) under conditions suitable for the substituent group (Theodora W. Greene and Peter G. M. Wuts, *Protective Groups in Organic Synthesis,* 2nd ed., Wiley: New York, 1991). The deprotection reaction can be carried out in a solvent (20 to 30 v/w) such as lower alcohol (e.g., methanol, ethanol), acetonitrile or THF in the presence of acid catalyst such as p-toluenesulfonic acid, diluted hydrochloric acid or 5% acetic acid at about 20° C. for 1 to 24 hours. For example, a compound (1) (a compound of the formula (XX) in which $R^1$ is a propionyl group and $R^4$ is a propionyl group) was obtained by allowing the compound (16) to react in a mixed solvent of 5% acetic acid aqueous solution:acetonitrile (3:1). The thus obtained compound represented by formula (XX) also strongly inhibits growth of clinically important Gram-positive bacteria by itself.

In the reaction scheme 2, when a compound represented by the formula (XX) is synthesized from a compound of formula (XVIII), a methylthiomethyl ether at the 3"-position in a neutral sugar moiety is reduced into a methoxy group, and then a substituent group linked to a hydroxyl group at the 9-position of a lactone ring is deprotected. On the other hand, it is possible to produce the compound of formula (XX) by firstly deprotecting the 9-position and then reducing the 3"-position. However, yield and selectivity in the selective reduction reaction is more excellent when the compound of formula (XVIII) is used as a substrate.

In this instance, novel and useful substances can be created based on the present invention by selectively acylating a hydroxyl group at the 9- or 2'-position of the compound represented by the formula (XX) or a salt thereof in accordance with a known method [*Hakko to Kogyo*, 37(12), 1171 (1979)], by subjecting the hydroxyl group at the 9-position of the compound to allylic rearrangement into the 11- or 13-position in the presence of a dilute acid in accordance with a known method [*Chemical and Pharmaceutical Bulletin*, 18(8), 1501 (1970); *Scientific Report of Meiji Seika Kaisha*, 12, 85 (1972); and *Journal of Antibiotics*, 35(11), 1521 (1982)] or by selectively oxidizing the hydroxyl group at the 9-position in accordance with a known method [*Journal of Antibiotics*, 24(8), 526 (1971)].

The gist of the fourth aspect of the present invention resides in a novel production process by which a compound represented by the formula (VI):

wherein $R^4$ represents a straight- or branched-chain aliphatic acyl group having 2 to 5 carbon atoms, or a salt thereof, as a starting material, via a synthetic intermediate in which a hydroxyl group at the 3"-position is substituted with a methylthiomethyl ether, represented by the formula (V):

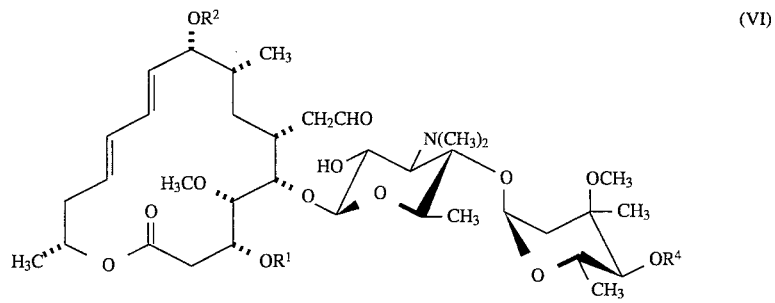

(VI)

wherein $R^1$ represents a hydrogen atom or a substituent group which modifies (or protects) a hydroxyl group; $R^2$ represents a hydrogen atom or a substituent group which modifies (or protects) a hydroxyl group; and $R^4$ represents a straight- or branched-chain aliphatic acyl group having 2 to 5 carbon atoms, or a salt thereof, can be produced by means of pure chemical synthesis from a naturally occurring 16-membered macrolide antibiotic represented by the formula (IV)

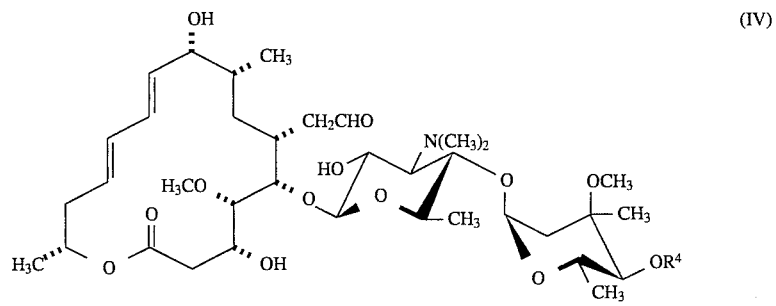

(IV)

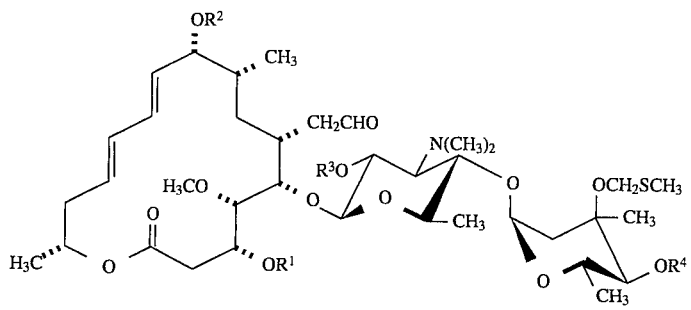
(V)

wherein R¹ represents a substituent group which modifies (or protects) a hydroxyl group; R² represents a substituent group which modifies (or protects) a hydroxyl group; R³ represents a hydrogen atom or a substituent group which protects a hydroxyl group; and R⁴ represents a straight- or branched-chain aliphatic acyl group having 2 to 5 carbon atoms, or a salt thereof. The compound of the present invention represented by the formula (VI) can be produced in accordance with the procedure shown in the following reaction scheme 3.

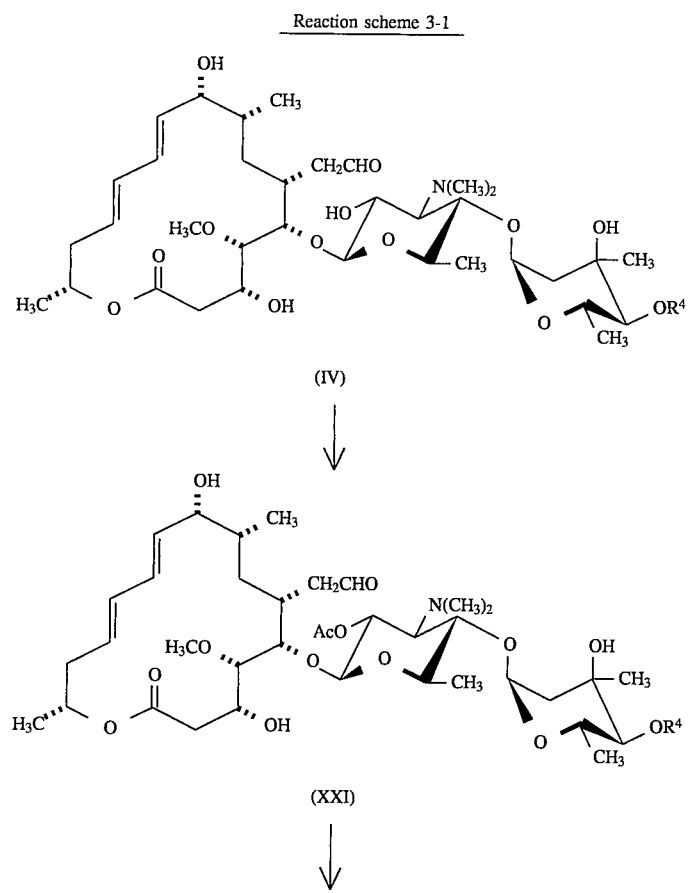

-continued
Reaction scheme 3-1
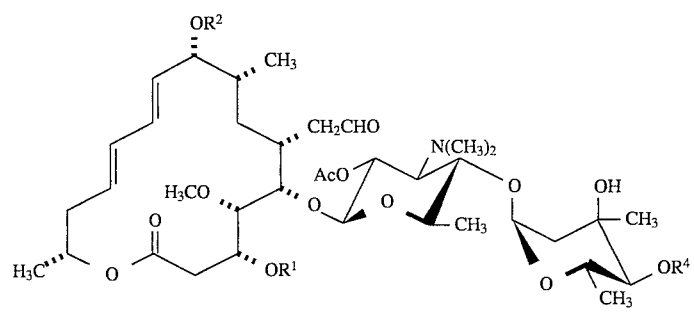
(XXII)
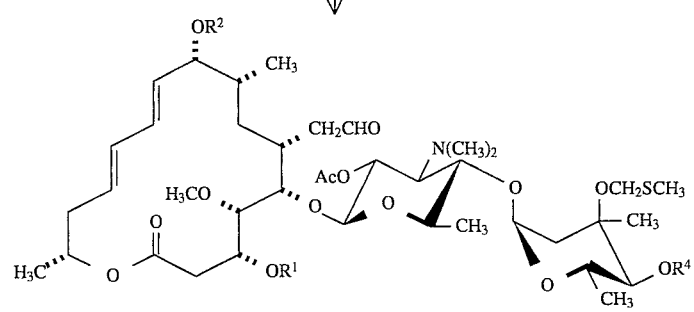
(XXIII)
Reaction scheme 3-2
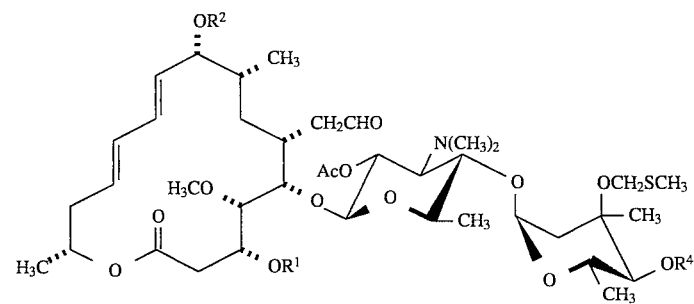
(XXIII)

-continued
Reaction scheme 3-2

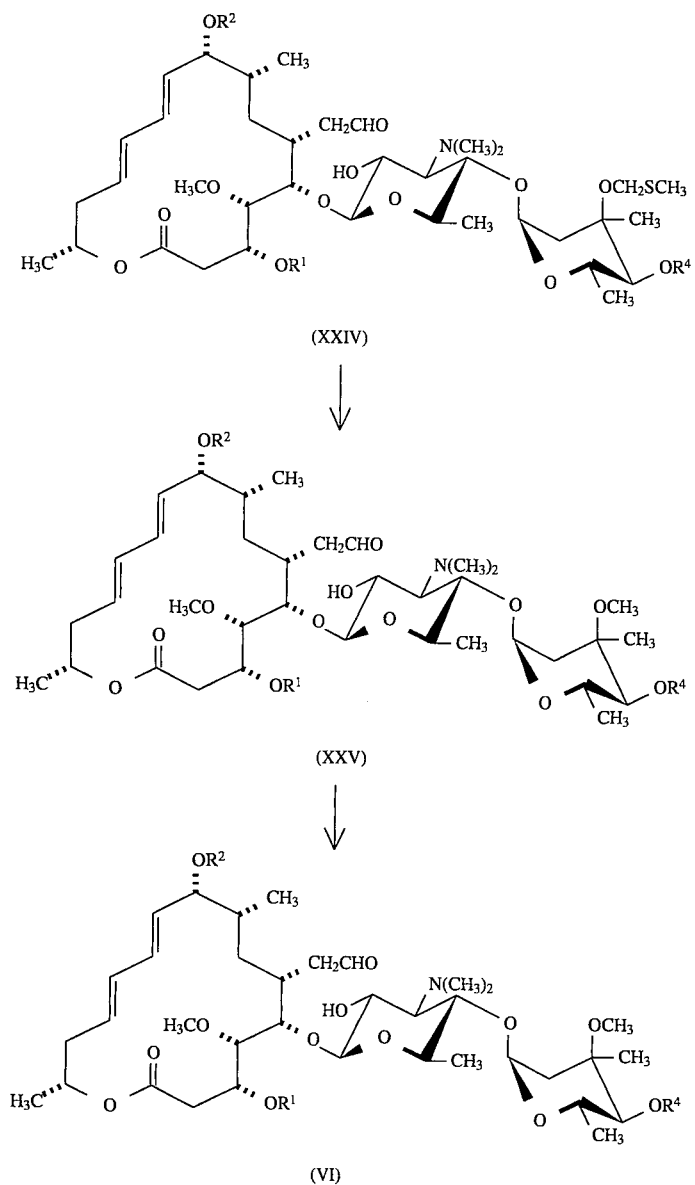

The introduction of an alkyl group into a hydroxyl group of a neutral sugar moiety of a 16-membered macrolide derivative via no glycosylation are roughly divided into two methods in view of the difference in chemical reactivities. One method comprises introducing an alkyl group into a secondary hydroxyl group which is relatively rich in reactivity, and the other method comprises introducing it into a tertiary hydroxyl group having poor reactivity. There are two examples of the former method, in which an alkyl group is introduced, via a proper intermediate, into a secondary hydroxyl group at the 4"-position of the mycarose moiety of a spiramycin derivative reported by Ōmura, Sano et al. (JP-A-60-58998; and JP-A-60-239494) and a tylosin derivative reported by Yoshioka et al. (JP-A-62-234093).

An example of the latter method which has been applied for a patent by the present inventors is a synthetic process for producing various derivatives which comprises protecting starting leucomycins having a free hydroxyl group at the 3-position with a silyl group, removing an acyl group, subsequently alkylating the 4"-position (secondary hydroxyl group) and 3"-position (tertiary hydroxyl group) of the neutral sugar moiety under appropriate conditions and effecting deprotection (EP-A-0 595 303). This invention is characterized in that not only methyl group but also other alkyl groups can be introduced into the tertiary hydroxyl group which is poor in reactivity, because the alkyl group is introduced directly under a strongly basic condition.

The target compound to be used herein is a 16-membered macrolide derivative of leucomycins which have free hydroxyl groups at the 3- and 9-positions of the lactone ring (the hydroxyl group at the 9-position may be acylated) and an acylated hydroxyl group at the 4"-position of the neutral sugar moiety, wherein a hydroxyl group at the 3"-position of said derivative is methylated. With regard to the neutral sugar moiety of this derivative, the hydroxyl group at the 4"-position is acylated as described above. From a carbohydrate chemical point of view, when one of adjoining cis hydroxyl groups is acylated (the 4"-position for instance)

and the other is in the free form (the 3"-position for instance), direct methylation of a free hydroxyl group (the 3"-position for instance) generates various side reactions. Hence, when a methyl group is introduced into a hydroxyl group at the 3"-position of the neutral sugar moiety as a key reaction in the synthesis of said derivative, it is necessary to carry out the reaction under mild conditions in order to prevent damage on the 4"-position acyl group. In consequence, a method in which the reaction is effected via a methylthiomethyl ether synthetic intermediate was selected in the production process of the present invention to obviate the side reactions.

Since the introduction of a methyl group into a hydroxyl group via a methylthiomethyl ether synthetic intermediate does not always require protection of an aldehyde group at the 18-position, protection of a hydroxyl group at the 3-position of a lactone ring in the production process of the present invention is effected by the use of an acetal base substituent group having an asymmetric carbon atom, which is inexpensive and can be removed under a mild condition. Though a natural 16-membered macrolide antibiotic having an $sp^3$ carbon at the 9-position of a lactone ring is used as a starting material in the reaction scheme 3, it is possible to introduce a methyl group efficiently and indirectly into a tertiary hydroxyl group at the 3"-position based on the same methodology, when a compound having a carbonyl group at the 9-position is used as a starting material.

Firstly, a compound represented by the formula (XXII) is obtained by introducing the same or different substituent groups into three hydroxyl groups other than the 3"-position, namely hydroxyl groups at the 3-, 9- and 2'-positions, among free hydroxyl groups of a compound represented by the formula (IV). In the first step, a hydroxyl group at the 2'-position of the mycaminose (amino sugar) moiety of the compound of formula (IV) (in this formula, $R^4$ is a straight- or branched-chain aliphatic acyl group having 2 to 5 carbon atoms) is protected with an acetyl group to obtain a compound represented by the formula (XXI) (in this formula, $R^4$ is a straight- or branched-chain aliphatic acyl group having 2 to 5 carbon atoms). The protection at the 2'-position can be carried out in the same manner as in the above-mentioned reaction scheme 2. For example, a compound (28) [*Journal of Medicinal Chemistry,* 20(5), 732 (1977); a compound of the formula (XXI) in which $R^4$ is a normal butyryl group] was obtained quantitatively, by allowing leucomycin $A_5$ [*Journal of Antibiotics,* Ser.A, 20(4), 234 (1967); a compound of the formula (IV) in which $R^4$ is a normal butyryl group] to react with acetic anhydride in dry acetonitrile.

Next, a substituent group is introduced into hydroxyl groups at the 3- and 9-positions of a lactone ring of the compound of formula (XXI) to obtain a compound represented by the formula (XXII) (in this formula, $R^1$ is a substituent group which modifies (or protects) a hydroxyl group, $R^2$ is a substituent group which modifies (or protects) a hydroxyl group and $R^4$ is a straight- or branched-chain aliphatic acyl group having 2 to 5 carbon atoms). The same reaction conditions as described in the reaction scheme 2 can be used. As an example, a compound (29) (a compound of formula (XXII) in which $R^1$ is a 1-ethoxyethyl group, $R^2$ is a 1-ethoxyethyl group and $R^4$ is a normal butyryl group) was obtained in a high yield by allowing the compound (28) to react with ethyl vinyl ether in dry methylene chloride in the presence of PPTS.

In this instance, kinds of the substituent group to be used in this step and reaction conditions at the time of the introduction of the substituent group are not limited to those described herein, and not only substituent groups generally used as hydroxyl group-protecting groups (Theodora W. Greene and Peter G. M. Wuts, *Protective Groups in Organic Synthesis,* 2nd ed., Wiley: New York, 1991) but also other substituent groups which can hardly be deprotected with regard to said substrate, as well as reaction conditions for their introduction, are all included in the scope of the present invention. Of these, an acetal base substituent group having an asymmetric carbon atom, such as 1-ethoxyethyl, tetrahydrofuranyl, tetrahydropyranyl or the like group is particularly preferred in view of mild deprotection conditions.

In this connection, when an acetal base protecting group having an asymmetric carbon, such as 1-ethoxyethyl group or the like, is introduced into hydroxyl groups at the 3- and 9-positions of0a lactone ring, the derivative exists as a mixture of four diastereoisomers while said substituent group is introduced. These isomers, however, may be separated or not separated. Also, these isomers may not be separated when said substituent group is regarded as a modifying group of a hydroxyl group at the 3-position of a lactone ring.

On the other hand, the substituent group at the 9-position hydroxyl group of a lactone ring, namely $R^2$, is not necessarily be the same as $R^1$. For example, it is possible to obtain a compound of the formula (XXII) by introducing the same substituent group such as acetyl group into hydroxyl groups at the 9- and 2'-positions and then introducing an acetal base substituent group having an asymmetric carbon atom, such as 1-ethoxyethyl group, into the 3-position hydroxyl group of a lactone ring (cf. Example 34).

Though not shown in the reaction scheme 3, it is possible to prepare a reaction substrate for methylthiomethylation by introducing the same acetal base substituent group such as 1-ethoxyethyl group into three free hydroxyl groups at the 3-, 9- and 2'-positions of the compound of formula (IV).

Secondly, a methylthiomethyl ether synthetic intermediate to be used as a key compound is prepared and the 2'-position acetyl group is deprotected. Details about the synthesis of methylthiomethyl ether were already described in the foregoing and therefore are omitted herein. As a first step, a hydroxyl group at the 3"-position of the compound of formula (XXII) is methylthiomethylated in accordance with a method reported by a research group of the present applicant [*Journal of Antibiotics,* 33(1), 61 (1980)] to obtain a compound represented by (XXIII) (in this formula, $R^1$ is a substituent group which modifies (or protects) a hydroxyl group, $R^2$ is a substituent group which modifies (or protects) a hydroxyl group and $R^4$ is a straight- or branched-chain aliphatic acyl group having 2 to 5 carbon atoms) without generating by-products. The same reaction conditions as described in the above reaction sheme 2 can be used. As an example, a compound (30) (a compound of formula (XXIII) in which $R^1$ is a 1-ethoxyethyl group, $R^2$ is a 1-ethoxyethyl group and $R^4$ is a normal butyryl group) was synthesized by allowing the compound (29) to react with DMSO and acetic anhydride.

Next, the acetyl group linked to a hydroxyl group at the 2'-position of the compound of formula (XXIII) is deprotected to obtain a key compound represented by the formula (XXIV) (in this formula, $R^1$ is a substituent group which modifies (or protects) a hydroxyl group, $R^2$ is a substituent group which modifies (or protects) a hydroxyl group and $R^4$ is a straight- or branched-chain aliphatic acyl group having 2 to 5 carbon atoms), namely a methylthiomethyl ether synthetic intermediate, with a quantitative yield in the same manner as described in the above reaction scheme 2. For example, a compound (31) (a compound of the formula (XXIV) in which $R^1$ is a 1-ethoxyethyl group, $R^2$ is a 1-ethoxyethyl group and $R^4$ is a normal butyryl group) was obtained by allowing the compound (30) to undergo the reaction in methanol.

Thirdly, the methylthiomethyl group introduced into a tertiary hydroxyl group at the 3"-position of a neutral sugar moiety of the key intermediate represented by formula (XXIV) is selectively reduced in the same manner as described in the above reaction sheme 2, thereby effecting efficient synthesis of a 16-membered macrolide derivative whose tertiary hydroxyl group at the 3"-position is methylated. Methodology for the catalytic reduction of the methylthiomethylated hydroxyl group into a methoxy group and various problems concerning application of the method to the synthesis of 16-membered macrolide derivatives have been described in the foregoing in detail and therefore are omitted herein. Similarly, control of the activity of metal-catalysts to be used in the selective reduction reaction and related conditions thereto are also not described herein.

As a first step, a compound represented by the formula (XXV) (in this formula, $R^1$ is a substituent group which modifies (or protects) a hydroxyl group, $R^2$ is a substituent group which modifies (or protects) a hydroxyl group and $R^4$ is a straight- or branched-chain aliphatic acyl group having 2 to 5 carbon atoms) is selectively synthesized using Raney nickel whose activity is controlled at a proper level, by chemically converting a methylthiomethylated tertiary hydroxyl group at the 3"-position into a methoxy group without causing reduction of double bond and free aldehyde group in the compound represented by formula (XXIV).

Next, a compound represented by the formula (VI) (in this formula, $R^1$ is a hydrogen atom or a substituent group which modifies (or protects) a hydroxyl group, $R^2$ is a hydrogen atom or a substituent group which modifies (or protects) a hydroxyl group and $R^4$ is a straight- or branched-chain aliphatic acyl group having 2 to 5 carbon atoms) is obtained in a high yield by, if necessary, deprotecting a substituent group introduced into a hydroxyl group(s) at the 3- and/or 9-position of a lactone ring of the compound of formula (XXV), after its separation or as it is, under conditions suitable for the substituent group (Theodora W. Greene and Peter G. M. Wuts, *Protective Groups in Organic Synthesis*, 2nd ed., Wiley: New York, 1991). The same reaction conditions as described in the above reaction scheme 2 can be used.

For example, a compound (32) (a compound of the formula (XXV) in which $R^1$ is a 1-ethoxyethyl group, $R^2$ is a 1-ethoxyethyl group and $R^4$ is a normal butyryl group) was obtained selectively, by stirring the compound (31), for a short period at room temperature, in ethanol together with Raney nickel whose activity was controlled at a proper level. Thereafter, without carrying out separation, the resulting compound was allowed to react in a mixed solvent of 5% acetic acid aqueous solution/acetonitrile (3:1) to obtain a compound (33) (a compound of the formula (VI) in which $R^1$ is a hydrogen atom, $R^2$ is a hydrogen atom and $R^4$ is a normal butyryl group). A certain derivative of the thus obtained compound represented by the formula (VI) inhibits growth of clinically important Gram-positive bacteria extremely strongly by itself comparable to the 14-membered new macrolide. This selective reduction reaction also progresses without difficulty when $R^2$ is modified (or protected) with a substituent group other than acetal base groups, such as an acetyl or the like acyl group in the case of a compound (37) (a compound of the formula (XXIV) in which $R^1$ is a 1-ethoxyethyl group, $R^2$ is an acetyl group and $R^4$ is a normal butyryl group) (cf. Examples 38 and 39).

In the reaction scheme 3, when a compound represented by the formula (VI) is synthesized from a compound of formula (XXIV), a methylthiomethyl ether at the 3"-position in a neutral sugar moiety is reduced into a methoxy group, and then a substituent group linked to a hydroxyl group(s) at the 3- and/or 9-position of a lactone ring is deprotected. On the other hand, it is possible to produce the compound of formula (VI) by firstly deprotecting the 3- and/or 9-position and then reducing the 3"-position.

Though not shown in the reaction scheme, when the same protective group such as an acetal base substituent group is introduced into three free hydroxyl groups at the 3, 9- and 2'-positions of the compound of formula (IV) and then a hydroxyl group at the 3"-position is methylthiomethylated, it is possible to selectively convert the 3"-position to a methoxy group after deprotection of the substituent groups introduced into the three hydroxyl groups. In this instance, deprotection can be effected at the last step.

In this instance, novel and useful substances can be created based on the present invention by selectively acylating a hydroxyl group at the 9- or 2'-position of the compound represented by the formula (VI) or a salt thereof in accordance with a known method [Hakko to Kogyo, 37(12), 1171 (1979)], by subjecting the hydroxyl group at the 9-position of the compound to allylic rearrangement into the 11- or 13-position in the presence of a dilute acid in accordance with a known method [*Chemical and Pharmaceutical Bulletin*, 18(8), 1501 (1970); *Scientific Report of Meiji Seika Kaisha*, 12, 85 (1972); and *Journal of Antibiotics*, (11), 1521 (1982)] or by selectively oxidizing the hydroxyl group at the 9-position in accordance with a known method [*Journal of Antibiotics*, 24 (8), 526 (1971)].

In the examples of the present invention, the production process was described with reference to a case in which $R^4$, namely an acyl side chain to be linked to a hydroxyl group at the 4"-position of a neutral sugar moiety, is a normal butyryl group. However, the production process of the present invention is not limited to said acyl side chain and can be carried out in the case of compounds having any other natural type acyl side chains.

In Example 42, a compound (40) (a compound of the formula (I) in which $R^1$ is a hydrogen atom, $R^2$ is a propionyl group, $R^3$ is a hydrogen atom and $R^4$ is a normal butyryl group) was produced from the compound (33) by a single step. The compound (40) can also be produced easily making use of the process used for the production of a compound (39) (a compound of the formula (I) in which $R^1$ is a hydrogen atom, $R^2$ is an acetyl group, $R^3$ is a hydrogen atom and $R^4$ is a normal butyryl group).

The gist of the fifth aspect of the present invention resides in a novel general production process by which a compound represented by the formula (VIII)

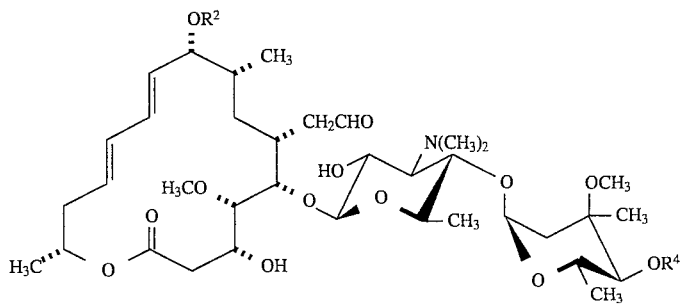
(VIII)

wherein $R^2$ represents a hydrogen atom or a substituent group which modifies a hydroxyl group and $R^4$ represents a straight or branched-chain aliphatic or aromatic acyl group having 1 to 10 carbon atoms, or a salt thereof can be obtained via a synthetic intermediate whose hydroxyl group at the 3"-position is methylthiomethylated, represented by the formula (VII)

a starting material. The compound of the present invention represented by the general formula (VIII) can be produced in accordance with the procedure shown in the following reaction scheme 4.

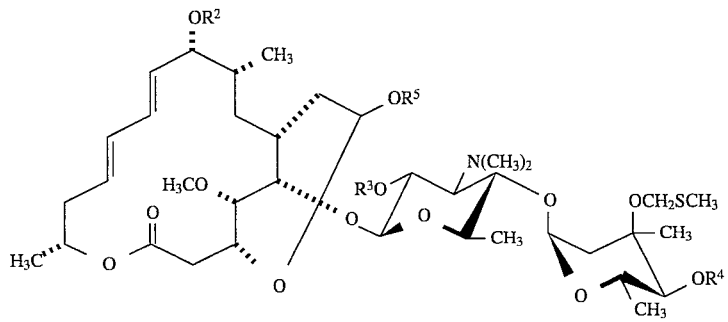
(VII)

wherein $R^2$ represents a hydroxyl group-protecting group such as a silyl protecting group, an acetal base protecting group or the like or a substituent group which modifies a hydroxyl group, $R^3$ represents an acetyl group or a silyl protecting group, $R^4$ represents a straight- or branched-chain aliphatic or aromatic acyl group having 1 to 10 carbon atoms and $R^5$ represents a silyl protecting group, or a salt thereof, using a naturally occurring 16-membered macrolide antibiotic represented by the formula (IV)

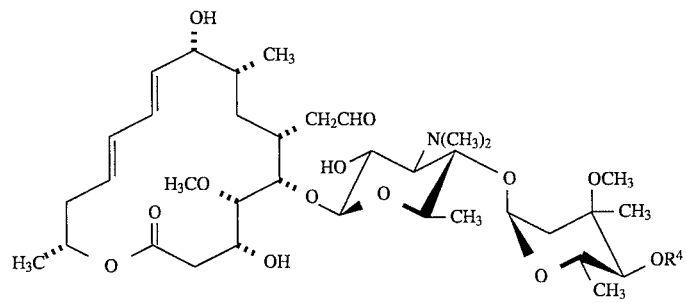
(IV)

wherein $R^4$ represents a straight- or branched-chain aliphatic acyl group having 2 to 5 carbon atoms, or a salt thereof as Reaction scheme 4-1
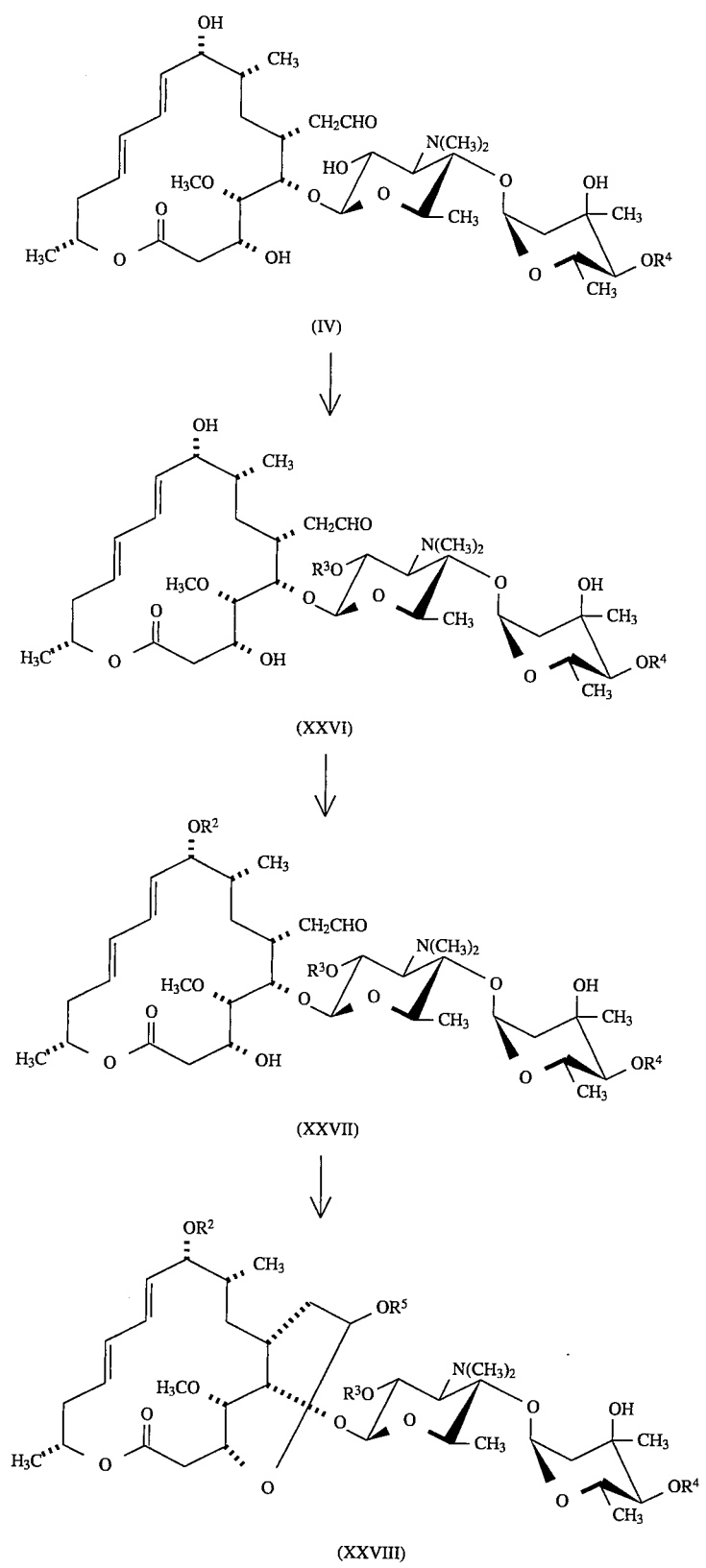
(IV)
(XXVI)
(XXVII)
(XXVIII)

Reaction scheme 4-2
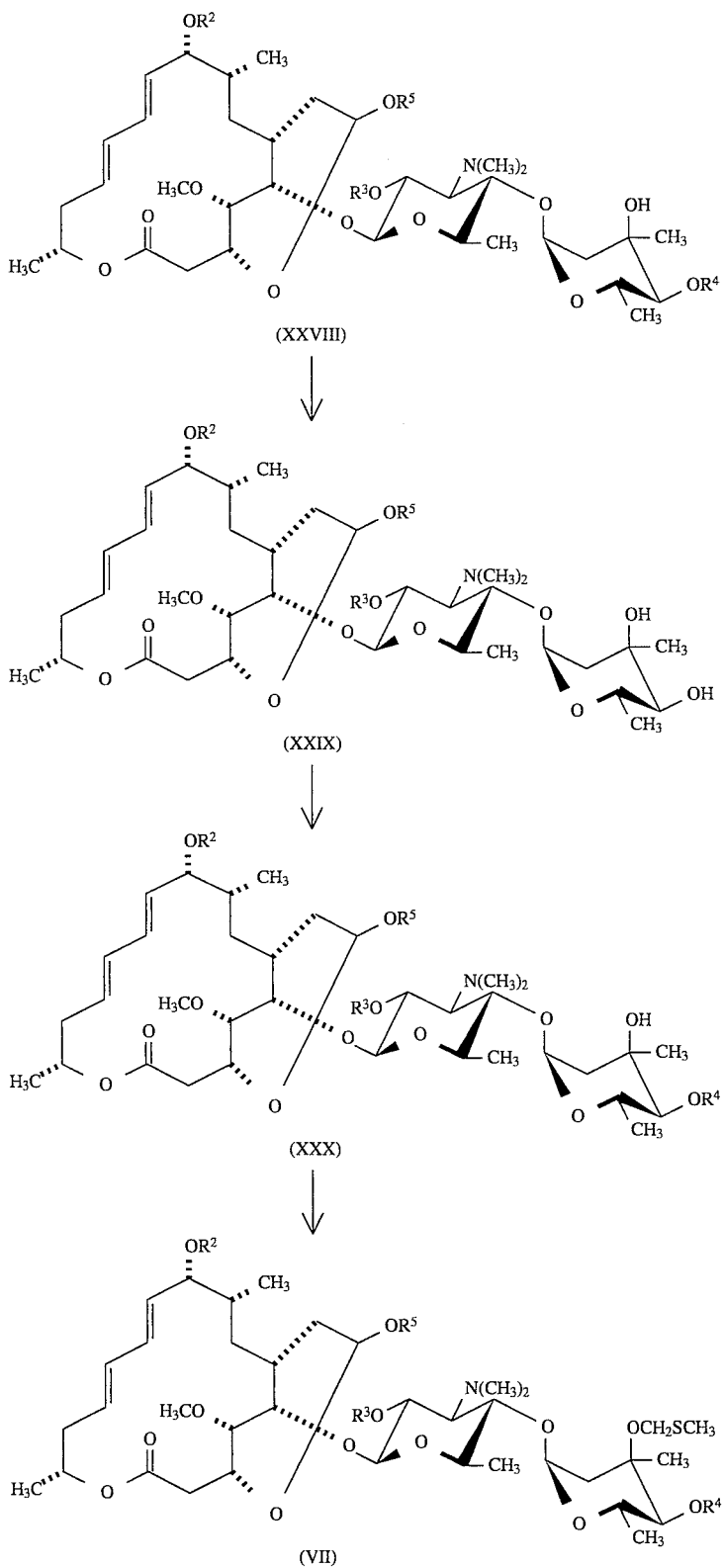

Reaction scheme 4-3

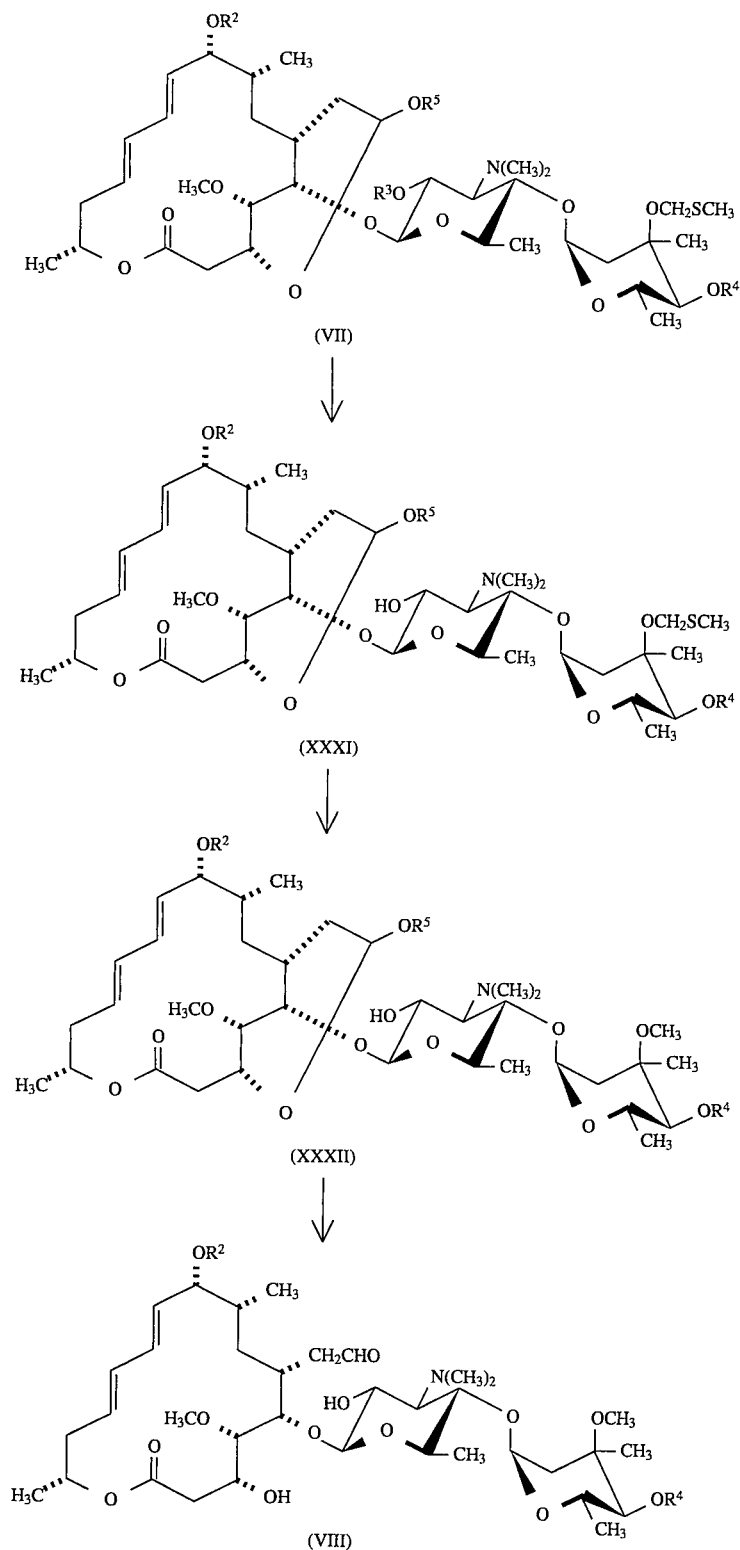

Difference in the structure of an acyl side chain at the 4"-position in a neutral sugar moiety in a 16-membered macrolide compound is greatly related to its antimicrobial activity in vitro [*Journal of Antibiotics*, 28(6), 401 (1975)]. In consequence, it is desirable to design a process for the production of the derivative of interest into such a general purpose system that conversion of the 4"-position acyl side chain can be effected. By the way, in the aforementioned process which is effected via a methylthiomethyl ether synthetic intermediate, the 4"-position acyl side chain of the practically produced compound is limited to that of the starting material used, because the process uses a naturally-occurring 16-membered macrolide compound as a starting material, and an acyl side chain originated from the material is simultaneously used as a protecting group of a hydroxyl group at the 4"-position. On the other hand, a diol synthetic key intermediate disclosed in a prior application (Japanese Patent Application No. 5-206731), which is protected with three silyl groups and produced using a leucomycin Fr group as a starting material, has a free hydroxyl group at the 4"-position which is suitable for chemical modifications such as acylation. In consequence, this synthetic key intermediate was positively applied to the production process of the present invention in order to render possible creative chemical modifications of the acyl side chain at the 4"-position and introduction of not only an aliphatic acyl group but also an aromatic acyl group.

In other words, the present inventors have succeeded in establishing a production process in which a leucomycin Fr group is used as a starting material and chemical conversion of its acyl side chain at the 4"-position can be effected and by which a compound whose hydroxyl group at the 9-position is in the free form and another compound whose hydroxyl group at the 9-position is modified with a certain substituent group can be produced separately with a single key reaction.

As an example of the production process, the following describes in detail a general purpose synthetic method which can convert the 4"-position acyl side chain and in which a silyl group is used as a protecting group of the 9-position hydroxyl group and an acetyl group is used as a protecting group of the 2'-position hydroxyl group, with reference to the reaction scheme 4. In this instance, it is possible to produce the compound of interest of the present invention without difficulty in accordance with the same production strategy even via the prior art synthetic key intermediate (Japanese Patent Application No. 5-206731) in which the 2'-position is a silyl group, namely which is protected with three silyl groups (cf. Reference Examples 2 and 3 and Examples 64 to 66). Also, it is possible to apply a part (or whole) of the production process when a compound in which the 9-position is protected with an acetyl group is used (cf. Reference Example 4 and Examples 67 to 71). The instant production process can also be effected by protecting a hydroxyl group at the 9-position with an acetal base substituent group.

Firstly, the following describes protection of free hydroxyl group and aldehyde group in a naturally occurring 16-membered macrolide antibiotic leucomycin Fr group [*Journal of Antibiotics*, 28(6), 401 (1975)].

As a first step, a compound represented by the formula (IV) (in this formula, $R^4$ is a straight- or branched-chain aliphatic acyl group having 2 to 5 carbon atoms), namely leucomycin Fr group, is used as a starting material singly or as a mixture of plural components or as a salt thereof, and a hydroxyl group at the 2'-position in the mycaminose (amino sugar) moiety of the starting material is protected with an acetyl group to obtain a compound represented by the formula (XXVI) (in this formula, $R^3$ is an acetyl group and $R^4$ is a straight- or branched-chain aliphatic acyl group having 2 to 5 carbon atoms) in the same manner as described in the above reaction scheme 2. For example, a known compound (41) disclosed in JP-B-53-30718 (a compound of the formula (XXVI) in which $R^3$ is an acetyl group and $R^4$ is a propionyl group) was obtained quantitatively by allowing leucomycin $A_7$ to react with acetic anhydride in dry acetonitrile.

Next, the compound of formula (XXVI) is allowed to react with a necessary or excess amount of a silylating reagent in the presence of a base to obtain a compound represented by the formula (XXVIII) (in this formula, $R^2$ is a hydroxyl group-protecting group such as a silyl protecting group, acetal base protecting group or the like or a substituent group which modifies a hydroxyl group, $R^3$ is an acetyl group or a silyl protecting group, $R^4$ is a straightor branched-chain aliphatic acyl group having 2 to 5 carbon atoms and $R^5$ is a silyl protecting group) or a salt thereof in which a hemiacetal hydroxyl group formed at the 3- and 18-positions and a hydroxyl group at the 9-position are both silylated. For example, a compound (42) (a compound of the formula (XXVIII) in which $R^2$ is a t-butyldimethylsilyl (TBDMS) group, $R^3$ is an acetyl group, $R^4$ is a propionyl group and $R^5$ is a TBDMS group), in which a hemiacetal hydroxyl group formed at the 3- and 18-positions and a hydroxyl group at the 9-position were both t-butyldimethylsilylated, was obtained with a high yield by allowing the compound (41) to react with t-butyldimethylsilyl chloride (TBDMSCl) in dimethylformamide (DMF) in the presence of imidazole. In the structures of the compounds represented by the formulae (VII), (XXVIII), (XXIX), (XXX), (XXXI) and (XXXII) shown in the reaction scheme 4, spatial relative positional relation (context) between the bonding of the hydroxyl group at the 3-position and the carbon atom at the 18-position and the bonding of the hydroxyl group at the 5-position and the carbon atom at the 1'-position is not clear yet.

As described in the foregoing, the production process shown herein can provide a derivative having a free hydroxyl group at the 9-position and another derivative whose hydroxyl group at the same position is modified with a certain substituent group, separately as occasion demands. Hence, production of a synthetic intermediate is effected by introducing the same or different substituent groups into three hydroxyl groups at the 3-, 9- and 2'-positions, excluding the 3"-position, depending on the structure of the compound of interest. For example, in the case of a compound of the formula (XXVIII) in which $R^2$ differs from $R^5$ and is a hydroxyl group-protecting group other than a silyl protecting group or a substituent group which modifies a hydroxyl group, a hydroxyl group at the 9-position of the compound of formula (XXVI) is firstly modified in the same manner as described in Reference Example 4 and Example 67 to obtain a compound represented by the formula (XXVII) (in this formula, $R^2$ is a hydroxyl group-protecting group such as an acetal base protecting group or the like or a substituent group which modifies a hydroxyl group, $R^3$ is an acetyl group and $R^4$ is a straight- or branched-chain aliphatic acyl group having 2 to 5 carbon atoms). Thereafter, a compound of the formula (XXVIII) can be prepared easily by silylating the hemiacetal hydroxyl group formed at the 3- and 18-positions in accordance with the aforementioned reaction with a silylation reagent.

In this connection, a compound of the formula (XXVIII) in which $R^2$ is a silyl protecting group such as a TBDMS group, $R^3$ is a silyl protecting group such as a TBDMS group, $R^4$ is a straight- or branched-chain aliphatic acyl group having 2 to 5 carbon atoms and $R^5$ is a silyl protecting group such as a TBDMS group, for example a compound (62) (a compound of the formula (XXVIII) in which $R^2$ is a TBDMS group, $R^3$ is a TBDMS group, $R^4$ is a propionyl group and $R^5$ is a TBDMS group; EP-A-0 595 303), can be prepared by a single step from a compound represented by the formula (IV) as described in detail in Reference Example 2.

With regard to the stereochemistry of the 18-position when the hemiacetal hydroxyl group formed at the 3- and 18-positions is silylated, one of the diastereoisomers is formed markedly preferentially and formation of the other diastereoisomer at the 18-position as observed in the spiramycin I protection [*Journal of Antibiotics*, 37(7), 750 (1984)] is not significant. On the other hand, there is undeniable possibility of causing by-production of the 18-position diastereoisomer depending on the kind of silyl protecting group to be used and silylation conditions, as well as the kind of the reaction substrate. However, these isomers may or may not be separated in the practice of the production process of the present invention.

With regard to the silyl group to be used for the synthesis of various compounds represented by the formula (XXVIII), not only the TBDMS group but also other silyl groups such as isopropyldimethylsilyl group, ethyldimethylsilyl group and the like may also used, of which isopropyldimethylsilyl group is particularly applicable to the production process of the present invention. As for the silylation reagent for use in the introduction of the TBDMS group, not only TBDMSCl but also other reagent usually used for the introduction of TBDMS into hydroxyl group, such as $TBDMSOClO_3$, $TBDMSOSO_2CF_3$, TBDMSCN and the like, may be used. TBDMSCl may be used preferably in a theoretical or excess amount, more preferably in an equivalent amount or more to the compound of the formula (XXVI). With regard to the base to be used at the time of silylation, not only imidazole but also pyridine, dimethylaminopyridine, lutidine, triethylamine and the like may be used. Preferably, imidazole may be used in a two equivalent or excess amount based on the silylation reagent. In addition to DMF, acetonitrile, methylene chloride, tetrahydrofuran (THF) and the like could be used as the reaction solvent, but excellent results would be obtained more frequently by the reaction in DMF. The protection step progresses with a high yield when the reaction is carried out at a temperature within the range of from 0° to 80° C., preferably 20° to 50° C. for a period of from 1 hour to several days, preferably several hours to 24 hours.

Secondly, a compound represented by the formula (XXIX) (in this formula, $R^2$ is a hydroxyl group-protecting group such as a silyl protecting group, acetal base protecting group or the like or a substituent group which modifies a hydroxyl group, $R^3$ is an acetyl group or a silyl protecting group and $R^5$ is a silyl protecting group) is obtained by selectively and synthetic chemically cleaving an acyl side chain at the 4"-position in the mycarose moiety of a compound which is a typical example of the compounds of formula (XXVIII) in which $R^2$ is a silyl protecting group, $R^3$ is an acetyl group, $R^4$ is a straight- or branched-chain aliphatic acyl group having 2 to 5 carbon atoms and $R^5$ is a silyl protecting group. In the compound represented by the formula (XXVIII), a silyl group is introduced into the hemiacetal hydroxyl group formed at the 3- and 18-positions, the aldehyde group is protected and the 7-membered ring moiety containing them forms a condensed ring with the 16-membered lactone ring. Hence, in comparison with a 16-membered macrolide derivative which has a free hydroxyl group at the 3-position and a free aldehyde group and forms no condensed ring, stability of the lactone ring of the compound of formula (XXVIII) itself under a strongly basic condition is improved sharply. Among compounds represented by the formula (XXVIII), an intermediate in which $R^2$ is a silyl protecting group and $R^3$ is an acetyl group has two acyl groups, and the acetyl group at the 2'-position is indispensable for the subsequent reacylation of a hydroxyl group at the 4"-position and methylthiomethylation of a hydroxyl group at the 3"-position. Thus, it is desirable to preserve the 2'-position acetyl group in removing the 4"-position acyl group. In consequence, the present inventors have examined a possibility of effecting selective deacylation at the 4"-position by a heterogeneous reaction making use of a phase transfer catalyst, because the compound of formula (XXVIII) was particularly fat-soluble, and have succeeded in cleaving the acyl group at the 4"-position in the mycarose moiety selectively and quantitatively.

As an example of the results, a compound (43) (a compound of the formula (XXIX) in which $R^2$ is a TBDMS group, $R^3$ is an acetyl group and $R^5$ is a TBDMS group) was obtained efficiently by dissolving the compound (42) in benzene and mixing the solution with 50% sodium hydroxide aqueous solution vigorously at room temperature in the presence of tetra-n-butylammonium hydrogensulfate. This heterogeneous reaction is carried out by vigorously stirring a mixture consisting of a generally strongly basic water layer and an organic solvent (which does not mix with water uniformly) in which the compound of formula (XXVIII) is dissolved, in the presence of a phase transfer catalyst. The strong base to be dissolved in the water layer may be either sodium hydroxide or potassium hydroxide, and its concentration may preferably be high in general. Examples of the organic solvent which does not mix with water uniformly include benzene, toluene, xylene, n-pentane, n-hexane, cyclohexane, methylene chloride, 1,2-dichloroethane and the like, of which benzene is preferred. Examples of the phase transfer catalyst include tetra-n-butylammonium bromide, tetra-n-butylammonium chloride, benzyltriethylammonium bromide, benzyltriethylammonium chloride, tetra-n-butylammonium hydrogensulfate and the like. The phase transfer catalyst may be used in a catalytically effective amount to several equivalents to the compound of formula (XXVIII), generally in 1 equivalent. The reaction progresses easily at a temperature of from 5° to 40° C. and is completed generally after 10 minutes to several hours, and the mixing efficiency in the reaction system reads to shortened reaction time and improved yield.

Any compound of the leucomycin Fr group may be used as a starting material in the production process of the present invention, but required time for the heterogeneous reaction will be shortened and the yield will be improved slightly when the acyl side chain at the 4"-position in the mycarose moiety is a propionyl group (leucomycin $A_7$) rather than an isovaleryl group (leucomycin $A_1$). In any case, the deacylation reaction of interest may be effected by the heterogeneous reaction independent of the kind of natural type acyl groups as the side chain to be linked to the 4"-position hydroxyl group.

Next, a compound represented by the formula (XXX) whose 4"-position is selectively acylated (in this formula, $R^2$ is a hydroxyl group-protecting group such as a silyl protecting group, acetal base protecting group or the like or a substituent group which modifies a hydroxyl group, $R^3$ is an acetyl group or a silyl protecting group, $R^4$ is a straightor branched-chain aliphatic or aromatic acyl group having 1 to 10 carbon atoms and $R^5$ is a silyl protecting group) or a salt thereof is obtained by allowing the compound of formula (XXIX) to react with a necessary amount of an acylation reagent in the presence of a base. For example, a compound (44) whose 4"-position was selectively normal-valerylated (a compound of formula (XXX) in which $R^2$ is a TBDMS group, $R^3$ is an acetyl group, $R^4$ is a normal valeryl group and $R^5$ is a TBDMS group) was obtained in a high yield by allowing the compound (43) to react with normal valeryl chloride in pyridine.

As an acylation reagent to be used in this step for the introduction of an acyl group into the 4"-position hydroxyl group, any reagent usually used for the acylation of hydroxyl group, such as a saturated fatty acid, an unsaturated fatty acid, an acid halide of an aromatic fatty acid or an acid anhydride thereof, may be used. Preferably, an acid halide may be used in one equivalent or an excess amount. As for the base to be used at the time of the acylation, dimethylaminopyridine, lutidine, triethylamine and the like may be used in addition to pyridine. With regard to the reaction solvent, any solvent usually used for the acylation of hydroxyl group, such as pyridine, DMF, chloroform, methylene chloride, benzene, toluene or the like, may be used, of which pyridine is particularly preferred because it also serves as a base. The reaction is complete in a high yield at a temperature of from 15° to 60° C. for several minutes to 24 hours.

In this instance, when chemical conversion of the acyl side chain at the 4"-position in the mycarose moiety is not required, a series of the above steps for the production of synthetic intermediates represented by the formulae (XXIX) and (XXX) can be omitted.

Thirdly, a methylthiomethyl ether intermediate is prepared as the key compound. As a first step, a hydroxyl group at the 3"-position of the compound of formula (XXX) is methylthiomethylated in accordance with a method reported by a research group of the present applicant [*Journal of Antibiotics*, 33(1), 61(1980)] to obtain a compound represented by the formula (VII) in which $R^2$ is a hydroxyl group-protecting group such as a silyl protecting group, an acetal base protecting group or the like or a substituent group which modifies a hydroxyl group, $R^3$ is an acetyl group or a silyl protecting group, $R^4$ is a straight- or branched-chain aliphatic or aromatic acyl group having 1 to 10 carbon atoms and $R^5$ is a silyl protecting group. The same reaction conditions as described in the above reaction scheme 2 can be used. As an example, a compound (45) (a compound of formula (VII) in which $R^2$ is a TBDMS group, $R^3$ is an acetyl group, $R^4$ is a normal valeryl group and $R^5$ is a TBDMS group) was synthesized by allowing the compound (44) to react with DMSO and acetic anhydride.

Next, the acetyl group linked to the hydroxyl group at the 2'-position of the compound of formula (VII) is deprotected to obtain a key compound represented by the formula (XXXI) (in this formula, $R^2$ is a hydroxyl group-protecting group such as a silyl protecting group, an acetal base protecting group or the like or a substituent group which modifies a hydroxyl group, $R^4$ is a straight- or branched-chain aliphatic or aromatic acyl group having 1 to 10 carbon atoms and $R^5$ is a silyl protecting group), namely a methylthiomethyl ether synthetic intermediate, with a quantitative yield in the same manner as described in the above reaction scheme 2. For example, a compound (46) (a compound of the formula (XXXI) in which $R^2$ is a TBDMS group, $R^4$ is a normal valeryl group and $R^5$ is a TBDMS group) was obtained by allowing the compound (45) to react in methanol.

Fourthly, the methylthiomethyl group introduced into the tertiary hydroxyl group at the 3"-position in a neutral sugar moiety of the key intermediate represented by formula (XXXI) is selectively reduced in the same manner as described in the above reaction scheme 2, thereby efficiently synthesizing a 16-membered macrolide derivative whose tertiary hydroxyl group at the 3"-position is methylated. Methodology for the catalytic reduction of the methylthiomethylated hydroxyl group into a methoxy group and various problems concerning application of the method to the synthesis of 16-membered macrolide derivatives have been described in the foregoing in detail and therefore are omitted herein. Similarly, control of the activity of metal catalysts to be used in the selective reduction reaction and the like are also not described herein.

A compound represented by the formula (XXXII) (in this formula, $R^2$ is a hydroxyl group-protecting group such as a silyl protecting group, an acetal base protecting group or the like or a substituent group which modifies a hydroxyl group, $R^4$ is a straight- or branched-chain aliphatic or aromatic acyl group having 1 to 10 carbon atoms and $R^5$ is a silyl protecting group) is selectively synthesized using Raney nickel whose activity is controlled at a proper level, by chemically converting the methylthiomethylated tertiary hydroxyl group at the 3"-position into a methoxy group without causing reduction of double bond in the compound represented by formula (XXXI). For example, a compound (47) (a compound of the formula (XXXII) in which $R^2$ is a TBDMS group, $R^4$ is a normal valeryl group and $R^5$ is a TBDMS group) was selectively synthesized by stirring the compound (46), for a short period at room temperature, in ethanol together with Raney nickel whose activity was controlled at a proper level. This selective reduction reaction progresses efficiently also when a hydroxyl group at the 9-position is modified with a substituent group other than silyl groups, such as the case of a compound (69) (a compound of the formula (XXXI) in which $R^2$ is an acetyl group, $R^4$ is a propionyl group and $R^5$ is a TBDMS group) (cf. Example 70).

When a compound (57) (a compound of the formula (XXXII) in which $R^2$ is a TBDMS group, $R^4$ is an isovaleryl group and $R^5$ is a TBDMS group) is produced from a compound (65) (a compound of the formula (VII) in which $R^2$ is a TBDMS group, $R^3$ is a TBDMS group, $R^4$ is an isovaleryl group and $R^5$ is a TBDMS group), the compound (65) is subjected to reduction using Raney nickel and then the TBDMS group linked to the hydroxyl group at the 2'-position in the mycaminose moiety is selectively deprotected in accordance with the procedure disclosed in the prior application (EP-A-0 595 303) (cf. Example 66).

Finally, the following describes deprotection of two silyl groups linked to a hemiacetal hydroxyl group formed at the 3- and 18-positions and to a hydroxyl group at the 9-position. These silyl groups such as TBDMS groups can be deprotected completely or partially by their reaction with a tetra-n-butylammonium fluoride (TBAF) reagent or a certain acid or under known deprotection conditions related to hydroxyl group-linking silyl ethers (Theodora W. Greene and Peter G. M. Wuts, *Protective Groups in Organic Synthesis*, 2nd ed., Wiley: New York, 1991). Examination of the effectiveness of various desilylation reaction reagents using a compound of the formula (XXXII) as a reaction substrate revealed that good results can be obtained when the deprotection reaction is carried out using TBAF. In fact, a compound of the formula (XXXII) whose $R^2$ and $R^5$ are both TBDMS group can be chemically converted into the final compound of interest represented by the formula (VIII) when deprotection is carried out using TBAF. For example, a compound (48) (a compound of the formula (VIII) in which $R^2$ is a hydrogen atom and $R^4$ is a normal valeryl group) was obtained as the main product by allowing a compound (47) to react with excess amount of TBAF in THF under heating condition.

When the two silyl groups such as TBDMS groups are deprotected using TBAF, completion of the reaction can be quickened and side reactions can be prevented completely by carrying out the reaction in such a manner that the reaction system is not contaminated with water. In this instance, since TBAF reacts with free aldehyde groups as a strong base, it is necessary to take care of the after-treatment of the reaction in order to complete the deprotection step in a high yield, which will be described later in EXAMPLES in detail. Not only ether solvents but also halogen base solvents, nitrile base solvents and the like may be used as the reaction solvent in the TBAF-aided deprotection, though good results are frequently obtained when THF is used. In addition, concentration of TBAF itself in the reaction solvent can act as an important factor for the completion of this reaction. That is, when the equivalent ratio of TBAF to the reaction substrate is set to a constant level, the reaction cannot be completed easily if the concentration of TBAF in the reaction substrate is too low (too many reaction solvent) or too high (too small reaction solvent). In general, the reaction progresses efficiently at a concentration of from 0.5 to 4M, preferably from 1 to 2M. TBAF may be used in an amount of from 2 to more excess equivalents, and complete and quick deprotection may be attained when 10 or more equivalents of TBAF is used. The reaction can be carried out at 0° to 25° C. for one to several hours.

In this instance, novel and useful substances can be created based on the present invention by selectively acylating a hydroxyl group at the 9- or 2'-position of the compound represented by the formula (VIII) or a salt thereof in accordance with a known method [*Hakko to Kogyo*, 37(12), 1171 (1979)], by subjecting the hydroxyl group at the 9-position of the compound to allylic rearrangement into the 11- or 13-position in the presence of a dilute acid in accordance with a known method [*Chemical and Pharmaceutical Bulletin*, 18(8), 1501 (1970); *Scientific Report of Meiji Seika Kaisha*, 12, 85 (1972); and *Journal of Antibiotics*, 35(11), 1521 (1982)] or by selectively oxidizing the hydroxyl group at the 9-position in accordance with a known method [*Journal of Antibiotics*, 24(8), 526 (1971)]. As an example, a compound (71) (a compound of the formula (I) in which $R^1$ is a hydrogen atom, $R^2$ is a propionyl group, $R^3$ is a hydrogen atom and $R^4$ is a propionyl group) was synthesized by selectively propionylating a hydroxyl group at the 9-position of a compound (2) (a compound of the formula (VIII) in which $R^2$ is a hydrogen atom and $R^4$ is a propionyl group) in accordance with a known method (JP-A-48-13380) (cf. Example 72). The compound (71) can also be produced in accordance with the synthetic method shown in Examples 67 to 71 in which a 9-O-acyl intermediate is used.

The compounds of the present invention may be in the form of a pharmaceutically acceptable inorganic or organic salt. Examples of the salts include a salt of inorganic acid such as hydrochloric acid, sulfuric acid, nitric acid, phosphoric acid and a salt of organic acid such as acetic acid, stearic acid, malic acid and succinic acid.

The effect of the first aspect of the present invention resides in the creation of a novel and useful 16-membered macrolide derivative. Antimicrobial activities of the compounds of the present invention were determined by measuring minimum inhibitory concentration (MIC). Minimum inhibitory concentration was determined by the agar plate dilution method in the following manner.

Test strains were subjected to seed culture using Sensitivity test broth (STB, Nissui Pharmaceutical) except that the strains belonging to the genus Streptococcus, Branhamella and Haemophilus were cultured on blood agar plate. A 5 μl portion of cell suspension of the test strains having about $10^6$ CFU/ml was inoculated into Sensitivity disk agar (SDA, Nissui Pharmaceutical) supplemented with 5% horse blood and incubated at 37° C. for 20 hours. Then, MIC was measured. Among compounds of the formula (I) obtained by the present invention, for example, compounds (1), (2), (3) and (4), are by themselves possessed of strong antimicrobial activities on clinically important Gram-positive bacteria and Mycoplasma. Antimicrobial activities in vitro of the compounds (1) and (2) are shown in Table 1, and those of the compounds (3) and (4) in Table 3. Each of the compounds (1) and (2), in which the 9-position is an $sp^3$ carbon and, at the same time, the tertiary hydroxyl group at the 3"-position is methylated and the hydroxyl group at the 4"-position is acylated, showed twice as high antimicrobial activities in vitro against most of test strains as corresponding compounds whose tertiary hydroxyl group at the 3"-position is in the free form, namely midecamycin $A_1$ (medemycin, MDM) and leucomycin $A_7$ (LM-$A_7$) [*Journal of Antibiotics*, Ser. A, 20(4), 234 (1967)]. Particularly, the compounds (1) and (2) have considerably improved antimicrobial activity against *Streptococcus pneumoniae* which is one of the clinically important bacteria which cause upper respiratory tract infection.

For the purpose of comparing the antimicrobial activities in vitro of the compounds obtained by the present invention with those of excellent macrolide antimicrobial agents, antimicrobial activities of rokitamycin (RKM) [*Journal of Antibiotics*, 34(8), 1001 (1981)] and clarithromycin (CAM) are shown in Table 2 (measured simultaneously with the compound (2)). MIC values of the compound (2) of the present invention were generally excellent except for a Gram-negative bacterium (*Branhamella catarrhalis*), even in comparison with rokitamycin which belongs to a group of the most strong antimicrobial activities in vitro among commercially available 16-membered macrolide antibiotics (pharmaceutical preparations). When compared with clarithromycin which is a 14-membered new macrolide, the compound (2) showed a definitely superior antimicrobial activity in vitro on a drug-resistant strain of Staphylococcus and comparable or slightly superior activities against *Enterococcus feacalis* and *Haemophilus influenzae*, though its activity on *Branhamella catarrhalis* was inferior to that of clarithromycin. Thus, it was confirmed that the compound (2) of the present invention belongs to a group of macrolide derivatives having most excellent antimicrobial activities against Gram-positive bacteria.

Other compounds of the present invention represented by the formulae (XIX) and (XX) are also possessed of excellent antimicrobial activities against Gram-positive bacteria. Among compounds represented by the formula (XIX), each of compounds (5) and (11), whose hydroxyl group at the 9-position is acetylated, shows antimicrobial activities in vitro comparable to or higher than those of an excellent 16-membered macrolide antimicrobial agent, miokamycin (MOM) [*Journal of Antibiotics*, 29(5), 536 (1976)]. Antimicrobial activity of the compound (11) against *Branhamella catarrhalis* is slightly superior to that of the compound (5). On the other hand, compounds (16H) and (16L) whose respective hydroxyl group at the 9-position of the lactone ring is 1-ethoxyethylated are possessed of antimicrobial activities though inferior to those of the compound (1) whose corresponding hydroxyl group at the 9-position of the lactone ring is in the free form.

Certain derivatives among compounds of the present invention represented by the formula (VI) are possessed of markedly excellent antimicrobial activities against clinically important Gram-positive bacteria and the like. As an illustrative example of the compounds represented by the formula (VI), antimicrobial activities of a compound (33) in which hydroxyl groups at the 3- and 9-positions are in the free form and a hydroxyl group at the 4"-position is substituted with a normal butyryl group were measured simultaneously with those of rokitamycin and clarithromycin. The results are shown in Table 4. In comparison with rokitamycin, a compound (33) chemically derived from leucomycin A$_5$ is possessed of markedly excellent antimicrobial activities in vitro. In addition, this compound shows generally improved antimicrobial activities even in comparison with the compound (2) which is one of the best leucomycin derivatives having superior antimicrobial activities, and its outstanding antimicrobial activities are completely comparable to those of clarithromycin which has the most excellent antimicrobial activities among new macrolide antibiotics. Very little actually is known in the world about a 16-membered macrolide derivative which has the same level of antimicrobial activities of clarithromycin.

Each of compounds (48), (53) and (58) represented by the formula (VIII) is also possessed of markedly strong microbial activities against clinically important Gram-positive bacteria and the like. Simultaneously measured antimicrobial activities of these three inventive compounds and comparative rokitamycin and miokamycin are shown in Table 5. As is evident from the table, these compounds, especially (48) and (53), show markedly excellent antimicrobial activities in comparison with rokitamycin. To date, no information is available concerning a leucomycin derivative whose structure is similar to the compound (48) in which a non-natural type acyl side chain is introduced into a hydroxyl group at the 4"-position in the mycarose moiety and a hydroxyl group at the 3"-position is methylated. In consequence, development of these novel compounds rendered possible, through studies on their biochemical evaluation, not only creation of novel substances having strong activities but also provision of important information useful for the elucidation of correlations between structures and activities of 16-membered macrolide derivatives and between their structures and pharmacokinetics. In fact, the compound (48) which has a non-natural acyl side chain and the compound (53) which can hardly be-obtained by chemical synthesis without the use of the production process of the present invention are possessed of slightly superior antimicrobial activities to the compound (58) that has a natural type acyl side chain.

Next, antimicrobial activities of the compounds (3) and (4) are shown in Table 3 as well as those of midecamycin M$_1$ (MDM-M$_1$) [*Journal of Bacteriology*, 174(15), 5141 (1992); and JP-A-48-10288] and leucomycin V (LM-V) [*Journal of Antibiotics*, 28(6), 401 (1975)] for comparison. Each of the compounds (3) and (4), in which the 9-position is an sp$^3$ carbon and, at the same time, the tertiary hydroxyl group at the 3"-position is methylated and the hydroxyl group at the 4"-position is in the free form, is possessed of strong antimicrobial activities, and their MIC values obtained against most of the test strains are improved two to three times in comparison with corresponding compounds whose tertiary hydroxyl group at the 3"-position is in the free form, namely midecamycin M$_1$ and leucomycin V.

It is a matter of course that, in order to gain excellent clinical results of an oral antimicrobial agent, not only it should have superior antimicrobial activities in vitro but also ADME of the drug, its actual pharmacokinetics and the like should exert no small influences on the clinical effects. In this connection, it has been reported that complex metabolism progresses after oral administration of a drug into the living body and, though the metabolic pattern differs depending on the living species, an acyl group of a neutral sugar moiety of the administered drug is cleaved with time and antimicrobial activities of the drug itself therefore is reduced gradually, even in the case of miokamycin and rokitamycin which are 16-membered macrolide antimicrobial agents whose clinical therapeutic effects are superior to natural counterpart compounds [*Yakugaku Zasshi*, 102(8), 781 (1982); and Symposium on novel drugs IV, TMS-19-Q, p.109, 31st General Meeting of the Society of Japan Chemotherapy].

Supposing that the acyl group linked to the hydroxyl group at the 4"-position is cleaved during metabolism of the compounds represented by formulae (XI) and (XII) similar to miokamycin and rokitamycin as reported, it is presumable that the compounds represented by formulae (XIII) and (XIV) will be formed respectively as their metabolites, though there are no reports on the metabolism of a 16-membered macrolide derivative whose tertiary hydroxyl group at the 3"-position is methylated and, at the same time, whose hydroxyl group at the 4"-position is acylated. In other words, when it is assumed that a neutral sugar moiety of the compound (2) is deacylated at the 4"-position during metabolism similar to the case of other 16-membered macrolide derivatives, antimicrobial activities in vitro of the unmetabolized compound (2) are slightly superior to those of rokitamycin, and antimicrobial activities of the compound (4) which is presumed to be the final metabolite of the neutral sugar moiety of the compound (2) are 4 to 8 times as high as those of leucomycin V which is the final metabolite of rokitamycin. This simply suggests the outstanding infection-treating effects of the compound (2). Even if the compound (2) would not receive such a metabolism, its excellent antimicrobial activities would continue in vivo for a relatively prolonged period of time with no particular problems.

TABLE 1

| | Antimicrobial activity (MIC: µg/ml) | | | |
| --- | --- | --- | --- | --- |
| | Compound | Compound | Comparison | |
| Test strain | (1) | (2) | MDM | LM-A$_7$ |
| S. aureus 209P JC-1 | 0.20 | 0.10 | 0.39 | 0.10 |
| S. aureus M133 | 0.39 | 0.20 | 0.78 | 0.39 |
| S. aureus M126 | >100 | >100 | >100 | >100 |
| S. aureus MS15009/pMS99 | >100 | >100 | >100 | >100 |
| S. aureus MS15026 | >100 | >100 | >100 | >100 |
| S. aureus MS15009/pMS98 | 0.20 | 0.20 | 0.39 | 0.20 |
| S. aureus MS15027 | 0.39 | 0.20 | 0.78 | 0.39 |
| S. epidermidis ATCC14990 | 0.78 | 0.20 | 0.78 | 0.39 |
| M. luteus ATCC9341 | 0.05 | <0.025 | 0.05 | 0.05 |
| E. faecalis W-73 | 1.56 | 0.39 | 3.13 | 0.78 |
| E. coli NIHJ JC-2 | >100 | >100 | >100 | >100 |
| K. pneumoniae PCI602 | >100 | >100 | >100 | >100 |
| S. pneumoniae IP692 | 0.10 | <0.025 | 0.39 | 0.10 |
| S. pneumoniae Type 1 | 0.10 | 0.05 | 0.39 | 0.20 |
| S. pyogenes Cook | 0.10 | 0.05 | 0.20 | 0.10 |
| B. catarrhalis W-0500 | 0.78 | 0.39 | 3.13 | 0.78 |
| B. catarrhalis W-0506 | 0.78 | 0.78 | 3.13 | 0.78 |
| H. influenzae 9334 | 1.56 | 0.78 | 6.25 | 0.78 |
| H. influenzae Type b | 12.5 | 6.25 | 25 | 6.25 |

TABLE 2

| Test strain | Antimicrobial activity (MIC: μg/ml) Comparison | |
|---|---|---|
| | RKM | CAM |
| S. aureus 209P JC-1 | 0.10 | 0.10 |
| S. aureus M133 | 0.39 | 1.56 |
| S. aureus M126 | >100 | >100 |
| S. aureus MS15009/pMS99 | >100 | >100 |
| S. aureus MS15026 | >100 | >100 |
| S. aureus MS15009/pMS98 | 0.39 | >100 |
| S. aureus MS15027 | 0.78 | 1.56 |
| S. epidermidis ATCC14990 | 0.78 | 0.10 |
| M. luteus ATCC9341 | 0.05 | <0.025 |
| E. faecalis W-73 | 0.39 | 0.78 |
| E. coli NIHJ JC-2 | >100 | 100 |
| K. pneumoniae PCI602 | >100 | 100 |
| S. pneumoniae IP692 | 0.10 | <0.025 |
| S. pneumoniae Type 1 | 0.10 | <0.025 |
| S. pyogenes Cook | 0.05 | <0.025 |
| B. catarrhalis W-0500 | 0.20 | 0.20 |
| B. catarrhalis W-0506 | 0.20 | 0.20 |
| H. influenzae 9334 | 1.56 | 1.56 |
| H. influenzae Type b | 6.25 | 6.25 |

TABLE 3

| Test strain | Antimicrobial activity (MIC: μg/ml) | | | |
|---|---|---|---|---|
| | Compound (3) | Compound (4) | Comparison MDM-M₁ | LM-A₇ |
| S. aureus 209P JC-1 | 0.39 | 0.39 | 6.25 | 1.56 |
| S. aureus M133 | 1.56 | 0.78 | 12.5 | 6.25 |
| S. aureus M126 | >100 | >100 | >100 | >100 |
| S. aureus MS15009/pMS99 | >100 | >100 | >100 | >100 |
| S. aureus MS15026 | >100 | >100 | >100 | >100 |
| S. aureus MS15009/pMS98 | 0.78 | 0.39 | 6.25 | 3.13 |
| S. aureus MS15027 | 0.78 | 0.78 | 6.25 | 3.13 |
| S. epidermidis ATCC14990 | 1.56 | 0.78 | 12.5 | 3.13 |
| M. luteus ATCC9341 | 0.10 | 0.05 | 0.39 | 0.20 |
| E. faecalis W-73 | 0.78 | 0.78 | 12.5 | 6.25 |
| E. coli NIHJ JC-2 | >100 | >100 | >100 | >100 |
| K. pneumoniae PCI602 | >100 | >100 | >100 | >100 |
| S. pneumoniae IP692 | 0.10 | 0.10 | 0.78 | 0.39 |
| S. pneumoniae Type 1 | 0.10 | 0.05 | 0.78 | 0.39 |
| S. pyogenes Cook | 0.20 | 0.10 | 1.56 | 0.39 |
| B. catarrhalis W-0500 | 3.13 | 1.56 | 25 | 12.5 |
| B. catarrhalis W-0506 | 3.13 | 1.56 | 25 | 12.5 |
| H. influenzae 9334 | 12.5 | 1.56 | 100 | 12.5 |
| H. influenzae Type b | 50 | 12.5 | 100 | 50 |

TABLE 4

| Test strain | Antimicrobial activity (MIC: μg/ml) | | |
|---|---|---|---|
| | Compound (33) | Comparison RKM | CAM |
| S. aureus 209P JC-1 | 0.05 | 0.20 | 0.05 |
| S. aureus M133 | 0.20 | 0.78 | >100 |
| S. aureus M126 | >100 | >100 | >100 |
| S. aureus MS15009/pMS99 | >100 | >100 | >100 |
| S. aureus MS15026 | >100 | >100 | >100 |
| S. aureus MS15009/pMS98 | 0.10 | 0.78 | >100 |
| S. aureus MS15027 | 0.20 | 0.78 | >100 |
| S. epidermidis ATCC14990 | 0.20 | 0.78 | 0.10 |
| M. luteus ATCC9341 | <0.025 | 0.05 | <0.025 |
| E. faecalis W-73 | 0.78 | 1.56 | 0.78 |
| E. coli NIHJ JC-2 | >100 | >100 | 50 |
| K. pneumoniae PCI602 | 100 | >100 | 50 |
| S. pneumoniae IP692 | <0.025 | 0.20 | <0.025 |
| S. pneumoniae Type 1 | <0.025 | 0.20 | <0.025 |
| S. pyogenes Cook | <0.025 | 0.20 | <0.025 |
| B. catarrhalis W-0400 | 0.10 | 0.39 | 0.10 |
| B. catarrhalis W-0506 | 0.20 | 0.78 | 0.10 |
| H. influenzae 9334 | 0.20 | 6.25 | 1.56 |
| H. influenzae Type b | 1.56 | 12.5 | 6.25 |

TABLE 5

| Test strain | Antimicrobial activity (MIC: μg/ml) | | |
|---|---|---|---|
| | Compound (48) | Compound (53) | Compound (58) |
| S. aureus 209P JC-1 | 0.05 | 0.05 | 0.05 |
| S. aureus M133 | 0.20 | 0.20 | 0.39 |
| S. aureus M126 | >100 | >100 | >100 |
| S. aureus MS15009/pMS99 | >100 | >100 | >100 |
| S. aureus MS15026 | >100 | >100 | >100 |
| S. aureus MS15009/pMS98 | 0.20 | 0.20 | 0.20 |
| S. aureus MS15027 | 0.20 | 0.20 | 0.20 |
| S. epidermidis ATCC14990 | 0.20 | 0.20 | 0.20 |
| M. luteus ATCC9341 | <0.025 | <0.025 | <0.025 |
| E. faecalis W-73 | 0.78 | 0.78 | 0.78 |
| E. coli NIHJ JC-2 | >100 | >100 | >100 |
| K. pneumoniae PCI602 | >100 | >100 | >100 |
| S. pneumoniae IP692 | <0.025 | <0.025 | 0.05 |
| S. pneumoniae Type 1 | <0.025 | <0.025 | 0.05 |
| S. pyogenes Cook | <0.025 | <0.025 | 0.05 |
| B. catarrhalis W-0500 | 0.10 | 0.20 | 0.20 |
| B. catarrhalis W-0506 | 0.20 | 0.20 | 0.20 |
| H. influenzae 9334 | 0.78 | 0.39 | 0.78 |
| H. influenzae Type b | 6.25 | 6.25 | 6.25 |

| Test strain | Antimicrobial activity (MIC: μg/ml) Comparison | |
|---|---|---|
| | MOM | RKM |
| S. aureus 209P JC-1 | 0.39 | 0.20 |
| S. aureus M133 | 0.78 | 0.78 |
| S. aureus M126 | >100 | >100 |
| S. aureus MS15009/pMS99 | >100 | >100 |
| S. aureus MS15026 | >100 | >100 |
| S. aureus MS15009/pMS98 | 0.78 | 0.78 |
| S. aureus MS15027 | 0.78 | 0.78 |
| S. epidermidis ATCC14990 | 0.78 | 0.78 |
| M. luteus ATCC9341 | 0.10 | 0.05 |
| E. faecalis W-73 | 6.25 | 1.56 |
| E. coli NIHJ JC-2 | >100 | >100 |
| K. pneumoniae PCI602 | >100 | >100 |
| S. pneumoniae IP692 | 0.20 | 0.20 |
| S. pneumoniae Type 1 | 0.20 | 0.20 |
| S. pyogenes Cook | 0.20 | 0.10 |
| B. catarrhalls W-0500 | 1.56 | 0.78 |
| B. catarrhalis W-0506 | 1.56 | 0.39 |
| H. influenzae 9334 | 6.25 | 6.25 |
| H. influenzae Type b | 50 | 12.5 |

The compounds represented by the formula (I) exert excellent in vivo effects in infection-treating tests in mice in comparison with the case of currently known 16-membered macrolide antimicrobial agents. For example, in an infection-treating test in mice in which a pneumococcus strain *Streptococcus pneumoniae* DP-1 Type 1 is used, a compound (5) as one of the compounds of the formula (I) showed a coordinate infection-treating effect with a 1/4 or less amount of miokamycin and a 1/8 or less amount of rokitamycin. Such an excellent effect is related not to the ester bonding of the tertiary hydroxyl group at the 3"-position with an acyl group but directly to its ether bonding with a methyl group. In other words, the superior antimicrobial activities of one of the presumed in vivo metabolites of the compound (5), namely 3"-O-methylmidecamycin $M_1$ (3"-O-methyl-3-O-propionylleucomycin V), in comparison with the activities of midecamycin $M_1$ [*Journal of Bacteriology*, 174(15), 5141 (1992); and JP-A-48-10288] as a corresponding substance of miokamycin seem to be a factor of such outstanding in vivo effects. In this connection, it has been reported that an isovaleryl group linked to a hydroxyl group at the 4"-position cannot easily be cleaved in rat blood plasma when compared with a propionyl group [*Yakugaku Zasshi*, 102(8), 781 (1982)]. Hence, in vivo effects comparable to or higher than those of the compound (5) can be expected when a compound (11) or the like of the present invention is subjected to the infection-treating test in mice.

On the other hand, compounds (5), (6) and (39) obtained respectively from the compounds (1), (2) and (33) by acetylating each hydroxyl group at the 9-position of a lactone ring and a compound (40) obtained from the compound (33) by propionylating the same are possessed of strong antimicrobial activities by themselves though slightly lower than those of their starting materials (1), (2) and (33).

As has been described above, it was revealed for the first time that antimicrobial activities in vitro against various bacteria, especially against *Streptococcus pneumoniae*, of 16-membered macrolide derivatives of midecamycins and leucomycins can be improved by methylating the tertiary hydroxyl group at the 3"-position. That is, various derivatives represented by the formula (I) having excellent antimicrobial activities were created by developing a derivative-synthesizing strategy which has been constructed based on the chemical structure of L-chladinose, a constituent sugar of erythromycin, on the basis of the information obtained from the correlation between structures and activities of 16-membered macrolide compounds.

The effect of the second aspect of the present invention resides in a novel production process by which a compound represented by the formula (III) is obtained efficiently through 4 to 6 steps using a known naturally occurring 16-membered macrolide antibiotic represented by the formula (II) as a starting material, via a 3"-O-methylthiomethyl synthetic intermediate without a glycosylation reaction. For example, when the compound (5) of the present invention was prepared using midecamycin $A_3$ and erythromycin as starting materials, the process required 9 steps of chemical reactions including glycosylation and 1 microbial conversion step, but the total yield from midecamycin $A_3$ was less than 5% at the best. On the contrary, the novel production process of the present invention has enabled synthesis of the compound (5) in a total yield of about 20% using medemycin as a starting material.

In addition, a general method was provided which is useful in indirectly introducing a methyl group under mild reaction conditions into a tertiary hydroxyl group in a compound having poor chemical stability. The reaction itself for the conversion of a methylthiomethyl etherificated hydroxyl group into a methoxy group has already been known as described in the foregoing [*Carbohydrate Research*, 7, 474 (1968)], but little is known about application of this chemical conversion reaction to tertiary hydroxyl groups. Moreover, very little actually has been reported on the application of this reaction to a compound which contains a functional group such as double bond, a free aldehyde group or the like that shows high reactivity under a catalytic reduction condition.

Also provided is a protecting group which is useful in the studies of derivatives of 16-membered macrolide antibiotics for the efficient protection of a hydroxyl group at the 9-position of a lactone ring. When an excellent derivative is produced by chemical reactions using a naturally occurring compound as a starting material, it is necessary in general to protect a specific functional group such as an amino group, a hydroxyl group or the like. Very little actually has been known about the use of an efficient protecting group for a hydroxyl group at the 9-position in the synthetic chemical studies of derivatives of 16-membered macrolide compounds. The present inventors have confirmed that a certain acetal base protecting group having an asymmetric carbon atom, especially 1-ethoxyethyl group, is possessed of sufficient characteristics as a protecting group.

The effect of the third aspect of the present invention resides in a novel production process by which a compound of the present invention whose hydroxyl group at the 3-position of a lactone ring is in the free form, namely one of the compounds represented by the formula (VI) in which $R^1$ is a hydrogen atom, or an analogue thereof, is obtained through 6 or less steps using a known naturally occurring 16-membered macrolide antibiotic represented by the formula (IV) as a starting material via a 3"-O-methylthiomethyl synthetic intermediate, without using a glycosylation reaction and 3,18-hemiacetal-18-O-silyl synthetic intermediate. A 16-membered macrolide derivative in which a hydroxyl group at the 3-position of a lactone ring is in the free form and, at the same time, a hydroxyl group at the 3"-position of a neutral sugar moiety is methylated can be prepared by pure synthetic chemical means for the first time making use of this inventive production process.

Also provided is a protecting group which is useful for the efficient protection of a hydroxyl group at the 3-position of a lactone ring, in the studies of derivatives of leucomycins, excluding spiramycins, in which an $sp^3$ carbon is located at the 9-position of a lactone ring. When an excellent derivative is produced by chemical reactions using a naturally occurring compound as a starting material, it is necessary in general to protect a specific functional group such as an amino group, a hydroxyl group or the like. In the synthetic chemical studies of derivatives of 16-membered macrolide compounds, an acetal base substituent group having an asymmetric carbon atom has been applied only to tylosins and spiramycins as a protecting group of a hydroxyl group at the 3-position. Applicability of this substituent group as a protecting group has been limited because isomerization of molecules occurs in a compound whose hydroxyl group at the 9-position of a lactone ring is in the free form, due to the presence of the allyl-position (9-position) hydroxyl group, when said protection group is introduced into a hydroxyl group at the 3-position of a lactone ring in the presence of an acid catalyst. The present inventors have confirmed that a certain acetal base protecting group having an asymmetric carbon atom, especially 1-ethoxyethyl group, is possessed of sufficient characteristics as a protecting group of a hydroxyl group at the 3-position in a lactone ring of a 16-membered macrolide compound whose hydroxyl group at the 9-position in a lactone ring is in the free form.

The effect of the fourth aspect of the present invention resides in the provision of a novel production process by which a novel 16-membered macrolide derivative represented by the formula (VIII) is obtained by pure synthetic chemical means using a known naturally occurring 16-membered macrolide antibiotic represented by the formula (IV) as a starting material without employing a glycosylation reaction. This novel production process has enabled indirect introduction of a methyl group under mild reaction conditions into a tertiary hydroxyl group which exists in a compound having poor chemical stability and, at the same time, production of said novel 16-membered macrolide derivative which contains any desired natural or non-natural type acyl side chain at the 4"-position. In other words, this novel production process provides not only a methodology for the introduction of a methyl group into a tertiary hydroxyl group of the mycarose moiety but also a drastic chemical conversion method in which a hydroxyl group at the 4"-position in a neutral sugar moiety is acylated after a selective deacylation reaction. In consequence, a novel 16-membered macrolide derivative having a totally new structure whose hydroxyl group at the 4"-position in the mycarose moiety is modified can be created making use of this novel production process.

The 16-membered macrolide derivatives may be formulated into antimicrobial pharmaceutical compositions together with known pharmaceutically acceptable carriers.

The following Examples and Reference Examples are provided to further illustrate the present invention in detail, but are not to be construed to limit the scope of the present invention.

EXAMPLE 1

Process for producing compound (1) [a compound represented by the formula (I) wherein $R^1$ represents a propionyl group, $R^2$ represents a hydrogen atom, $R^3$ represents a hydrogen atom and $R^4$ represents a propionyl group] (3"-O-methylmidecamycin $A_1$):

A medium comprising 2.0% of glucose, 1.0% of polypeptone, 0.05% of dipotassium hydrogenphosphate, 0.05% of magnesium sulfate heptahydrate and 0.3% of sodium chloride was adjusted to pH 7.0 and sterilized prior to the use. The above-mentioned medium was pipetted in 100 ml portions into forty 500 ml-Erlenmeyer's flasks and sterilized at 120° C. for 30 minutes. The medium in each flask was inoculated with 2.0 ml of a frozen seed of *Streptomyces mycarofaciens* SF2772 strain having a cell density of 10 to 15% which was then incubated therein at 28° C. for 24 hours under shaking. Next, 60 ml of a methanol solution containing 472 mg of a compound represented by the formula (X), wherein $R^1$ represents a propionyl group and $R^4$ represents an propionyl group (3"-O-methylmidecamycin $A_3$), was added to each flask in 1.5 ml portions and the incubation was continued at 28° C. for 20 hours under shaking. After the completion of the incubation, the culture was centrifuged at 3000 rpm for 10 minutes. Thus 3.5 liters of a transparent culture supernatant was obtained while the solid matters including the cells were removed. To the solid matters was added 2.0 liters of water and the mixture was stirred followed by centrifugation. The washing liquor thus obtained was combined with the above-mentioned transparent culture supernatant. After adjusting the mixture to pH 9, the conversion product was extracted with 5.5 liters of ethyl acetate and then with 2.8 liters of ethyl acetate twice. The ethyl acetate layer was dried over anhydrous sodium sulfate and then filtered. The filtrate was concentrated under reduced pressure and the residue thus obtained was purified by preparative TLC [developing system: chloroform/methanol (10:1)]. Thus 321 mg of a crude compound (1) was obtained. This crude product was purified by Sephadex LH-20 column chromatography (bed volume: 1.0 liter, methanol) to thereby give 223 mg of the compound (1).

Physicochemical properties of the compound (1)

(1) Color and appearance: colorless solid.

(2) Molecular formula: $C_{42}H_{69}NO_{15}$.

(3) Mass spectrum (SIMS): m/z 828 (M+H)$^+$.

(4) Specific rotation: $[\alpha]_D^{15}$ −65° (c 1.0, $CH_3OH$).

(5) m.p.: melting at around 116° to 120° C. without showing any definite melting point.

(6) $^1$H NMR spectrum (400 MHz, $CDCl_3$) δ (ppm: 2.24 (br d, 2-H), 2.76 (dd, 2-H), 5.14 (br d, 3-H), 3.26 (br d, 4-H), 3.57 (s, 4-$OCH_3$), 3.88 (br d, 5-H), 0.92 (br ddd, 7-H), 1.54 (br dt, 7-H), 1.89 (m, 8-H), 4.07 (dd, 9-H), 5.61 (dd, 10-H), 6.67 (dd, 11-H), 6.08 (br dd, 12-H), 5.79 (ddd, 13-H), 2.15 (dt, 14-H), 5.03 (ddq, 15-H), 1.26 (d, 16-$H_3$), 2.32 (br dd, 17-H), 2.86 (br dd, 17-H), 9.63 (br s, 18-H), 0.98 (d, 19-$H_3$), 2.51 (dq, 3-$OCOCH_2CH_3$), 2.64 (dq, 3-$OCOCH_2CH_3$), 1.22 (t, 3-$OCOCH_2\underline{CH_3}$), 4.52 (d, 1'-H), 3.22 (dd, $\overline{2'}$-H), 2.42 (t, 3'-H), 3.44 (t, 4'-$\overline{H}$), 3.29 (dq, 5'-H), 1.16 (d, 6'-$H_3$), 2.57 (s, 3'-N($CH_3)_2$), 4.92 (d, 1"-H), 1.66 (dd, 2"-Hax), 2.29 (d, 2"-Heq), 4.72 (d, 4"-H), 4.54 (dq, 5"-H), 1.07 (d, 6"-$H_3$), 1.10 (s, 7"-$H_3$), 3.26 (s, 3"-$OCH_3$), 2.42 apparent q, 4"-$OCOCH_2CH_3$), 2.43 (apparent q, 4"-$OCOCH_2CH_3$), 1.17 (t, 4"-$OC\overline{O}CH_2\underline{CH_3}$).

EXAMPLE 2

Process (1) for producing compound (2) [a compound represented by the formula (I) wherein $R^1$ represents a hydrogen atom, $R^2$ represents a hydrogen atom, $R^3$ represents a hydrogen atom and $R^4$ represents a propionyl group] (3"-O-methylleucomycin $A_7$):

As a preculture medium, a medium comprising 2.0% of starch, 1.0% of glucose, 0.6% of wheat embryo, 0.5% of polypeptone, 0.3% of powdery yeast extract, 0.2% of soybean powder and 0.2% of calcium carbonate was employed. As a conversion medium, a medium comprising 3.0% of glucose, 1.5% of starch, 1.25% of soybean powder, 0.8% of wheat embryo, 0.125% of sodium chloride and 0.15% of calcium carbonate was employed. These media were adjusted to pH 7.0 and then sterilized prior to the use. The above-mentioned preculture medium was pipetted in 20 ml portions into five 100 ml-Erlenmeyer's flasks and sterilized at 120° C. for 30 minutes. Then the preculture medium was inoculated with one platinum loopful of Phialophora sp. PF1083 strain (FERM BP-3960), which had been stationarily incubated by slant agar culture containing 0.2% of yeast extract, 1.0% of starch and 2.0% of agar powder (pH 7.0) at 26° C. for 4 to 6 days, followed by incubating at 26° C. for 2 days under shaking. Thus a preculture liquor was obtained. Next, the above-mentioned conversion medium was pipetted in 100 ml portions into fifteen 500 ml-Erlenmeyer's flasks and sterilized at 120° C. for 30 minutes. Then 22.5 ml of a methanol solution containing 393 mg of the compound (1) represented by the formula (XI), wherein $R^1$ represents a propionyl group and $R^4$ represents an propionyl group (3"-O-methylmidecamycin $A_1$), was added to each flask in 1.5 ml portions and the conversion medium in each flask was inoculated with 5 ml of the seed culture liquor, followed by incubating at 26° C. for 10 days under shaking. After the completion of the incubation, the culture liquor was centrifuged at 3000 rpm for 10 minutes. Thus 1.1 liters of a transparent culture supernatant was obtained while the solid matters including the cells were removed. To the solid matters was added 900 ml of water and the resulting mixture was stirred followed by centrifugation. The washing liquor thus obtained was combined with the above-mentioned transparent culture supernatant. After adjusting the mixture to pH 9, the conversion product was extracted with 1.5 liters of ethyl acetate and then with 1.0 liter of ethyl acetate twice. The ethyl acetate layer was dried over anhydrous sodium sulfate and then filtered. The filtrate was concentrated under reduced pressure and the residue thus obtained was purified by preparative TLC [developing system: chloroform/methanol/conc. aqueous ammonia (400:40:1)] to obtain 102 mg of the compound (2). Simultaneously, 63 mg of the compound (1) was recovered.

Physicochemical properties of the compound (2)
(1) Color and appearance: colorless solid.
(2) Molecular formula: $C_{39}H_{65}NO_{14}$.
(3) Mass spectrum (EIMS): m/z 771 (M)$^+$.
(4) Specific rotation: $[\alpha]_D^{17}$ −79° (c 1.0, $CH_3OH$).
(5) m.p.: melting at around 111° to 113° C. without showing any definite melting point.
(6) $^1$H NMR spectrum (400 MHz, $CDCl_3$) δ (ppm: 2.22 (d, 2-H), 2.70 (dd, 2-H), 3.79 (br d, 3-H), 3.09 (br d, 4-H), 3.54 (s, 4-$OCH_3$), 4.11 (br d, 5-H ), 0.95 ( br ddd, 7-H ), 1.60 (br dt, 7-H), 1.90 (m, 8-H), 4.10 (dd, 9-H), 5.68 (dd, 10-H), 6.26 (dd, 11-H), 6.03 (br dd, 12-H), 5.61 (ddd, 13-H), 2.12 (dt, 14-H), 2.51 (br dt, 14-H), 5.29 (ddq, 15-H), 1.30 (d, 16-$H_3$), 2.34 (br dd, 17-H), 2.87 (br dd, 17-H), 9.80 (br s, 18-H), 0.99 (d, 19-$H_3$), 4.58 (d, 1'-H), 3.22 (dd, 2'-H), 2.42 (t, 3'-H), 3.45 (t, 4'-H), 3.28 (dq, 5'-H), 1.19 (d, 6'-$H_3$), 2.57 (s, 3'-N($CH_3$)$_2$), 4.93 (d, 1"-H), 1.66 (dd, 2"-Hax), 2.29 (d, 2"-Heq), 4.72 (d, 4"-H), 4.54 (dq, 5"-H), 1.07 (d, 6"-$H_3$), 1.10 (s, 7"-$H_3$), 3.26 (s, 3"-$OCH_3$), 2.42 (apparent q, 4"-$OCOCH_2CH_3$), 2.43 (apparent q, 4"-$OCOCH_2CH_3$) 1.17 (t, 4"-$OCOCH_2CH_3$).

EXAMPLE 3 process for producing compound (3) [a compound represented by the formula (I) wherein $R^1$ represents a propionyl group, $R^2$ represents a hydrogen atom, $R^3$ represents a hydrogen atom and $R^4$ represents a hydrogen atom] (3"-O-methylmidecamycin $M_1$):

As a preculture medium, a medium comprising 2.0% of starch, 1.0% of glucose, 0.5% of polypeptone, 0.6% of wheat embryo, 0.3% of yeast extract, 0.2% of soybean cake and 0.2% of calcium carbonate was employed. The medium was adjusted to pH 7.0 and then sterilized prior to the use. This medium was pipetted in 20 ml portions into three 100 ml-Erlenmeyer's flasks and sterilized at 120° C. for 30 minutes. Then the preculture medium was inoculated with 1.0 ml of a frozen seed of *Mucor spinescens* IAM 6071 strain and incubated at 26° C. for 24 hours under shaking to give a preculture liquor. As a conversion medium, a medium comprising 1.8% of glucose, 0.9% of starch, 1.25% of soybean cake, 0.8% of wheat embryo, 0.125% of sodium chloride and 0.15% of calcium carbonate was employed. The medium was adjusted to pH 7.0 and then sterilized prior to the use. The conversion medium was pipetted in 100 ml portions into seven 500 ml-Erlenmeyer's flasks and sterilized at 120° C. for 30 minutes. Then 10.5 ml of a methanol solution containing 88 mg of the compound (1) represented by the formula (XI), wherein $R^1$ represents a propionyl group and $R^4$ represents an propionyl group (3"-O-methylmidecamycin $A_1$), was added to each flask in 1.5 ml portions and the conversion medium in each flask was inoculated with 5.0 ml of the preculture liquor of IAM 6071 strain, followed by incubating at 26° C. for 8 days under shaking to effect microbial conversion. After the completion of the incubation, the culture liquor was adjusted to pH 9 and then 600 ml of ethyl acetate was added thereto. The resulting mixture was shaken vigorously and centrifuged at 3500 rpm for 10 minutes to separate an ethyl acetate layer. Six hundred ml of ethyl acetate was added to the solid matters including the cells and an aqueous layer and the resulting mixture was shaken vigorously followed by centrifugation at 3500 rpm for 10 minutes. The two ethyl acetate layers were combined was dried over anhydrous sodium sulfate and then filtered. The filtrate was concentrated under reduced pressure and the residue thus obtained was purified by preparative TLC [developing system: chloroform/methanol/conc. aqueous ammonia (100:10:1)] to obtain 32 mg of the compound (3). Simultaneously, 24 mg of the compound (1) was recovered.

Physicochemical properties of the compound (3)
(1) Color and appearance: colorless solid.
(2) Molecular formula: $C_{39}H_{65}NO_{14}$.
(3) Mass spectrum (EIMS): m/z 771 (M)$^+$.
(4) Specific rotation: $[\alpha]_D^{17}$ −56° (c 1.0, $CH_3OH$).
(5) m.p.: melting at around 120° to 122° C. without showing any definite melting point.
(6) $^1$H NMR spectrum (400 MHz, $CDCl_3$) δ (ppm: 2.24 (br d, 2-H), 2.76 (dd, 2-H), 5.14 (br d, 3-H), 3.26 (br d, 4-H), 3.58 (s, 4-$OCH_3$), 3.88 (br d, 5-H), 0.92 (br ddd, 7-H), 1.54 (br dt, 7-H), 1.89 (m, 8-H), 4.07 (dd, 9-H), 5.61 (dd, 10-H), 6.67 (dd, 11-H), 6.08 (br dd, 12-H), 5.79 (ddd, 13-H), 2.15 (dt, 14-H), 2.46 (br dt, 14-H), 5.03 (ddq, 15-H), 1.26 (d, 16-$H_3$), 2.32 (br dd, 17-H), 2.86 (br dd, 17-H), 9.63 (br s, 18-H), 0.98 (d, 19-$H_3$), 2.51 (dq, 3-$OCOCH_2CH_3$), 2.65 (dq, 3-$OCOCH_2CH_3$), 1.22 (t, 3-$OCOCH_2CH_3$) 4.51 (d, 1'-H), 3.21 (dd, 2'-H), 2.39 (t, 3'-H), 3.44 (t, 4'-H), 3.27 (dq, 5'-H), 1.16 (d, 6'-$H_3$), 2.55 (s, 3'-N($CH_3$)$_2$), 4.88 (d, 1"-H), 1.57 (dd, 2"-Hax), 2.23 (d, 2"-Heq), 3.01 (br t, 4"-H), 4.18 (dq, 5"-H), 1.23 (d, 6"-$H_3$), 1.22 (s, 7"-$H_3$), 3.22 (s, 3"-$OCH_3$).

EXAMPLE 4

Process for producing compound (4) [a compound represented by the formula (I) wherein $R^1$ represents a hydrogen atom, $R^2$ represents a hydrogen atom, $R^3$ represents a hydrogen atom and $R^4$ represents a hydrogen atom] (3"-O-methylleucomycin V):

The same preculture medium as employed in Example 3 was adjusted to pH 7.0 and then sterilized prior to the use. A preculture liquor of *Mucor spinescens* IAM 6071 strain was prepared in the same manner as in Example 3. Also, the same conversion medium employed in Example 3 was adjusted to pH 7.0 and then sterilized prior to the use. The conversion medium was pipetted in 100 ml portions into seven 500 ml-Erlenmeyer's flasks and sterilized at 120° C. for 30 minutes. Then, 10.5 ml of a methanol solution containing 82 mg of the compound (2) represented by the formula (XII), wherein $R^4$ represents an propionyl group (3"-O-methylmidecamycin $A_7$), was added to each flask in 1.5 ml portions and the conversion medium in each flask was inoculated with 5.0 ml of the preculture liquor of IAM 6071 strain, followed by incubating at 26° C. for 9 days under shaking to effect microbial conversion. After the completion of the incubation, the culture liquor was adjusted to pH 9 and then 600 ml of ethyl acetate was added thereto. The resulting mixture was shaken vigorously and centrifuged at 3500 rpm for 10 minutes to separate an ethyl acetate layer. Six hundred ml of ethyl acetate was added to the solid matters including the cells and an aqueous layer and the resulting mixture was shaken vigorously followed by centrifugation at 3500 rpm for 10 minutes. The two ethyl acetate layers were combined was dried over anhydrous sodium sulfate and then filtered. The filtrate was concentrated under reduced pressure and the residue thus obtained was purified by preparative TLC [developing system: chloroform/methanol/conc. aqueous ammonia (100:10:1)] to obtain 17 mg of the compound (4). Simultaneously, 14 mg of the compound (2) was recovered.
Physicochemical properties of the compound (4)
  (1) Color and appearance: colorless solid.
  (2) Molecular formula: $C_{36}H_{61}NO_{13}$.
  (3) Mass spectrum (EIMS): m/z 715 $(M)^+$.
  (4) Specific rotation: $[\alpha]_D^{17}$ −74° (c 1.0, $CH_3OH$).
  (5) m.p.: melting at around 117° to 122° C. without showing any definite melting point.
  (6) $^1H$ NMR spectrum (400 MHz, $CDCl_3$) δ (ppm: 2.23 (d, 2-H), 2.70 (dd, 2-H), 3.80 (br d, 3-H), 3.10 (br d, 4-H), 3.55 (s, 4-$OCH_3$), 4.11 (br d, 5-H), 0.95 (br ddd, 7-H), 1.60 (br dt, 7-H), 1.91 (m, 8-H), 4.11 (dd, 9-H), 5.69 (dd, 10-H), 6.27 (dd, 11-H), 6.04 (br dd, 12-H), 5.61 (ddd, 13-H), 2.12 (dt, 14-H), 2.51 (br dt, 14-H), 5.29 (ddq, 15-H), 1.31 (d, 16-$H_3$), 2.34 (br dd, 17-H), 2.88 (br dd, 17-H), 9.80 (br s, 18-H), 0.99 (d, 19-$H_3$), 4.58 (d, 1'-H), 3.23 (dd, 2'-H), 2.40 (t, 3'-H), 3.44 (t, 4'-H), 3.26 (dq, 5'-H), 1.19 (d, 6'-$H_3$), 2.56 (s, 3'-$N(CH_3)_2$), 4.89 (d, 1"-H), 1.57 (dd, 2"-Hax), 2.24 (d, 2"-Heq), 3.01 (br t, 4"-H), 4.18 (dq, 5"-H), 1.23 (d, 6"-$H_3$), 1.22 (s, 7"-$H_3$), 3.22 (s, 3"-$OCH_3$).

EXAMPLE 5

Process (1) for producing compound (5) [a compound represented by the formula (I) wherein $R^1$ represents a propionyl group, $R^2$ represents an acetyl group, $R^3$ represents a hydrogen atom and $R^4$ represents a propionyl group] (9-O-acetyl-3"-O-methylmidecamycin $A_1$):

Thirteen μl of dry pyridine and 11 μl of acetyl chloride were successively added to 1.5 ml of dry toluene solution having dissolved therein 30 mg of the compound (1) represented by the formula (XI) wherein $R^1$ represents a propionyl group and $R^4$ represents a propionyl group (3"-O-methylmidecamycin $A_1$), followed by stirring at room temperature for 1 hour. After adding 19 μl of triethylamine, 15 ml of ethyl acetate was added to effect extraction. The ethyl acetate layer was washed with 15 ml portions of water twice, dried over anhydrous sodium sulfate and then filtered. The filtrate was concentrated under reduced pressure and the residue thus obtained was purified by preparative TLC [developing system: chloroform/methanol (12:1)]. Thus 18 mg of the compound (5) was obtained.
Physicochemical properties of the compound (5)
  (1) Color and appearance: colorless solid.
  (2) Molecular formula: $C_{44}H_{71}NO_{16}$.
  (3) Mass spectrum (EIMS): m/z 869 $(M)^+$.
  (4) Specific rotation: $[\alpha]_D^{24}$ −60° (c 1.0, $CH_3OH$).
  (5) m.p.: melting at around 118° to 121° C. without showing any definite melting point.
  (6) $^1H$ NMR spectrum (400 MHz, $CDCl_3$) δ (ppm: 2.26 (br d, 2-H), 2.74 (dd, 2-H), 5.12 (br d, 3-H), 3.25 (br d, 4-H), 3.57 (s, 4-$OCH_3$), 3.93 (br d, 5-H), 0.93 (br ddd, 7-H ), 1.57 (br dt, 7-H), 5.08 (dd, 9-H), 5.57 (dd, 10-H), 6.74 (dd, 11-H), 6.09 (br dd, 12-H), 5.88 (ddd, 13-H), 2.17 (dt, 14-H), 4.98 (ddq, 15-H), 1.26 (d, 16-$H_3$), 2.58 (br dd, 17-H), 2.83 (br dd, 17-H), 9.65 (br s, 18-H), 0.96 (d, 19-$H_3$), 2.51 (dq, 3-OCO$CH_2CH_3$), 2.67 (dq, 3-OCO$CH_2CH_3$), 1.21 (t, 3-OCO$CH_2C H_3$), 2.02 (s, 9-$OCOCH_3$), 4.51 (d, 1'-H ), 3.20 (dd, 2'-H), 2.41 (t, 3'-H), 3.45 (t, 4'-H), 3.28 (dq, 5'-H), 1.16 (d, 6'-$H_3$), 2.57 (s, 3'-$N(CH_3)_2$), 4.93 (d, 1"-H), 1.67 (dd, 2"-Hax), 2.30 (d, 2"-Heq), 4.72 (d, 4"-H), 4.54 (dq, 5"-H), 1.08 (d, 6"-$H_3$), 1.10 (s, 7"-$H_3$), 3.26 (s, 3"-$OCH_3$), 2.43 (apparent q, 4"-OCO$CH_2CH_3$), 2.44 (apparent q, 4"-OCO$CH_2CH_3$), 1.18 (t, 4"-OCO$CH_2CH_3$).

EXAMPLE 6

Process (1) for producing compound (6) [a compound represented by the formula (I) wherein $R^1$ represents a hydrogen atom, $R^2$ represents an acetyl group, $R^3$ represents a hydrogen atom and $R^4$ represents a propionyl group] (9-O-acetyl-3"-O-methylleucomycin $A_7$):

Twelve μl of dry pyridine and 9.1 μl of acetyl chloride were successively added to 1.4 ml of dry toluene solution having dissolved therein 28 mg of the compound (2) represented by the formula (XII) wherein $R^4$ represents a propionyl group (3"-O-metylleucomycin $A_1$), followed by stirring at room temperature for 2 hours. After adding 17 μl of triethylamine, 10 ml of ethyl acetate was added to effect extraction. The ethyl acetate layer was washed with 10 ml portions of water twice, dried over anhydrous sodium sulfate and then filtered. The filtrate was concentrated under reduced pressure and the residue thus obtained was purified by preparative TLC [developing system: chloroform/methanol/conc. aqueous ammonia (240:20:1)]. Thus 15 mg of the compound (6) was obtained.
Physicochemical properties of the compound (6)
  (1) Color and appearance: colorless solid.
  (2) Molecular formula: $C_{41}H_{67}NO_{15}$.
  (3) Mass spectrum (EIMS): m/z 813 $(M)^+$.
  (4) Specific rotation: $[\alpha]_D^{25}$ −68° (c 1.0, $CH_3OH$).
  (5) m.p.: melting at around 110° to 113° C. without showing any definite melting point.
  (6) $^1H$ NMR spectrum (400 MHz, $CDCl_3$) δ (ppm: 2.22 (d, 2-H), 2.71 (dd, 2-H), 3.79 (br d, 3-H), 3.09 (br d, 4-H), 3.54 (s, 4-$OCH_3$), 4.14 (br d, 5-H), 0.98 (br ddd, 7-H), 1.62 (br dt, 7-H), 5.18 (dd, 9-H), 5.60 (dd, 10-H), 6.40 (dd, 11-H), 6.03 (br dd, 12-H), 5.66 (ddd, 13-H), 2.12 (dt, 14-H), 2.51 (br dt, 14-H), 5.29 (ddq, 15-H), 1.31 (d, 16-$H_3$), 2.46 (br dd, 17-H), 2.83 (br dd, 17-H), 9.81 (br s, 18-H), 0.99 (d, 19-$H_3$), 2.00 (s, 9-$OCOCH_3$), 4.57 (d, 1'-H), 3.21 (dd, 2'-H), 2.42 (t, 3'-H), 3.45 (t, 4'-H), 3.28 (dq, 5'-H), 1.20 (d, 6'-$H_3$), 2.57 (s, 3'-$N(CH_3)_2$), 4.93 (d, 1"-H), 1.66 (dd, 2"-Hax), 2.30 (d, 2"-Heq), 4.72 (d, 4"-H), 4.54 (dq, 5"-H), 1.08 (d, 6"-$H_3$), 1.10 (s, 7"-$H_3$), 3.26 (s, 3"-$OCH_3$), 2.43 (apparent q, 4"-OCO$CH_2CH_3$), 2.44 (apparent q, 4"-OCO$CH_2CH_3$), 1.18 (t, 4"-OCOC $H_2CH_3$).

EXAMPLE 7

Process (2) for producing compound (5) [a compound represented by the formula (I) wherein $R^1$ represents a propionyl group, $R^2$ represents an acetyl group, $R^3$ represents a hydrogen atom and $R^4$ represents a propionyl group] (9-O-propionyl-3"-O-methylmidecamycin $A_1$]:

First, the activity of Raney nickel was controlled. Namely, 6 ml of Raney nickel was washed with 10 ml portions of water twice and then with 10 ml portions of acetone three times with suppressing heat evolution to appropriately control its activity. Then, it was further washed with 10 ml portions of ethanol twice. In 20 ml of ethanol was dissolved 227 mg of the compound (7) represented by the formula (XVIII) wherein $R^1$ is a propionyl group, $R^2$ is an acetyl group and $R^4$ is a propionyl group [*Journal of Antibiotics*, 33(1), 61 (1980)]. The above prepared Raney nickel and 5.0 ml of ethanol were added thereto followed by stirring vigorously at room temperature for 20 minutes. Insoluble matters were filtered off and washed with 20 ml portions of ethanol containing 1%(v/v) conc. aqueous ammonia twice. The filtrate and washings were combined and concentrated under reduced pressure. Then, 290 mg of the resulting residue was purified by preparative TLC [developing system: benzene/acetone (3:1) ] to thereby give 79 mg of the compound (5).

EXAMPLE 8

Process for producing compound (9) [a compound represented by the formula (XVII) wherein $R^1$ represents an acetyl group, $R^2$ represents an acetyl group and $R^4$ represents an isovaleryl group]:

In a mixed solution of 63 ml of dimethyl sulfoxide (DMSO) and 6.3 ml of anhydrous acetic acid was dissolved 2.0 g of the compound (8) represented by the formula (XVI) wherein $R^1$ is an acetyl group, $R^2$ represents an acetyl group and $R^4$ represents an isovaleryl group [*Tetrahedron Letters*, 609 (1967)]. The reaction mixture was allowed to react at 33° C. for 3 days. After adding 2.0 liters of toluene, the reaction mixture was washed with 2.0 liter portions of water four times. The toluene layer was dried over anhydrous sodium sulfate and filtered. Then the filtrate was concentrated under reduced pressure and 3.0 g of the residue thus obtained was purified by silica gel column chromatography [300 g: hexane/ethyl acetate (3:1)→(1:1)]. Thus 1.4 g of the compound (9) was obtained.

Physicochemical properties of the compound (9)
(1) Color and appearance: colorless solid.
(2) Molecular formula: $C_{48}H_{77}NO_{17}S$.
(3) Mass spectrum (SIMS): m/z 972 (M+H)$^+$.
(4) Specific rotation: $[\alpha]_D^{24}$ –85° (c 1.0, CHCl$_3$).
(5) m.p.: melting at around 118° to 122° C. without showing any definite melting point.
(6) $^1$H NMR spectrum (400 MHz, CDCl$_3$) δ (ppm: 2.25 (br d, 2-H), 2.72 (dd, 2-H), 5.09 (br d, 3-H), 3.16 (br d, 4-H), 3.50 (s, 4-OCH$_3$), 3.94 (br d, 5-H), 0.85 (br ddd, 7-H), 1.46 (br dt, 7-H), 5.05 (dd, 9-H), 5.56 (dd, 10-H), 6.70 (dd, 11-H), 6.05 (br dd, 12-H), 5.85 (ddd, 13-H), 2.45 (br dt, 14-H), 4.99 (ddq, 15-H), 1.26 (d, 16-H$_3$), 2.55 (br dd, 17-H), 2.81 (br dd, 17-H), 9.63 (br s, 18-H), 0.96 (d, 19-H$_3$), 2.30 (s, 3-OCOCH$_3$), 2.00 (s, 9-OCOCH$_3$), 4.59 (d, 1'-H ), 4.91 (dd, 2'H), 2.68 (t, 3'-H), 3.16 (t, 4'-H), 3.26 (dq, 5'-H), 1.14 (d, 6'-H$_3$), 2.00 (s, 2'-OCOCH$_3$), 2.42 (s, 3'-N(CH$_3$)$_2$), 4.81 (d, 1"-H), 1.68 (dd, 2"-Hax), 1.18 (s, 3"-CH$_3$), 4.63 (d, 4"-H), 4.56 (dq, 5"-H), 1.05 (d, 6"-H$_3$), 4.50 (d, 3"-OCH$_2$SCH$_3$), 4.64 (d, 3"-OCH$_2$SCH$_3$), 2.20 (s, 3"-OCH$_2$SCH$_3$), 0.98 (d, 4"-OCOCH$_2$CH(CH$_3$)$_2$).

EXAMPLE 9

Process for producing compound (10) [a compound represented by the formula (XVIII) wherein $R^1$ represents an acetyl group, $R^2$ represents an acetyl group and $R^4$ represents an isovaleryl group]:

To 39 ml of methanol was added 1.30 g of the compound (9) followed by reaction at 33° C. for 16 hours. The reaction mixture was concentrated under reduced pressure and 1.29 g of the residue thus obtained was purified by silica gel column chromatography [125 g: hexane/ethyl acetate (1:1)]. Thus 964 mg of the compound (10) was obtained.

Physicochemical properties of the compound (10)
(1) Color and appearance: colorless solid.
(2) Molecular formula: $C_{46}H_{75}NO_{16}S$.
(3) Mass spectrum (SIMS): m/z 930 (M+H)$^+$.
(4) Specific rotation: $[\alpha]_D^{24}$ –77° (c 1.0, CH$_3$OH).
(5) m.p.: melting at around 115° to 118° C. without showing any definite melting point.
(6) $^1$H NMR spectrum (400 MHz, CDCl$_3$) δ (ppm: 2.27 (br d, 2-H), 2.75 (dd, 2-H), 5.00 (br d, 3-H), 3.25 (br d, 4-H), 3.57 (s, 4-OCH$_3$), 3.96 (br d, 5-H), 0.93 (br ddd, 7-H), 1.57 (br dt, 7-H), 4.97 (dd, 9-H), 5.57 (dd, 10-H), 6.71 (dd, 11-H), 6.09 (br dd, 12-H), 5.86 (ddd, 13-H), 2.47 (br dt, 14-H), 5.00 (ddq, 15-H), 1.27 (d, 16-H$_3$), 2.59 (br dd, 17-H), 2.84 (br dd, 17-H), 9.66 (br s, 18-H), 0.96 (d, 19-H$_3$), 2.29 (s, 3-OCOCH$_3$), 2.01 (s, 9-OCOCH$_3$), 4.50 (d, 1'-H), 3.21 (dd, 2'-H), 2.42 (t, 3'-H), 3.42 (t, 4'-H), 3.28 (dq, 5'-H), 1.15 (d, 6'-H$_3$), 2.58 (s, 3'-N(CH$_3$)$_2$), 4.92 (d, 1"-H), 1.74 (dd, 2"-Hax), 1.20 (s, 3"-CH$_3$), 4.66 (d, 4"-H), 4.56 (dq, 5"-H), 1.08 (d, 6"-H$_3$), 4.52 ( d, 3"-OCH$_2$SCH$_3$), 4.65 (d, 3"-OCH$_2$SCH$_3$), 2.18 (s, 3"-OCH$_2$SCH$_3$), 0.98 (d, 4"-OCOCH$_2$CH(CH$_3$)$_2$).

EXAMPLE 10

Process for producing compound (11) [a compound represented by the formula (I) wherein $R^1$ represents an acetyl group, $R^2$ represents an acetyl group, $R^3$ represents a hydrogen atom and $R^4$ represents an isovaleryl group] (9-O-acetyl-3"-O-methyljosamycin]:

Three hundred mg of the compound (10) was dissolved in 7.0 ml of ethanol. Fifteen ml of Raney nickel was treated in the same manner as in Example 7 to control its activity and added to the above solution together with 7.5 ml of ethanol. The resulting mixture was stirred vigorously at room temperature for 20 minutes. Insoluble matters were filtered off and washed with 30 ml portions of ethanol containing 1%(v/v) conc. aqueous ammonia twice. The filtrate and washings were combined and concentrated under reduced pressure. Then, 297 mg of the resulting residue was purified by preparative TLC [developing system: toluene/acetone (3:1)] to thereby give 81 mg of the compound (11).

Physicochemical properties of the compound (11)
(1) Color and appearance: colorless solid.
(2) Molecular formula: $C_{45}H_{73}NO_{16}$.
(3) Mass spectrum (SIMS): m/z 884 (M+H)$^+$.
(4) Specific rotation: $[\alpha]_D^{26}$ –74° (c 1.0, CH$_3$OH).
(5) m.p.: melting at around 115° to 119° C. without showing any definite melting point.
(6) $^1$H NMR spectrum (400 MHz, CDCl$_3$) δ (ppm: 2.75 (dd, 2-H), 5.12 (br d, 3-H), 3.25 (br d, 4-H), 3.57 (s, 4-OCH$_3$), 3.96 (br d, 5-H), 0.92 (br ddd, 7-H), 1.58 (br dt, 7-H), 5.06 (dd, 9-H), 5.57 (dd, 10-H), 6.71 (dd, 11-H), 6.09 (br dd, 12-H), 5.86 (ddd, 13-H), 4.99 (ddq, 15-H), 1.26 (d, 16-H$_3$), 2.59 (br dd, 17-H), 2.84 (br dd, 17-H), 9.66 (br s, 18-H), 0.96 (d, 19-H$_3$), 2.29 (s, 3-OCOCH$_3$), 2.01 (s, 9-OCOCH$_3$), 4.51 (d, 1'-H), 3.19 (dd, 2'-H), 2.42 (t, 3'-H), 3.46 (t, 4'-H), 3.29 (dq, 5'-H), 1.16 (d, 6'-H$_3$), 2.58 (s, 3'-N(CH$_3$)$_2$), 4.93 (d, 1"-H), 1.67 (dd, 2"-Hax), 1.11 (s, 3"-CH$_3$), 4.72 (d, 4"-H), 5.54 (dq, 5"-H), 1.08 (d, 6"-H$_3$), 3.26 (s, 3"-OCH$_3$), 0.97 (d, 4"-OCOCH$_2$CH(CH$_3$)$_2$).

EXAMPLE 11

Process for producing compound (12) [a compound represented by the formula (XV) wherein $R^1$ represents a propionyl group, $R^2$ represents a 1-ethoxyethyl group and $R^4$ represents a propionryl group]:

Twenty g of medemycin was dissolved in a mixed solution of 600 ml of methylene chloride and 22 ml of ethyl vinyl ether. After adding 9.4 g of PPTS thereto, the resulting mixture was allowed to react at room temperature for 16 hours. The reaction mixture was added to 2.0 liters of a saturated sodium hydrogencarbonate solution by slow degrees followed by extraction with 1.8 liters of chloroform. The chloroform layer was washed subsequently with 2.0 liters of a 5% potassium hydrogensulfate solution, 2.0 liters of a saturated sodium hydrogencarbonate solution and 2.0 liters of a saturated sodium chloride solution. The chloroform layer was dried over anhydrous sodium sulfate and filtered. Then the filtrate was concentrated under reduced pressure and 23 g of the residue thus obtained was purified by silica gel column chromatography [1.0 kg: chloroform/methanol (50:1)]. Thus 20 g of the compound (12) was obtained.

Physicochemical properties of the compound (12)

(1) Color and appearance: colorless solid.
(2) Molecular formula: $C_{45}H_{75}NO_{16}$.
(3) Mass spectrum (EIMS): m/z 885 $(M)^+$.
(4) Specific rotation: $[\alpha]_D^{21}$ –61° (c 1.0, $CH_3OH$).
(5) m.p.: melting at around 100° to 103° C. without showing any definite melting point.
(6) $^1H$ NMR spectrum (400 MHz, $CDCl_3$) δ (ppm: 2.28 (br d, 2-H), 2.73 (dd, 2-H), 2.74 (dd, 2-H), 5.13 (br d, 3-H), 3.24 (br d, 4-H), 3.53 (s, 4-$OCH_3$), 3.87 (br d, 5-H), 1.44 (br dt, 7-H), 1.90 (m, 8-H), 3.78 (dd, 9-H), 3.92 (dd, 9-H), 5.47 (dd, 10-H), 5.56 (dd, 10-H), 6.57 (dd, 11-H), 6.61 (dd, 11-H), 6.09 (br dd, 12-H), 5.78 (br ddd, 13-H), 5.82 (br ddd, 13-H), 2.15 (br dt, 14-H), 5.02 (ddq, 15-H), 2.82 (br dd, 17-H), 2.83 (br dd, 17-H), 9.64 (br s, 18-H), 9.65 (br s, 18-H), 0.99 (d, 19-$H_3$), 1.00 (d, 19-$H_3$), 2.63 (br dq, 3-OCOC$H_2$CH$_3$), 4.64 (q, 9-OC$\underline{H}$(OCH$_2$CH$_3$)CH$_3$), 4.66 (q, 9-OC$\underline{H}$(OCH$_2$CH$_3$)CH$_3$), 3.44 (dq, 9-OCH(OC$\underline{H}_2$CH$_3$)CH$_3$), 3.63 (dq, 9-OCH(OC$\underline{H}_2$)CH$_3$), 4.41 ( d, 1'-H), 2.51 (s, 3'-N(CH$_3$)$_2$), 5.07 (d, 1"-H), 1.85 (dd, 2"-Hax), 2.01 (d, 2"-Heq), 1.12 (s, 3"-CH$_3$), 4.62 (d, 4"-H), 4.46 (dq, 5"-H), 1.13 (d, 6"-H$_3$), 2.44 (apparent q, 4"-OCOC$\underline{H}_2$CH$_3$), 2.46 (apparent q, 4"-OCOC$\underline{H}_2$CH$_3$), 1.18 ( t, 4"-OCOCH$_2$C$\underline{H}_3$).

EXAMPLE 12

Process for producing compound (13) [a compound represented by the formula (XVI) wherein $R^1$ represents a propionyl group, $R^2$ represents a 1-ethoxyethyl group and $R^4$ represents a propionyl group]:

To 370 ml of acetonitrile was added 12.0 g of the compound (12). After 2.7 ml of acetic anhydride was added thereto, the mixture was reacted at 40° C. for 16 hours. Then, 42 ml of 1N aqueous ammonia was added dropwise to the reaction mixture and the mixture was allowed to stand for 10 minutes. The reaction mixture was concentrated under reduced pressure and the resulting residue was dissolved in 1.0 liter of chloroform and successively washed with 1.0 liter of a saturated aqueous solution of sodium hydrogencarbonate and 1.2 liter of a saturated aqueous solution of sodium chloride. The chloroform layer was dried over anhydrous sodium sulfate and filtered. The filtrate was concentrated under reduced pressure to obtain 13.0 g of the compound (13).

Physicochemical properties of the compound (13)

(1) Color and appearance: colorless solid.
(2) Molecular formula: $C_{47}H_{77}NO_{17}$.
(3) Mass spectrum (SIMS): m/z 928 $(M+H)^+$.
(4) Specific rotation: $[\alpha]_D^{21}$ –64° (c 1.0, $CHCl_3$).
(5) Melting at around 104° to 107° C. without showing any definite melting point.
(6) $^1H$ NMR spectrum (400 MHz, $CDCl_3$) δ (ppm: 2.24 (br d, 2-H), 2.70 (dd, 2-H), 5.11 (br d, 3-H), 3.17 (br d, 4-H), 3.47 (s, 4-$OCH_3$), 3.89 (br d, 5-H), 1.42 (br t, 7-H), 3.75 (dd, 9-H), 3.88 (dd, 9-H), 5.45 (dd, 10-H), 5.54 (dd, 10-H), 6.57 (dd, 11-H), 6.61 (dd, 11-H), 6.05 (br dd, 12-H), 5.79 (ddd, 13-H), 5.83 (ddd, 13-H), 2.15 (br dt, 14-H), 2.26 (br dd, 17-H), 2.81 (br dd, 17-H), 9.62 (br s, 18-H), 9.63 (br s, 18-H), 0.98 (d, 19-$H_3$), 0.99 (d, 19-$H_3$), 2.65 (dq, 3-OCOC$\underline{H}_2$CH$_3$), 4.64 (q, 9-OC$\underline{H}$(OCH$_2$CH$_3$)CH$_3$), 4.65 (q, 9-OC$\underline{H}$(OCH$_2$CH$_3$)CH$_3$), 3.35 (dq, 9-OCH(OC$\underline{H}_2$CH$_3$)CH$_3$), 3.43 (dq, 9-OCH (OC$\underline{H}_2$CH$_3$)CH$_3$), 3.49 (dq, 9-OCH(OC$\underline{H}_2$CH$_3$)CH$_3$), 3.62 (dq, 9-OCH(OCH$_2$CH$_3$)CH$_3$), 4.61 (d, 1'-H), 4.98 (dd, 2'-H), 2.02 (s, 2'-OCOCH$_3$), 2.41 (s, 3'-N(CH$_3$)$_2$), 5.06 (d, 1"-H), 1.84 (dd, 2"-Hax), 2.00 (d, 2"-Heq), 1.12 (br s, 3"-CH$_3$), 4.62 (d, 4"-H), 4.37 (dq, 5"-H), 2.43 (apparent q, 4-OCOC$\underline{H}_2$CH$_3$), 2.44 (apparent q, 4"-OCOC$\underline{H}_2$CH$_3$), 1.18 (t, 4"-OCOH$_2$C$\underline{H}_3$).

EXAMPLE 13

Process for producing compound (14H) [a compound represented by the formula (XVII) wherein $R^1$ represents a propionyl group, $R^2$ represents a 1-ethoxyethyl group, $R^4$ represents a propionyl group, which is an isomer giving a higher Rf value as a result of TLC using the following developing system] and compound (14L) [a compound represented by the formula (XVII) wherein $R^1$ represents a propionyl group, $R^2$ is a 1-ethoxyethyl group and $R^4$ is a propionyl group, which is an isomer giving a lower Rf value as a result of TLC using the following developing system]:

After 305 mg of the compound (13) was dissolved in a mixed solution of 9.1 ml of DMSO and 0.91 ml of acetic anhydride, the resulting mixture was allowed to react at 30° C. for 16 hours. The reaction mixture was added to 60 ml of toluene by slow degrees and washed with 60 ml portions of water three times. The toluene layer was dried over anhydrous sodium sulfate and filtered. The filtrate was concentrated under reduced pressure and 300 mg of the residue thus obtained was purified by silica gel column chromatography [30 g: hexane/ethyl acetate (1:1)]. Thus 195 mg of the compound (14) was obtained. Then, 106 mg of the thus obtained compound was further purified by preparative TLC (developing system: hexane/ethyl acetate (1:1)] to obtain 56 mg of the compound (14H) and 39 mg of the compound (14L).

Physicochemical properties of the compound (14H)

(1) Color and appearance: colorless solid.
(2) Molecular formula: $C_{49}H_{81}NO_{17}S$.
(3) Mass spectrum (FDMS): m/z 988 $(M+H)^+$.
(4) Rf value on TLC: 0.50 [developing system: hexane/ethyl acetate (1:1)].
(5) Specific rotation: $[\alpha]_D^{19}$ –71° (c 1.0, $CHCl_3$).
(6) Melting at around 94° to 96° C. without showing any definite melting point.
(7) $^1H$ NMR spectrum (400 MHz, $CDCl_3$) δ (ppm: 2.24 (br d, 2-H), 2.72 (dd, 2-H), 5.11 (br d, 3-H), 3.17 (br d, 4-H), 3.49 (s, 4-$OCH_3$), 3.87 (br d, 5-H ), 0.85 (br dt, 7-H), 1.41 (br dt, 7-H), 1.87 (m, 8-H), 3.88 (dd, 9-H), 5.45 (dd, 10-H), 6.61 (dd, 11-H), 6.06 (br dd, 12-H), 5.82 (ddd, 13-H), 2.15 (dt, 14-H), 4.99 (ddq, 15-H), 1.26 (d, 16-$H_3$), 2.83 (br dd, 17-H), 9.62 (br s, 18-H), 0.98 (d, 19-$H_3$), 2.50 (dq, 3-OCOC$\underline{H}_2$CH$_3$), 2.65 (dq, 3-OCOC$\underline{H}_2$CH$_3$), 1.21 (t, 3-OCOCH$_2$C$\underline{H}_3$), 3.42 (dq, 9-OCH(OC$\underline{H}_2$CH$_3$)CH$_3$), 3.50 (dq, 9-OCH(OC$\underline{H}_2$CH$_3$)CH$_3$), 1.14 (t, 9-OCH(OCH$_2$C$\underline{H}_3$)CH$_3$), 1.22 ( d, 9-OCH(OCH$_2$CH$_3$)CH$_3$), 4.60 (d, 1'-H), 4.92 (dd, 2'-H), 2.68 (t, 3'-H), 3.16 (t, 4'-H), 3.26 (dq, 5'-H), 1.14 (d, 6'-$H_3$), 2.01 (s, 2'-OCOCH$_3$), 2.43 (s, 3'-N(CH$_3$)$_2$), 4.81 (d, 1"-H), 1.68 (dd, 2"-Hax), 2.25 (d, 2"-Heq), 1.17 (s, 3"-CH$_3$), 4.56 (dq, 5"-H), 1.05 (d, 6"-$H_3$), 4.51 (d, 3"-OC$\underline{H}_2$SCH$_3$), 4.64, 4.65 (2×d, 4"-H, 3"-OCH$_2$SC$\underline{H}_3$), 2.20 (s, 3"-OCH$_2$SC$\underline{H}_3$), 2.42 ( q, 4"-OCOC$\underline{H}_2$CH$_3$), 1.18 (t, 4"-OCOCH$_2$C$\underline{H}_3$).

Physicochemical properties of the compound (14L)
 (1) Color and appearance: colorless solid.
 (2) Molecular formula: $C_{49}H_{81}NO_{17}S$.
 (3) Mass spectrum (FDMS): m/z 988 (M+H)$^+$.
 (4) Rf value on TLC: 0.46 [developing system: hexane/ethyl acetate (1:1)].
 (5) Specific rotation: $[\alpha]_D^{19}$ –87° (c 1.0, CHCl$_3$).
 (6) Melting at around 90° to 94° C. without showing any definite melting point.
 (7) $^1$H NMR spectrum (400 MHz, CDCl$_3$) δ (ppm: 2.25 (br d, 2-H), 2.72 (dd, 2-H), 5.11 (br d, 3-H), 3.18 (br d, 4-H), 3.49 (s, 4-OCH$_3$), 3.87 (br d, 5-H), 0.87 (br dt, 7-H), 1.43 (br dt, 7-H), 1.86 (m, 8-H), 3.74 (dd, 9-H), 5.54 (dd, 10-H), 6.58 (dd, 11-H), 6.06 (br dd, 12-H), 5.80 (ddd, 13-H), 2.15 (dt, 14-H), 5.00 (ddq, 15-H), 1.26 (d, 16-H$_3$), 2.84 (br dd, 17-H), 9.63 (br s, 18-H), 0.98 (d, 19-H$_3$), 2.52 (dq, 3-OCOCH$_2$CH$_3$), 2.65 (dq, 3-OCOCH$_2$CH$_3$), 1.23 (t, 3-OCOCH$_2$CH$_3$), 4.65 (q, 9-OCH(OCH$_2$CH$_3$)CH$_3$), 3.35 (dq, 9-OCH(OCH$_2$CH$_3$)CH$_3$), 3.63 (dq, 9-OCH(OCH$_2$CH$_3$)CH$_3$), 1.14 (t, 9-OCH(OCH$_2$CH$_3$)CH$_3$), 1.25 (d, 9-OCH(OCH$_2$CH$_3$)CH$_3$), 4.60 (d, 1'-H), 4.92 (dd, 2'-H), 2.68 (t, 3'-H), 3.16 (t, 4'-H), 3.26 (dq, 5'-H), 1.14 (d, 6'-H$_3$), 2.01 (s, 2'-OCOCH$_3$), 2.43 (s, 3'-N(CH$_3$)$_2$), 4.81 (d, 1''-H), 1.69 (dd, 2''-Hax), 2.26 (d, 2''-Heq), 1.17 (s, 3''-CH$_3$), 4.57 (dq, 5''-H), 1.05 (d, 6''-H$_3$), 4.51 (d, 3''-OCH$_2$SCH$_3$), 4.64, 4.65 (2×d, 4''-H, 3''-OCH$_2$SCH$_3$), 2.20 (s, 3''-OCH$_2$SCH$_3$), 2.42 (q, 4''-OCOCH$_2$CH$_3$), 1.18 (t, 4''-OCOCH$_2$CH$_3$).

EXAMPLE 14

Process for producing compound (15H) [a compound represented by the formula (XVIII) wherein R$^1$ represents a propionyl group, R$^2$ represents a 1-ethoxyethyl group and R$^4$ represents a propionyl group, which is an isomer derived from the compound (14H)]:

Fifty mg of the compound (14H) was dissolved in 1.5 ml of methanol and the resulting mixture was allowed to react at 30° C. for 16 hours. The reaction mixture was concentrated under reduced pressure and 47 mg of the thus obtained residue was purified by preparative TLC [developing system: hexane/ethyl acetate (1:1)]. Thus 36 mg of the compound (15H) was obtained.

Physicochemical properties of the compound (15H)
 (1) Color and appearance: colorless solid.
 (2) Molecular formula: $C_{47}H_{79}NO_{16}S$.
 (3) Mass spectrum (SIMS): m/z 946 (M+H)$^+$.
 (4) Rf value on TLC: 0.24 [developing system: hexane/ethyl acetate (1:1)].
 (5) Specific rotation: $[\alpha]_D^{19}$ –55° (c 1.0, CH$_3$OH).
 (6) Melting at around 95° to 98° C. without showing any definite melting point.
 (7) $^1$H NMR spectrum (400 MHz, CDCl$_3$) δ (ppm: 2.26 (br d, 2-H), 2.75 (dd, 2-H), 5.13 (br d, 3-H), 3.26 (br d, 4-H), 3.57 (s, 4-OCH$_3$), 3.88 (br d, 5-H), 0.93 (br ddd, 7-H), 1.53 (br dt, 7-H), 1.89 (m, 8-H), 3.90 (dd, 9-H), 5.46 (dd, 10-H), 6.62 (dd, 11-H), 6.10 (br dd, 12-H), 5.83 (ddd, 13-H), 5.01 (ddq, 15-H), 2.85 (br dd, 17-H), 9.63 (br s, 18-H), 0.98 (d, 19-H$_3$), 2.51 (dq, 3-OCOCH$_2$CH$_3$), 2.64 (dq, 3-OCOCH$_2$CH$_3$), 4.64 (q, 9-OCH(OCH$_2$CH$_3$)CH$_3$), 3.43 (dq, 9-OCH(OCH$_2$CH$_3$)CH$_3$), 3.50 (dq, 9-OCH(OCH$_2$CH$_3$)CH$_3$), 4.51 (d, 1'-H), 3.41 (t, 4'-H), 3.28 (dq, 5'-H), 2.58 (s, 3'-N(CH$_3$)$_2$), 4.92 (d, 1''-H), 1.75 (dd, 2''-Hax), 2.28 (d, 2''-Heq), 4.56 (dq, 5''-H), 1.08 (d, 6''-H$_3$), 4.52 (d, 3''-OCH$_2$SCH$_3$), 4.65, 4.66 (2×d, 4''-H, 3''-OCH$_2$SCH$_3$), 2.19 (s, 3''-OCH$_2$SCH$_3$), 2.42 (q, 4''-OCOCH$_2$CH$_3$).

EXAMPLE 15

Process for producing compound (15L) [a compound represented by the formula (XVIII) wherein R$^1$ represents a propionyl group, R$^2$ represents a 1-ethoxyethyl group and R$^4$ represents a propionyl group, which is an isomer derived from the compound (14L)]:

To 6.8 ml of methanol was dissolved 230 mg of the compound (14L) followed by the reaction at 30° C. for 16 hours. The reaction mixture was concentrated under reduced pressure and 204 mg of the thus obtained residue was purified by preparative TLC [developing system: hexane/ethyl acetate (1:1)]. Thus 150 mg of the compound (15L) was obtained.

Physicochemical properties of the compound (15L)
 (1) Color and appearance: colorless solid.
 (2) Molecular formula: $C_{47}H_{79}NO_{16}S$.
 )3) Mass spectrum (SIMS): m/z 946 (M+H)$^+$.
 (4) Rf value on TLC: 0.16 [developing system: hexane/ethyl acetate (1:1)].
 (5) Specific rotation: $[\alpha]_D^{19}$ –73° (c 1.0, CH$_3$OH).
 (6) Melting at around 91° to 93° C. without showing any definite melting point.
 (7) $^1$H NMR spectrum (400 MHz, CDCl$_3$) δ (ppm: 2.26 (br d, 2-H), 2.75 (dd, 2-H), 5.13 (br d, 3-H), 3.26 (br d, 4-H), 3.57 (s, 4-OCH$_3$), 3.88 (br d, 5-H), 0.94 (br ddd, 7-H), 1.53 (br dt, 7-H), 1.88 (m, 8-H), 3.76 (dd, 9-H), 5.55 (dd, 10-H), 6.59 (dd, 11-H), 6.09 (br dd, 12-H), 5.80 (ddd, 13-H), 5.02 (ddq, 15-H), 2.25 (br dd, 17-H), 2.85 (br dd, 17-H), 9.64 (br s, 18-H), 2.52 (dq, 3-OCOCH$_2$CH$_3$), 2.65 (dq, 3-OCOCH$_2$CH$_3$), 3.36 (dq, 9-OCH(OCH$_2$CH$_3$)CH$_3$), 3.63 (dq, 9-OCH(OCH$_2$CH$_3$)CH$_3$), 4.51 (d, 1'-H), 3.41 (t, 4'-H), 3.28 (dq, 5'-H), 2.59 (s, 3'-N(CH$_3$)$_2$), 4.92 (d, 1''-H), 1.75 (dd, 2''-Hax), 2.28 (d, 2''-Heq), 4.56 (dq, 5''-H), 1.08 (d, 6''-H$_3$), 4.52 (d, 3''-OCH$_2$SCH$_3$), 4.65, 4.66 (233 d, 4''-H, 3''-OCH$_2$SCH$_3$), 2.19 (s, 3''-OCH$_2$SCH$_3$), 2.42 ( q, 4''-OCOCH$_2$CH$_3$).

EXAMPLE 16

Process for producing compound (16H) [a compound represented by the formula (XIX) wherein R$^1$ represents a propionyl group, R$^2$ represents a 1-ethoxyethyl group and R$^4$ represents a propionyl group, which is an isomer derived from the compound (15H)]:

Thirty mg of the compound (15H) was dissolved in 0.35 ml of ethanol. The activity of 0.75 ml of Raney nickel was controlled in the same manner as in Example 7 and it was added to the above mixture together with 0.40 ml of ethanol. After the resulting mixture was stirred vigorously at room temperature for 20 minutes, insoluble matters were filtered and washed with 1.5 ml portions of ethanol containing 1% (v/v) conc. aqueous ammonia twice. The filtrate and washings were combined and concentrated under reduced pressure. Then, 28 mg of the thus obtained residue was purified by preparative TLC [developing system: toluene/acetone (2:1)]to obtain 10 mg of the compound (16H).

Physicochemical properties of the compound (16H)
 (1) Color and appearance: colorless solid.
 (2) Molecular formula: $C_{46}H_{77}NO_{16}$.
 (3) Mass spectrum (SIMS): m/z 900 (M+H)$^+$.
 (4) Rf value on TLC: 0.32 [developing system: toluene/acetone (3:1)].
 (5) Specific rotation: $[\alpha]_D^{19}$ –43° (c 1.0, CH$_3$OH).
 (6) Melting at around 90° to 93° C. without showing any definite melting point.
 (7) $^1$H NMR spectrum (400 MHz, CDCl$_3$) δ (ppm: 2.26 (br d, 2-H), 2.74 (dd, 2-H), 5.13 (br d, 3-H), 3.26 (br d, 4-H), 3.57 (s, 4-OCH$_3$), 3.88 (br d, 5-H), 2.13 (br t, 6-H), 0.93 (br ddd, 7-H), 1.54 (br dt, 7-H), 1.89 (m, 8-H), 3.90 (dd, 9-H), 5.46 (dd, 10-H), 6.62 (dd, 11-H), 6.10 (br dd, 12-H), 5.83

(ddd, 13-H), 2.17 (dt, 14-H), 5.00 (ddq, 15-H), 1.26 (d, 16-H$_3$), 2.28 (br dd, 17-H), 2.85 (br dd, 17-H), 9.64 (br s, 18-H), 0.98 (d, 19-H$_3$), 2.50 (dq, 3-OCOCH$_2$CH$_3$), 2.64 (dq, 3-OCOCH$_2$CH$_3$), 1.23 (t, 3-OCOCH$_2$CH$_3$), 4.64 (q, 9-OC$\underline{H}$(OCH$_2$CH$_3$)CH$_3$), 3.43 (dq, 9-OC$\overline{H}$(OCH$_2$CH$_3$)CH$_3$), 3.50 (dq, 9-OCH(OCH$_2$CH$_3$)CH$_3$), 1.14 (t, 9-$\overline{OC}$H(OCH$_2$C$\underline{H}_3$)CH$_3$), 1.22 (d, 9-$\overline{OC}$H(OCH$_2$CH$_3$)CH$_3$) 4.53 (d, 1'-H), 3.46 (t, 4'-H), 3.29 (dq, 5'-H), 1.16 (d, 6'-H$_3$), 2.60 (s, 3'-N(CH$_3$)$_2$), 4.93 (d, 1''-H), 1.67 (dd, 2''-Hax), 2.29 (d, 2''-Heq), 1.11 (s, 3''-CH$_3$), 4.73 (d, 4''-H), 4.54 (dq, 5''-H), 1.08 (d, 6''-H$_3$), 3.26 (s, 3''-OCH$_3$), 2.43 (apparent q, 4''-OCOC$\underline{H}_2$CH$_3$), 2.44 (apparent q, 4''-OCOCH$_2$CH$_3$), 1.20 (t, 4''-OCO$\overline{C}$H$_2$C$\underline{H}_3$).

EXAMPLE 17

Process for producing compound (16L) [a compound represented by the formula (XIX) wherein R$^1$ represents a propionyl group, R$^2$ represents a 1-ethoxyethyl group and R$^4$ represents a propionyl group, which is an isomer derived from the compound (15L)]:

In 2.0 ml of ethanol was dissolved 150 mg of the compound (15L). The activity of 3.8 ml of Raney nickel was controlled in the same manner as in Example 7 and it was added to the above mixture together with 1.8 ml of ethanol. After the resulting mixture was stirred vigorously at room temperature for 20 minutes, insoluble matters were filtered and washed with 4.0 ml portions of ethanol containing 1% (v/v) conc. aqueous ammonia twice. The filtrate and washings were combined and concentrated under reduced pressure. Then, 145 mg of the thus obtained residue was purified by preparative TLC [developing system: toluene/acetone (2:1)] to obtain 32 mg of the compound (16L).

Physicochemical properties of the compound (16L)

(1) Color and appearance: colorless solid.
(2) Molecular formula: C$_{46}$H$_{77}$NO$_{16}$.
(3) Mass spectrum (SIMS): m/z 900 (M+H)$^+$.
(4) Rf value on TLC: 0.32 [developing system: toluene/acetone (3:1)].
(5) Specific rotation: $[\alpha]_D^{19}$ –65° (c 1.0, CH$_3$OH).
(6) Melting at around 87° to 90° without showing any definite melting point.
(7) $^1$H NMR spectrum (400 MHz, CDCl$_3$) δ (ppm: 2.26 (br d, 2-H), 2.75 (dd, 2-H), 5.13 (br d, 3-H), 3.26 (br d, 4-H), 3.57 (s, 4-OCH$_3$), 3.88 (br d, 5-H), 2.13 (br t, 6-H), 0.94 (br ddd, 7-H), 1.55 (br dt, 7-H), 1.88 (m, 8-H), 3.75 (dd, 9-H), 5.55 (dd, 10-H), 6.59 (dd, 11-H), 6.09 (br dd, 12-H), 5.80 (ddd, 13-H), 2.16 (dt, 14-H), 5.01 (ddq, 15-H), 1.26 (d, 16-H$_3$), 2.25 (br dd, 17-H), 2.86 (br dd, 17-H), 9.64 (br s, 18-H), 2.52 (dq, 3-OCOCH$_2$CH$_3$), 2.64 (dq, 3-OCOC$\underline{H}_2$CH$_3$), 1.23 (t, 3-OCOC$\overline{H}_2$C$\underline{H}_3$), 3.36 (dq, 9-OCH(OC$\underline{H}_2$CH$_3$)CH$_3$), 3.63 (dq, 9-OC$\overline{H}$(OCH$_2$CH$_3$)CH$_3$), 1.14 (t, 9-OCH(OCH$_2$C$\underline{H}_3$)CH$_3$), 1.25 (d, $\overline{9}$-OCH(OCH$_2$CH$_3$)C$\underline{H}_3$), 4.52 (d, 1'-$\overline{H}$), 3.21 (dd, 2'-H), 2.42 (t, 3'-H), 3.45 (t, $\overline{4'}$-H), 3.29 (dq, 5'-H), 1.16 (d, 6'-H$_3$), 2.57 (s, 3'-N(CH$_3$)$_2$), 4.92 (d, 1''-H), 1.67 (dd, 2''-Hax), 2.29 (d, 2''-Heq), 1.10 (s, 3''-CH$_3$), 4.72 (d, 4''-H), 4.55 (dq, 5''-H), 1.08 (d, 6''-H$_3$), 3.26 (s, 3''-OCH$_3$), 2.43 (apparent q, 4''-OCOC$\underline{H}_2$CH$_3$), 2.44 (apparent q, 4''-OCOC$\underline{H}_2$CH$_3$), 1.18 (t, 4''-OC$\overline{O}$CH$_2$C$\underline{H}_3$).

EXAMPLE 18

Process (2) for producing compound (1) [a compound represented by the formula (I) wherein R$^1$ represents a propionyl group, R$^2$ represents a hydrogen atom, R$^3$ represents a hydrogen atom and R$^4$ represents a propionyl group] (3''-O-methylmidecamycin A$_1$):

Sixty mg of the compound (16H) was dissolved in a mixed solution of 4.5 ml of a 5% solution of acetic acid and 1.5 ml of acetonitrile and the mixture was allowed to react at room temperature for 16 hours. After the reaction mixture was concentrated under reduced pressure, the resulting residue was dissolved in 10 ml of chloroform and washed with 10 ml portions of a saturated sodium hydrogencarbonate solution three times and 10 ml of a saturated sodium chloride solution. The chloroform layer was dried over anhydrous sodium sulfate and filtered. The filtrate was concentrated under reduced pressure and 56 mg of the residue thus obtained was purified by preparative TLC [developing system: chloroform/methanol (10:1)]. Thus 50 mg of the compound (1) was obtained.

EXAMPLE 19

Process (3) for producing compound (1) [a compound represented by the formula (I) wherein R$^1$ represents a propionyl group, R$^2$ represents a hydrogen atom, R$^3$ represents a hydrogen atom and R$^4$ represents a propionyl group] (3''-O-methylmidecamycin A$_1$):

Thirty mg of the compound (16L) was dissolved in a mixed solution of 2.4 ml of a 5% solution of acetic acid and 0.8 ml of acetonitrile and the mixture was allowed to react at room temperature for 16 hours. After the reaction mixture was concentrated under reduced pressure, the resulting residue was dissolved in 5.0 ml of chloroform and washed with 5.0 ml portions of a saturated sodium hydrogencarbonate solution three times and 5.0 ml of a saturated sodium chloride solution. The chloroform layer was dried over anhydrous sodium sulfate and filtered. The filtrate was concentrated under reduced pressure and 28 mg of the residue thus obtained was purified by preparative TLC [developing system: chloroform/methanol (10:1)]. Thus 24 mg of the compound (1) was obtained.

EXAMPLE 20

Process for producing compound (17) [a compound represented by the formula (XV) wherein R$^1$ represents an acetyl group, R$^2$ represents a 1-ethoxyethyl group and R$^4$ represents an isovaleryl group]:

Ten g of josamycin was dissolved in a mixed solution of 300 ml of methylene chloride and 16 ml of ethyl vinyl ether. After adding 5.4 g of PPTS thereto, the resulting mixture was allowed to react at room temperature for 4 days. The reaction mixture was added to 1.0 liter of a saturated sodium hydrogencarbonate solution by slow degrees followed by extraction with 0.80 liter of chloroform. The chloroform layer was washed subsequently with 1.0 liter of a 5% potassium hydrogensulfate solution, 1.0 liter of a saturated sodium hydrogencarbonate solution and 1.0 liter of a saturated sodium chloride solution. The chloroform layer was dried over anhydrous sodium sulfate and filtered. Then the filtrate was concentrated under reduced pressure and 12 g of the residue thus obtained was purified by silica gel column chromatography [600 g: chloroform/methanol (50:1)]. Thus 8.4 g of the compound (17) was obtained.

Physicochemical properties of the compound (17)

(1) Color and appearance: colorless solid.
(2) Molecular formula: C$_{46}$H$_{77}$NO$_{16}$.
(3) Mass spectrum (EIMS): m/z 899 (M)$^+$.
(4) Specific rotation: $[\alpha]_D^{16}$ –68° (c 1.0, CH$_3$OH).
(5) m.p.: melting at around 105° to 108° C. without showing any definite melting point.
(6) $^1$H NMR spectrum (400 MHz, CDCl$_3$) δ (ppm: 2.73 (dd, 2-H), 2.75 (dd, 2-H), 5.12 (br d, 3-H), 3.24 (br d, 4-H), 3.54 (s, 4-OCH$_3$), 3.90 (br d, 5-H), 1.45 (br dt, 7-H), 1.90 (m, 8-H), 3.75 (dd, 9-H), 3.89 (dd, 9-H), 5.46 (dd, 10-H), 5.55 (dd, 10-H), 6.56 (dd, 11-H), 6.58 (dd, 11-H), 6.08 (br dd, 12-H), 5.76 (ddd, 13-H), 5.81 (ddd, 13-H), 5.04 (ddq, 15-H), 1.27 (d, 16-H$_3$), 2.84 (br dd, 17-H), 2.85 (br dd, 17-H), 9.64 (s, 18-H), 9.65 (s, 18-H), 0.98 (d, 19-H$_3$), 0.99 (d, 19-H$_3$), 4.63 (q, 9-OCH(OCH$_2$CH$_3$)CH$_3$), 4.64 (q, 9-OCH(OCH$_2$CH$_3$)CH$_3$), 3.35 (dq, 9-OCH(OCH$_2$CH$_3$)CH$_3$), 3.42 (dq, 9-OCH(OCH$_2$CH$_3$)CH$_3$), 3.63 ( d, 9-OCH (OCH$_2$CH$_3$)CH$_3$), 1,14 (t, 9-OCH(OCH$_2$CH$_3$CH$_3$)CH$_3$), 1.23 (d, 9-OCH (OCH$_2$CH$_3$)CH$_3$), 1.25 (d, 9-OCH(OCH(OCH$_2$CH$_3$)CH$_3$), 4.43 (d, 1'-H), 3.28 (t, 4'-H), 1.19 (d, 6'-H$_3$), 2.52 (s, 3'-N(CH$_3$)$_2$), 5.07 (d, 1"-H), 1.85 (dd, 2"-Hax), 2.02 (d, 2"-Heq), 1.12 (s, 3"-CH$_3$), 4.63 (d, 4"-H), 4.46 (dq, 5"-H), 1.14 (d, 6"-H$_3$), 0.98 (d, 4"-OCOCH$_2$CH(CH$_3$)$_2$).

EXAMPLE 21

Process for producing compound (18) [a compound represented by the formula (XVI) wherein R$^1$ represents an acetyl group, R$^2$ represents a 1-ethoxyethyl group and R$^4$ represents an isovaleryl group]:

In 231 ml of acetonitrile was dissolved in 7.7 g of the compound (17) and 1.6 ml of acetic anhydride was added thereto, followed by the reaction at 40° C. for 16 hours. Then 25 ml of a 1N aqueous ammonia was dropped into the reaction mixture and allowed to stand at room temperature for 10 minutes. After the reaction mixture was concentrated under reduced pressure, the resulting residue was dissolved in 800 ml of chloroform and successively washed with 800 ml of a saturated aqueous solution of sodium hydrogencarbonate and 800 ml of a saturated aqueous solution of sodium chloride. Then the chloroform layer was dried over anhydrous sodium sulfate and filtered. The filtrate was concentrated under reduced pressure and 7.9 g of the thus obtained residue was purified by silica gel column chromatography [700 g: hexane/ethyl acetate (1:1)]. Thus 5.1 g of the compound (18) was obtained.

Physicochemical properties of the compound (18)
(1) Color and appearance: colorless solid.
(2) Molecular formula: C$_{48}$H$_{79}$NO$_{17}$.
(3) Mass spectrum (FDMS): m/z 942 (M+H)$^+$.
(4) Specific rotation: [α]$_D^{19}$–70° (c 1.0, CHCl$_3$).
(5) Melting at around 110° to 113° C. without showing any definite melting point.
(6) $^1$H NMR spectrum (400 MHz, CDCl$_3$) δ (ppm: 2.25 (br d, 2-H), 2.72 (dd, 2-H), 5.10 (br d, 3-H), 3.18 (br d, 4-H), 3.49 (s, 4-OCH$_3$), 3.91 (br d, 5-H), 0.86 (br ddd, 7-H), 1.43 (br dt, 7-H), 3.72 (dd, 9-H), 3.86 (dd, 9-H), 5.46 (dd, 10-H), 5.54 (dd, 10-H), 6.55 (dd, 11-H), 6.58 (dd, 11-H), 6.05 (br dd, 12-H), 5.76 (ddd, 13-H), 5.81 (ddd, 13-H), 2.12 (dt, 14-H), 2.45 (br dt, 14-H), 5.01 (ddq, 15-H), 1.26 (d, 16-H$_3$), 2.83 (br dd, 17-H), 9.63 (s, 18-H), 9.64 (s, 18-H), 2.29 (s, 3-OCOCH$_3$), 3.34 (dq, 9-OCH(OCH$_2$CH$_3$)CH$_3$), 3.41 (dq, 9-OCH (OCH$_2$CH$_3$)CH$_3$), 3.63 (dq, 9-OCH(OCH$_2$CH$_3$)CH$_3$), 1.14 (t, 9-OCH (OCH$_2$CH$_3$)CH$_3$), 1.22 (d, 9-OCH(OCH$_2$CH$_3$)CH$_3$), 1.24 (d, 9-OCH(OCH$_2$CH$_3$)CH$_3$), 4.99 (dd, 2'-H), 2.69 (t, 3'-H), 1.18 (d, 6'-H$_3$), 2.02 (s, 2'-OCOCH$_3$), 2.41 (s, 3'-N(CH$_3$)$_2$), 5.06 (d, 1"-H), 1.84 (dd, 2"-Hax), 2.01 (d, 2"-Heq), 1.12 (s, 3"-CH$_3$), 4.38 (dq, 5"-H), 1.13 (d, 6"-H$_3$), 0.98 (d, 4"-OCOCH$_2$CH(CH$_3$)$_2$).

EXAMPLE 22

Process for producing compound (19) [a compound represented by the formula (XVII) wherein R$^1$ represents an acetyl group, R$^2$ represents a 1-ethoxyethyl group and R$^4$ represents an isovaleryl group]:

In a mixed solution of 150 ml of DMSO and 15 ml of acetic anhydride was dissolved 5.00 g of of the compound (18) and the mixture was allowed to react at 30° C. for 40 hours. Then the reaction mixture was dropped into 1.0 liter of toluene by slow degrees and washed with 1.0 liter of water three times. The toluene layer was dried over anhydrous sodium sulfate and filtered. The filtrate was concentrated under reduced pressure and 6.41 g of the residue thus obtained was purified by silica gel column chromatography [500 g: hexane/ethyl acetate (1:1)]. Thus 2.25 g of the compound (19) was obtained.

Physicochemical properties of the compound (19)
(1) Color and appearance: colorless solid.
(2) Molecular formula: C$_{50}$H$_{83}$NO$_{17}$S.
(3) Mass spectrum (FDMS): m/z 1002 (M+H)$^+$.
(4) Specific rotation: [α]$_D^{16}$–87° (c 1.0, CHCl$_3$).
(5) Melting at around 102° to 105° C. without showing any definite melting point.
(6) $^1$H NMR spectrum (400 MHz, CDCl$_3$) δ (ppm: 2.25 (br d, 2-H), 2.72 (dd, 2-H), 2.73 (dd, 2-H), 5.10 (br d, 3-H), 3.18 (br d, 4-H), 3.50 (s, 4-OCH$_3$), 3.51 (s, 4- OCH$_3$), 3.89 (br d, 5-H), 0.85 (br ddd, 7-H), 1.43 (br dt, 7-H), 1.87 (m, 8-H), 3.73 (dd, 9-H), 3.86 (dd, 9-H), 5.45 (dd, 10-H), 5.54 (dd, 10-H), 6.54 (dd, 11-H), 6.58 (dd, 11-H), 6.05 (br dd, 12-H), 5.76 (ddd, 13-H), 5.82 (ddd, 13H), 2.15 (dt, 14-H), 2.45 (br dt, 14-H), 5.01 (ddq, 15-H), 1.26 (d, 16-H$_3$), 2.85 (br dd, 17-H), 9.63 (s, 18-H), 9.64 (s, 18-H), 0.99 (d, 19-H$_3$), 3.35 (dq, 9-OCH(OCH$_2$CH$_3$)CH$_3$), 3.41 (dq, 9-OCH(OCH$_2$CH$_3$)CH$_3$), 3.63 (dq, 9-OCH(OCH$_2$CH$_3$)CH$_3$), 1.14 (br t, 9-OCH(OCH$_2$CH$_3$)CH$_3$), 1.22 (d, 9-OCH(OCH$_2$CH$_3$)CH$_3$), 1.24 (d, 9-OCH(OCH$_2$CH$_3$)CH$_3$), 5.10 (d, 1'-H), 4.93 (dd, 2'-H), 2.68 (t, 3'-H), 3.16 (t, 4'-H), 3.27 (dq, 5'-H), 1.14 (d, 6'-H$_3$), 2.01 (s, 2'-OCOCH$_3$), 2.42 (s, 3'-N(CH$_3$)$_2$), 4.81 (d, 1"-H), 1.68 (dd, 2"-Hax), 1.18 (s, 3"-CH$_3$), 4.57 (dq, 5"-H), 1.05 (d, 6"-H$_3$), 4.50 (d, 3"-OCH$_2$CH$_3$), 4.64, 4.65 (2×d, 4"-H, 3"-OCH$_2$SCH$_3$), 2.20 (s, 3"-OCH$_2$SCH$_3$), 0.98 (d, 4"-OCOCH$_2$CH(CH$_3$)$_2$).

EXAMPLE 23

Process for producing compound (20) [a compound represented by the formula (XVIII) wherein R$^1$ represents an acetyl group, R$^2$ represents a 1-ethoxyethyl group and R$^4$ represents an isovaleryl group]:

In 65 ml of methanol was dissolved 2.2 g of the compound (19) and the resulting mixture was allowed to react at room temperature for 40 hours. The reaction mixture was concentrated under reduced pressure to obtain 2.1 g of the compound (20).

Physicochemical properties of the compound (20)
(1) Color and appearance: colorless solid.
(2) Molecular formula: C$_{48}$H$_{81}$NO$_{16}$S.
(3) Mass spectrum (FDMS): m/z 959 (M)$^+$.
(4) Specific rotation: [α]$_D^{18}$–75° (c 1.0, CH$_3$OH).
(5) Melting at around 105° to 107° C. without showing any definite melting point.
(6) $^1$H NMR spectrum (400 MHz, CDCl$_3$) δ (ppm: 2.26 (br d, 2-H), 2.75 (dd, 2-H), 2.76 (dd, 2-H), 5.11 (br d, 3-H), 3.58 (s, 4-OCH$_3$), 3.91 (br d, 5-H), 0.92 (br ddd, 7-H), 1.54 (br dt, 7-H), 1.89 (m, 8-H), 3.73 (dd, 9-H), 3.88 (dd, 9-H), 5.46 (dd, 10-H), 5.55 (dd, 10-H), 6.56 (dd, 11-H), 6.60 (dd, 11-H), 6.09 (br dd, 12-H), 5.77 (ddd, 13-H), 5.82 (ddd, 13-H), 2.13 (dr, 14-H), 2.46 (br dt, 14-H), 5.03 (ddq, 15-H), 1.27 (d, 16-H$_3$), 2.88 (br dd, 17-H), 9.64 (s, 18-H), 9.65 (s, 18-H), 2.28 (s, 3-OCOCH$_3$), 3.35 (dq, 9-OCH(OCH$_2$CH$_3$)CH$_3$), 3.41 (dq, 9-OCH(OCH$_2$CH$_3$)CH$_3$), 3.49 (dq, 9-OCH(OCH$_2$CH$_3$)CH$_3$), 3.63 (dq, 9-OCH(OCH$_2$CH$_3$)CH$_3$), 1.14 (br t, 9-OCH(OCH$_2$CH$_3$)CH$_3$), 1.22 (d, 9-OCH(OCH$_2$CH$_3$)CH$_3$), 1.24 (d, 9-OCH(OCH$_2$CH$_3$)CH$_3$), 4.51 (d, 1'-H), 1.15 (d, 6'-H$_3$), 2.57 (s, 3'-N(CH$_3$)$_2$), 4.92 (d, 1"-H), 1.74 (dd, 2"-Hax), 1.20 (s, 3"-CH$_3$), 4.56 (dq, 5"-H), 1.08 (d, 6"-H$_3$), 4.52 (d, 3"-OCH$_2$SCH$_3$), 4.65, 4.66 (2×d, 4"-H, 3"-OCH$_2$SCH$_3$), 2.20 (s, 3"'-OCH$_2$SCH$_3$), 0.98 (d, 4"-OCOCH$_2$CH(CH$_3$)$_2$).

EXAMPLE 24

Process for producing compound (21) [a compound represented by the formula (XIX) wherein R$^1$ represents an acetyl group, R$^2$ represents a 1-ethoxyethyl group and R$^4$ represents an isovaleryl group]:

In 25 ml of ethanol was dissolved 1.00 g of the compound (20). The activity of 25 ml of Raney nickel was controlled in the same manner as in Example 7 and it was added to the above mixture together with 25 ml of ethanol. After the resulting mixture was stirred vigorously at room temperature for 20 minutes, insoluble matters were filtered and washed with 50 ml portions of ethanol containing 1% (v/v) conc. aqueous ammonia twice. The filtrate and washings were combined and concentrated under reduced pressure. Then, 930 mg of the thus obtained residue was purified by silica gel column chromatography [100 g: toluene/acetone (1:1)] to obtain 614 mg of the crude compound (21). This was further purified by silica gel column chromatography [100 g:hexane/ethyl acetate (1:1)] to obtain 360 mg of the compound (21).

Physicochemical properties of the compound (21)
(1) Color and appearance: colorless solid.
(2) Molecular formula: C$_{47}$H$_{79}$NO$_{16}$.
(3) Mass spectrum (SIMS): m/z 914 (M+H)$^+$.
(5) Specific rotation: [α]$_D$$^{16}$–62° (C 1.0, CH$_3$OH).
(6) Melting at around 98° to 101° C. without showing any definite melting point.
(7) $^1$H NMR spectrum (400 MHz, CDCl$_3$) δ (ppm: 2.75 (dd, 2-H), 2.76 (dd, 2-H), 5.12 (br d, 3-H), 3.58 (s, 4-OCH$_3$), 3.91 (br d, 5-H), 1.55 (br dt, 7-H), 1.89 (m, 8-H), 3.73 (dd, 9-H), 3.88 (dd, 9-H), 5.46 (dd, 10-H), 5.55 (dd, 19-H), 6.57 (dd, 11-H), 6.59 (dd, 11-H), 6.09 (br dd, 12-H), 5.77 (ddd, 13-H), 5.82 (ddd, 13-H), 2.13 (dt, 14-H), 2.46 (br dt, 14-H), 5.03 (ddq, 15-H), 1.26 (d, 16-H$_3$), 2.88 (br dd, 17-H), 9.64 (s, 18-H), 9.66 (s, 18-H), 2.28 (s, 3-OCOCH$_3$), 4.63 (q, 9-OCH(OCH$_2$CH$_3$)CH$_3$), 4.64 (dq, 9-OCH(OCH$_2$CH$_3$)CH$_3$), 3.35 (dq, 9-OCH (OCH$_2$CH$_3$)CH$_3$), 3.42 (dq, 9-OCH(OCH$_2$CH$_3$)CH$_3$), 3.50 (dq, 9-OCH (OCH$_2$CH$_3$)CH$_3$), 3.63 (dq, 9-OCH(OCH$_2$CH$_3$)CH$_3$), 1.14 (br t, 9-OCH (OCH$_2$C)CH$_3$), 1.22 (d, 9OCH(OCH$_2$CH$_3$)CH$_3$), 1.24 (d, 9-OCH (OCH$_2$CH$_3$)CH$_3$), 4.52 (d, 1'-H), 3.46 (t, 4'-H), 1.16 (d, 6'-H$_3$), 2.58 (s, 3'-N(CH$_3$)$_2$), 4.93 (d, 1"-H), 1.10 (s, 3"-CH$_3$), 4.73 (d, 4"-H), 4.54 (dq, 5"-H), 1.08 (d, 6"-H$_3$), 3.26 (s, 3"-OCH$_3$), 0.97 (d, 4"-OCOCH$_2$CH(CH$_3$)$_2$).

EXAMPLE 25

Process for producing compound (22) [a compound represented by the formula (I) wherein R$^1$ represents an acetyl group, R$^2$ represents a hydrogen atom, R$^3$ represents a hydrogen atom and R$^4$ represents an isovaleryl group] (3"-O-methyljosamycin):

In a mixed solution of 15 ml of a 5% solution of acetic acid and 5.0 ml of acetonitrile was dissolved 190 mg of the compound (21) and the mixture was allowed to react at room temperature for 16 hours. After the reaction mixture was concentrated under reduced pressure, the resulting residue was dissolved in 20 ml of chloroform and successively washed with 20 ml of a saturated aqueous solution of sodium hydrogencarbonate three times and 20 ml of a saturated aqueous solution of sodium chloride. The chloroform layer was dried over anhydrous sodium sulfate and filtered. The filtrate was concentrated under reduced pressure and 192 mg of the residue thus obtained was purified by preparative TLC [developing system: chloroform/methanol/conc. aqueous ammonia (30:1:0.1)]. Thus 135 mg of the compound (22) was obtained.

Physicochemical properties of the compound (22)
(1) Color and appearance: colorless solid.
(2) Molecular formula: C$_{43}$H$_{71}$NO$_{15}$.
(3) Mass spectrum (SIMS): m/z 842 (M+H)$^+$.
(4) Specific rotation: [α]$_D$$^{17}$–65° (c 1.0, CH$_3$OH).
(5) Melting at around 115° to 117° C. without showing any definite melting point.
(6) $^1$H NMR spectrum (400 MHz, CDCl$_3$) δ (ppm: 2.74 (dd, 2-H), 5.12 (br d, 3-H), 3.26 (br d, 4-H), 3.58 (s, 4-OCH$_3$), 3.90 (br d, 5-H), 0.92 (br ddd, 7-H), 1.58 (br dt, 7-H), 1.89 (m, 8-H), 4.05 (dd, 9-H), 5.62 (dd, 10-H), 6.64 (dd, 11-H), 6.08 (br dd, 12-H), 5.76 (ddd, 13-H), 2.46 (br dt, 14-H), 5.04 (ddq, 15-H), 1.26 (d, 16-H$_3$), 2.33 (br dd, 17-H), 2.88 (br dd, 17-H), 9.64 (s, 18-H), 0.98 (d, 19-H$_3$), 2.28 (s, 3-OCOCH$_3$), 4.52 (d, 1'-H), 3.21 (dd, 2'-H), 2.41 (t, 3'-H), 3.46 (t, 4'-H), 3.29 (dq, 5'-H), 1.16 (d, 6'-H$_3$), 2.57 (s, 3'-N(CH$_3$)$_2$), 4.93 (br d, 1"-H), 1.66 (dd, 2"-Hax), 1.10 (s, 3"-CH$_3$), 4.72 (d, 4"-H), 5.54 (dq, 5"-H), 1.08 (d, 6"-H$_3$), 3.25 (s, 3"-OCH$_3$), 0.97 (d, 4"-OCOCH$_2$CH(CH$_3$)$_2$).

EXAMPLE 26

Process for producing compound (24) [a compound represented by the formula (XVII) wherein R$^1$ represents an acetyl group, R$^2$ represents a propionyl group and R$^4$ represents an isovaleryl group]:

In a mixed solution of 500 ml of DMSO and 50 ml of acetic acid was dissolved 22.0 g of the compound (23) [a compound represented by the formula (XVI) wherein R$^1$ represents an acetyl group, R$^2$ represents a propionyl group and R$^4$ represents an isovaleryl group] (JP-A-49-10515). The resulting mixture was allowed to react at 36° for 16 hours. The reaction mixture was added to 5.0 liter of toluene by slow degrees and washed with 5.0 liter o#water three times the toluene layer was dried over anhydrous sodium sulfate and filtered. The filtrate was concentrated under reduced pressure. Then, 30.0 g of the thus obtained residue was purified by silica gel column chromatography [1.0 kg: toluene/acetone (8:1)→(7:1)] to obtain 9.00 g of the compound (24).

Physicochemical properties of the compound (24)
(1) Color and appearance: colorless solid.
(2) Molecular formula: C$_{49}$H$_{79}$NO$_{17}$S.
(3) Mass spectrum (SIMS): m/z 986 (M+H)$^+$.
(4) Specific rotation: [α]$_D$$^{19}$–90° (c 1.0, CHCl$_3$).
(5) Melting at around 114° to 116° C. without showing any definite melting point.
(6) $^1$H NMR spectrum (400 MHz, CDCl$_3$) δ (ppm: 2.25 (br d, 2-H), 2.71 (dd, 2-H), 5.09 (br d, 3-H), 3.16 (br d, 4-H), 3.49 (s, 4-OCH$_3$), 3.94 (br d, 5-H), 0.85 (br dt, 7-H), 1.46 (br dt, 7-H), 5.05 (dd, 9-H), 5.57 (dd, 10-H), 6.69 (dd, 11-H), 6.05 (br dd, 12-H), 5.85 (ddd, 13-H), 2.45 (br dt, 14-H), 4.98 (ddq, 15-H), 1.26 (d, 16-H$_3$), 2.58 (br dd, 17-H), 2.82 (br dd, 17-H), 9.64 (s, 18-H), 0.95 (d, 19-H$_3$), 2.30 (s, 3-OCOCH$_3$), 1.10 (t, 9-OCOCH$_2$CH$_3$), 4.59 (d, 1'-H), 4.90 (dd, 2'-H), 2.67 (t, 3'-H), 3.16 (t, 4'-H), 3.26 (dq, 5'-H), 1.14 (d, 6'-H$_3$), 2.01 (s, 2'-OCOCH$_3$), 2.42 (s, 3'-N(CH$_3$)$_2$), 4.81

(d, 1"-H), 1.68 (dd, 2"-Hax), 1.18 (s, 3"-CH$_3$), 4.56 (dq, 5"-H), 1.05 (d, 6"-H$_3$), 4.50 (d, 3"'-OCH$_2$SCH$_3$), 4.63, 4.64 (2×d, 4"'-H, 3"'-OCH$_2$SCH$_3$), 2.20 (s, 3"'-OCH$_2$SCH$_3$), 0.98 (d, 4"'-OCOCH$_2$CH(CH$_3$)$_2$).

EXAMPLE 27

Process for producing compound (25) [a compound represented by the formula (XVIII) wherein R$^1$ represents an acetyl group, R$^2$ represents a propionyl group and R$^4$ represents an isovaleryl group]:

In 445 ml of methanol was dissolved 8.90 g of the compound (24) and the resulting mixture was allowed to react at 36° C. for 16 hours. The reaction mixture was concentrated under reduced pressure to obtain 7.80 g of the compound (25).

Physicochemical properties of the compound (25)
(1) Color and appearance: colorless solid.
(2) Molecular formula: C$_{47}$H$_{77}$NO$_{16}$S.
(3) Mass spectrum (SIMS): m/z 944 (M+H)$^+$.
(4) Specific rotation: [α]$_D^{16}$ –58° (c 1.0, CH$_3$OH).
(5) Melting at around 113° to 116° C. without showing any definite melting point.
(6) $^1$H NMR spectrum (400 MHz, CDCl$_3$) δ (ppm: 2.26 (br d, 2-H), 2.75 (dd, 2-H), 5.10 (br d, 3-H), 3.25 (br d, 4-H), 3.57 (s, 4-OCH$_3$), 3.96 (br d, 5-H), 0.92 (br dt, 7-H), 1.57 (br dt, 7-H), 2.03 (m, 8-H), 5.07 (dd, 9-H), 5.58 (dd, 10-H), 6.71 (dd, 11-H), 6.09 (br dd, 12-H), 5.86 (ddd, 13-H), 2.46 (br dt, 14-H), 5.00 (ddq, 15-H), 1.26 (d, 16-H$_3$), 2.62 (br dd, 17-H), 2.84 (br dd, 17-H), 9.66 (s, 18-H), 0.95 (d, 19-H$_3$), 2.29 (s, 3-OCOCH$_3$), 1.10 (t, 9-OCOCH$_2$CH$_3$), 4.49 (d, 1'-H), 3.21 (dd, 2'-H), 2.42 (t, 3'-H), 3.42 (t, 4'-H), 3.28 (dq, 5'-H), 1.15 (d, 6'-H$_3$), 2.57 (s, 3'-N(CH$_3$)$_2$), 4.92 (d, 1"-H), 1.74 (dd, 2"-Hax), 1.20 (s, 3"-CH$_3$), 4.55 (dq, 5"-H), 1.08 (d, 6"-H$_3$), 4.52 (d, 3"'-OCH$_2$SCH$_3$), 4.64, 4.66 (2×d, 4"'-H, 3"'-OCH$_2$SCH$_3$), 2.19 (s, 3"'-OCH$_2$SCH$_3$), 0.98 (d, 4"'-OCOCH$_2$CH(CH$_3$)$_2$).

EXAMPLE 28

Process for producing compound (26) [a compound represented by the formula (I) wherein R$^1$ represents an acetyl group, R$^2$ represents a propionyl group, R$^3$ represents a hydrogen atom and R$^4$ represents an isovaleryl group] (9-O-propionyl-3"-Omethyljosamycin):

In 35 ml of ethanol was dissolved 1.50 g of the compound (25). The activity of 38 ml of Raney nickel was controlled in the same manner as in Example 7 and it was added to the above mixture together with 40 ml of ethanol. After the resulting mixture was stirred vigorously at room temperature for 20 minutes, insoluble matters were filtered and washed with 50 ml portions of ethanol containing 1% (v/v) conc. aqueous ammonia twice. The filtrate and washings were combined and concentrated under reduced pressure. Then, 1.00 g of the thus obtained residue was purified by silica gel column chromatography [100 g: hexane/ethyl acetate (1:1)] to obtain 220 mg of the compound (26).

Physicochemical properties of the compound (26)
(1) Color and appearance: colorless solid.
(2) Molecular formula: C$_{46}$H$_{75}$NO$_{16}$.
(3) Mass spectrum (SIMS): m/z 898 (M+H)$^+$.
(5) Specific rotation: [α]$_D^{15}$ –61° (c 1.0, CH$_3$OH).
(6) Melting at around 115° to 118° C. without showing any definite melting point.
(7) $^1$H NMR spectrum (400 MHz, CDCl$_3$) δ (ppm: 2.26 (br d, 2-H), 2.75 (dd, 2-H), 5.11 (br d, 3-H), 3.24 (br d, 4-H), 3.58 (s, 4-OCH$_3$), 3.96 (br d, 5-H), 0.92 (br dt, 7-H), 1.58 (br dt, 7-H), 2.03 (m, 8-H), 5.07 (dd, 9-H), 5.58 (dd, 10-H), 6.71 (dd, 11-H), 6.09 (br dd, 12-H), 5.86 (ddd, 13-H), 2.17 (dt, 14-H), 2.46 (br dt, 14-H), 5.00 (ddq, 15-H), 1.26 (d, 16-H$_3$), 2.62 (br dd, 17-H), 2.85 (br dd, 17-H), 9.66 (s, 18-H), 0.95 (d, 19-H$_3$), 2.29 (s, 3-OCOCH$_3$), 1.11 (t, 9-OCOCH$_2$CH$_3$), 4.51 (d, 1'-H), 3.19 (dd, 2'-H), 2.41 (t, 3'-H), 3.45 (t, 4'-H), 3.29 (dq, 5'-H), 1.16 (d, 6'-H$_3$), 2.57 (s, 3'-N(CH$_3$)$_2$), 4.93 (d, 1"-H), 1.67 (dd, 2"-Hax), 1.11 (s, 3"-CH$_3$), 4.73 (d, 4"-H), 4.54 (dq, 5"-H), 1.08 (d, 6"-H$_3$), 3.26 (s, 3"-OCH$_3$), 0.97 (d, 4"-OCOCH$_2$CH(CH$_3$)$_2$).

EXAMPLE 29

Process for producing compound (27) [a compound represented by the formula (I) wherein R$^1$ represents a propionyl group, R$^2$ represents a propionyl group, R$^3$ represents a hydrogen atom and R$^4$ represents a propionyl group] (9-O-propionyl-3"-O-methylmidecamycin A$_1$):

Twenty mg of the compound (1) was added to 1.0 ml of anhydrous toluene to dissolve it therein and 8.4 µl anhydrous pyridine was added thereto followed by stirring at room temperature for 20 minutes. To the reaction mixture was added 10 ml of ethyl acetate and 7.8 µl of triethylamine for extraction. The ethyl acetate layer was washed with 10 ml portions of water twice, dried over anhydrous sodium sulfate and filtered. The filtrate was concentrated under reduced pressure and 28 mg of the residue thus obtained was purified by preparative TLC [developing system: chloroform/methanol/conc. aqueous ammonia (30:1:0.1)]. Thus 13 mg of the compound (27) was obtained.

Physicochemical properties of the compound (27)
(1) Color and appearance: colorless solid.
(2) Molecular formula: C$_{45}$H$_{73}$NO$_{16}$.
(3) Mass spectrum (EIMS): m/z 883 (M)$^+$.
(4) Specific rotation: [α]$_D^{22}$ –72° (c 1.0, CH$_3$OH).
(5) Melting at around 114° to 117° C. without showing any definite melting point.
(6) $^1$H NMR spectrum (400 MHz, CDCl$_3$) δ (ppm: 2.26 (br d, 2-H), 2.74 (dd, 2-H), 5.12 (br d, 3-H), 3.24 (br d, 4-H), 3.56 (s, 4-OCH$_3$), 3.94 (br d, 5-H), 0.90 (br ddd, 7-H), 1.57 (br dt, 7-H), 2.02 (m, 8-H), 5.09 (dd, 9-H), 5.58 (dd, 10-H), 6.74 (dd, 11-H), 6.09 (br dd, 12-H), 5.88 (ddd, 13-H), 2.17 (dt, 14-H), 4.98 (ddq, 15-H), 1.26 (d, 16-H$_3$), 2.60 (br dd, 17-H), 2.83 (br dd, 17-H), 9.65 (br s, 18-H), 0.96 (d, 19-H$_3$), 2.51 (dq, 3-OCOCH$_2$CH$_3$), 2.68 (dq, 3-OCOCH$_2$CH$_3$), 1.21 (t, 3-OCOCH$_2$CH$_3$), 2.30 (q, 9-OCOCH$_2$CH$_3$), 1.11 (t, 9-OCOCH$_2$CH$_3$), 4.51 (d, 1'-H), 3.21 (dd, 2'-H), 3.45 (t, 4'-H), 3.28 (dq, 5'-H), 1.16 (d, 6'-H$_3$), 2.58 (s, 3'-N(CH$_3$)$_2$), 4.93 (d, 1"-H), 1.67 (dd, 2"-Hax), 2.29 (d, 2"-Heq), 1.10 (s, 3"-CH$_3$), 4.72 (d, 4"-H), 4.53 (dq, 5"-H), 1.08 (d, 6"-H$_3$), 3.26 (s, 3-OCH$_3$), 2.43 (apparent q, 3-OCOCH$_2$CH$_3$), 2.44 (apparent q, 3-OCOCH$_2$CH$_3$), 1.17 (t, 3-OCOCH$_2$CH$_3$).

EXAMPLE 30

Process for producing compound (29) [a compound represented by the formula (XXII) wherein R$^1$ represents a 1-ethoxyethyl group, R$^2$ represents a 1-ethoxyethyl group and R$^4$ represents a normal butyryl group]:

In a mixed solution of 36 ml of methylene chloride and 1.3 ml of ethyl vinyl ether was dissolved 1.20 g of the compound (28) [a compound represented by the formula (XXI) wherein R$^4$ represents a normal butyryl group] [Journal of Medicinal Chemistry, 20(5), 732 (1977)]. After 488 mg of PPTS was added thereto, the mixture was allowed to react at 30° C. for 16 hours. The reaction mixture was added to 150 ml of a saturated sodium hydrogencarbonate solution by slow degrees followed by extraction with 150 ml methylene chloride. The methylene chloride layer was successively washed with 150 ml of a 5% aqueous solution of potassium hydrogensulfate, 150 ml of a saturated aqueous solution of sodium hydrogencarbonate and 150 ml of a saturated aqueous solution of sodium chloride. The methylene chloride layer was dried over anhydrous sodium sulfate and filtered. The filtrate was concentrated under reduced pressure and 1.70 g of the residue thus obtained was purified by silica gel column chromatography [120 g: hexane/ethyl acetate (1:1)→(2:3)]. Thus 740 mg of the compound (29) was obtained.

Physicochemical properties of the compound (29)
(1) Color and appearance: colorless solid.
(2) Molecular formula: $C_{49}H_{83}NO_{17}$.
(3) Mass spectrum (SIMS): m/z 958 (M+H)$^+$.
(4) Specific rotation: $[\alpha]_D^{13}$ –90° (c 1.0, CHCl$_3$).
(5) Melting at around 72° to 75° C. without showing any definite melting point.
(6) $^1$H NMR spectrum (400 MHz, CDCl$_3$) δ (ppm: 3.87 (m, 3-H), 2.88 (br d, 4-H), 3.38 (s, 4-OCH$_3$), 3.43 (s, 4-OCH$_3$), 4.15 (br d, 5-H), 3.90 (dd, 9-H), 4.01 (dd, 9-H), 6.13 (dd, 11-H), 6.17 (dd, 11-H), 6.19 (dd, 11-H), 6.03 (br dd, 12-H), 6.04 (br dd, 12-H), 5.15 (m, 15-H), 5.23 (m, 15-H), 9.76 (s, 18-H), 9.77 (s, 18-H), 9.87 (s, 18-H), 4.82 (q, 3-OC$\underline{H}$(OCH$_2$CH$_3$)CH$_3$), 4.87 (q, 3-OC$\underline{H}$(OCH$_2$CH$_3$)CH$_3$), 4.67 (d, 1"-H), 4.99 (dd, 2'-H), 2.05 (s, 2'-OCOCH$_3$), 2.39 (s, 3'-N(CH$_3$)$_2$), 2.41 (s, 3'-N(CH$_3$)$_2$), 5.06 (br d, 1"-H), 1.84 (br dd, 2"-Hax), 2.00 (d, 2"-Heq), 1.12 (s, 3"-CH$_3$), 4.62 (d, 4"-H), 4.37 (dq, 5"-H), 1.69 (tq, 4"-OCOCH$_2$C$\underline{H}_2$CH$_3$), 0.97 (t, 4"-OCOCH$_2$CH$_2$CH$_3$).

EXAMPLE 31

Process for producing compound (30) [a compound represented by the formula (XXIII) wherein R$^1$ represents a 1-ethoxyethyl group, R$^2$ represents a 1-ethoxyethyl group and R$^4$ represents a normal butyryl group]:

In a mixed solution of 17 ml of DMSO and 1.7 ml of acetic anhydride was dissolved 575 mg of the compound (29) followed by reaction at 30° C. for 24 hours. The reaction mixture was added to 500 ml of toluene by slow degrees and washed with 500 ml of water three times. The toluene layer was dried over anhydrous sodium sulfate and filtered. The filtrate was concentrated under reduced pressure and 750 mg of the residue thus obtained was purified by silica gel column chromatography [65 g: hexane/ethyl acetate (1:1)]. Thus 325 mg of the compound (30) was obtained. Simultaneously, 135 mg of the compound (29) was recovered.

Physicochemical properties of the compound (30)
(1) Color and appearance: colorless solid.
(2) Molecular formula: $C_{51}H_{87}NO_{17}S$.
(3) Mass spectrum (SIMS): m/z 1018 (M+H)$^+$.
(4) Specific rotation: $[\alpha]_D^{13}$ –100° (c 1.0, CHCl$_3$).
(5) Melting at around 59° to 61° C. without showing any definite melting point.
(6) $^1$H NMR spectrum (400 MHz, CDCl$_3$) δ (ppm: 3.86 (m, 3-H), 2.90 (br d, 4-H), 3.38 (s, 4-OCH$_3$), 3.44 (s, 4-OCH$_3$), 4.18 (br d, 5-H), 3.90 (dd, 9-H), 4.01 (dd, 9-H), 6.14 (dd, 11-H), 6.19 (dd, 11-H), 6.03 (br dd, 12-H), 6.04 (br dd, 12-H), 5.14 (m, 15-H), 5.20 (m, 15-H), 9.76 (s, 18-H), 9.78 (s, 18-H), 9.88 (s, 18-H), 4.94 (dd, 2'-H), 3.17 (t, 4'-H), 2.03 (s, 2-OCOCH$_3$), 2.42 (s, 3'-N(CH$_3$)$_2$), 4.83 (br d, 1"-H), 2.26 (br d, 2"-Heq), 1.18 (s, 3"-CH$_3$), 1.05 (br d, 6"-H), 4.51 (d, 3"-OCH$_2$SCH$_3$), 2.20 (s, 3"-OCH$_2$SCH$_3$), 1.69 (tq, 4"-OCOC$\underline{H}_2$C$\underline{H}_2$CH$_3$), 0.97 (t, 4"-OCOCH$_2$C$\underline{H}_2$CH$_3$).

EXAMPLE 32

Process for producing compound (31) [a compound represented by the formula (XXIV) wherein R$^1$ represents a 1-ethoxyethyl group, R$^2$ represents a 1-ethoxyethyl group and R$^4$ represents a normal butyryl group]:

Thirty-seven mg of the compound (30) was dissolved in 1.2 ml of methanol and the mixture was allowed to react at 30° C. for 16 hours. The reaction mixture was concentrated under reduced pressure and 36 mg of the residue thus obtained was purified by preparative TLC [developing system: hexane/ethyl acetate (1:1)]. Thus 27 mg of the compound (31) was obtained.

Physicochemical properties of the compound (31)
(1) Color and appearance: colorless solid.
(2) Molecular formula: $C_{49}H_{85}NO_{16}S$.
(3) Mass spectrum (ELMS): m/z 975 (M)$^+$.
(4) Specific rotation: $[\alpha]_D^{17}$ –118° (c 1.0, CH$_3$OH).
(5) Melting at around 63° to 66° C. without showing any definite melting point.
(6) $^1$H NMR spectrum (400 MHz, CDCl$_3$) δ (ppm: 2.82 (dd, 2-H), 3.48 (s, 4-OCH$_3$), 3.54 (s, 4-OCH$_3$) 1.86 (m, 8-H), 3.95 (dd, 9-H), 4.05 (dd, 9-H), 6.18 (dd, 11-H), 6.19 (dd, 11-H), 5.16 (m, 15-H), 5.24 (m, 15-H), 9.76 (s, 18-H), 9.77 (s, 18-H), 9.88 (s, 18-H), 0.99 (d, 19-H$_3$), 4.80 (q, 3-OC$\underline{H}$(OCH$_2$CH$_3$)CH$_3$), 2.54 (s, 3'-N(CH$_3$)$_2$), 1.71 (dd, 2"-Hax), 1.19 (s, 3"-CH$_3$), 4.65 (d, 4"-H), 1.07 (d, 6"-H), 4.52 (d, 3"-OCH$_2$SCH$_3$), 4.65 (d, 3"-OCH$_2$SCH$_3$), 2.18 (s, 3"-OC$\underline{H}_2$SCH$_3$), 2.21 (s, 3"-OC$\underline{H}_2$SCH$_3$), 2.37 (m, 4"-OCOCH$_2$C$\underline{H}_2$CH$_3$), 1.69 (tq, 4"-OC$\overline{O}$CH$_2$CH$_2$CH$_3$), 0.97 (t, 4"-$\overline{O}$COCH$_2$CH$_2$CH$_3$).

EXAMPLE 33

Process for producing compound (33) [a compound represented by the formula (I) wherein R$^1$ represents a hydrogen atom, R$^2$ represents a hydrogen atom, R$^3$ represents a hydrogen atom and R$^4$ represents a normal butyryl group] (3"-O-methylleucomycin A$_5$):

Fifty mg of the compound (31) was dissolved in 1.3 ml of ethanol. The activity of 1.3 ml of Raney nickel was controlled in the same manner as in Example 7 and it was added to the above mixture together with 1.3 ml of ethanol. After the resulting mixture was stirred vigorously at room temperature for 20 minutes, insoluble matters were filtered and washed with 5.0 ml portions of ethanol containing 1% (v/v) conc. aqueous ammonia twice. The filtrate and washings were combined and concentrated under reduced pressure. Then, 57 mg of the thus obtained crude compound (32) [a compound of formula (XXV) wherein R$^1$ represents a 1-ethoxyethyl group, R$^2$ represents a 1-ethoxyethyl group and R$^4$ represents a normal butyryl group] was dissolved in a mixed solution of 3.8 ml of a 5% solution of acetic acid and 1.3 ml of acetonitrile and the resulting mixture was allowed to react at room temperature for 16 hours. After the reaction mixture was concentrated under reduced pressure, the thus obtained residue was dissolved in 10 ml of chloroform and washed successsively with 10 ml portions of a saturated solution of sodium hydrogencarbonate twice and 10 ml of a saturated solution of sodium chloride. The chloroform layer was dried over anhydrous sodium sulfate and filtered. The filtrate was concentrated under reduced pressure and 33 mg of the thus obtained residue was purified by preparative TLC [developing system: toluene/acetate (1:1)] to obtain 8.0 mg of the compound (33).

Physicochemical properties of the compound (33)
(1) Color and appearance: colorless solid.
(2) Molecular formula: $C_{40}H_{67}NO_{14}$.
(3) Mass spectrum (FDMS): m/z 786 (M+H)$^+$.
(5) Specific rotation: $[\alpha]_D^{15}$ –76° (c 0.9, CH$_3$OH).
(6) Melting at around 100° to 104° C. without showing any definite melting point.

(7) $^1$H NMR spectrum (400 MHz, CDCl$_3$) δ (ppm: 2.22 (br d, 2-H), 2.70 (dd, 2-H), 3.79 (br d, 3-H), 3.10 (br d, 4-H), 3.54 (s, 4-OCH$_3$), 4.11 (br d, 5-H), 1.60 (br dt, 7-H), 1.91 (m, 8-H), 4.10 (dd, 9-H), 5.69 (dd, 10-H), 6.26 (dd, 11-H), 6.04 (br dd, 12-H), 5.61 (ddd, 13-H), 2.12 (dt, 14-H), 5.29 (ddq, 15-H), 1.31 (d, 16-H$_3$), 2.34 (br dd, 17-H), 2.87 (br dd, 17-H), 9.80 (s, 18-H), 0.99 (d, 19-H$_3$), 4.59 (d, 1'-H), 3.23 (dd, 2'-H), 3.46 (t, 4'-H), 3.28 (dq, 5'-H), 1.20 (d, 6'-H$_3$), 2.58 (s, 3'-N(CH$_3$)$_2$), 4.94 (d, 1"-H), 1.67 (dd, 2"-Hax), 2.29 (d, 2"-Heq), 1.11 (s, 3"-CH$_3$), 4.72 (d, 4"-H), 4.54 (dq, 5"-H), 1.08 (d, 6"-H$_3$), 3.26 (s, 3"-OCH$_3$), 2.39 (m, 4"-OCOC H$_2$CH$_2$CH$_3$), 1.69 (tq, 4"-OCOCH$_2$CH$_2$CH$_3$) 0.96 (t, 4"-OCOCH$_2$CH$_2$CH$_3$).

EXAMPLE 34

Process for producing compound (35) [a compound represented by the formula (XXII) wherein R$^1$ represents a 1-ethoxyethyl group, R$^2$ represents an acetyl group and R$^4$ represents a normal butyryl group]:

In a mixed solution of 63 ml of methylene chloride and 1.2 ml of ethyl vinyl ether was dissolved 2.10 g of the compound (34) [a compound represented by the formula (XXII) wherein R$^1$ represents a hydrogen atom, R$^2$ represents an acetyl group and R$^4$ represents a normal butyryl group] [Journal of Medicinal Chemistry, 20(5), 732 (1977)]. After 923 mg of pPTS was added thereto, the mixture was allowed to react at 30° for 16 hours. The reaction mixture was added to 250 ml of a saturated sodium hydrogencarbonate solution by slow degrees followed by extraction with 250 ml methylene chloride. The methylene chloride layer was successively washed with 250 ml of a 5% aqueous solution of potassium hydrogensulfate, 250 ml of a saturated aqueous solution of sodium hydrogencarbonate and 250 ml of a saturated aqueous solution of sodium chloride. The methylene chloride layer was concentrated under reduced pressure and 2.20 g of the residue thus obtained was purified by silica gel column chromatography [200 g: hexane/ethyl acetate (2:3)]. Thus 1.20 g of the compound (35) was obtained.

Physicochemical properties of the compound (35)
(1) Color and appearance: colorless solid.
(2) Molecular formula: C$_{47}$H$_{77}$NO$_{17}$.
(3) Mass spectrum (FDMS).: m/z 928 (M+H)$^+$.
(4) Specific rotation: [α]$_D^{19}$–90° (c 1.0, CHCl$_3$).
(5) Melting at around 80° to 85° C. without showing any definite melting point.
(6) $^1$H NMR spectrum (400 MHz, CDCl$_3$) δ (ppm: 3.88 (m, 3-H), 2.87 (br d, 4-H), 3.36 (s, 4-OCH$_3$), 3.43 (s, 4-OCH$_3$), 4.18 (br d, 5-H), 1.43 (br dt, 7-H), 1.92 (m, 8-H), 5.23 (dd, 9-H), 5.55 (dd, 10-H), 5.58 (dd, 10-H), 6.23 (dd, 11-H), 6.34 (dd, 11-H), 6.02 (br dd, 12-H), 5.65 (ddd, 13-H), 5.69 (ddd, 13-H), 2.13 (br dt, 14-H), 5.15 (ddq, 15-H), 1.29 (d, 16-H$_3$), 9.77 (br s, 18-H), 9.88 (s, 18-H), 0.99 (d, 19-H$_3$), 1.01 (d, 19-H$_3$), 4.83 (q, 3-OCH(OCH$_2$CH$_3$)CH$_3$), 4.89 (q, 3-OCH(OCH$_2$CH$_3$)CH$_3$), 3.50 (dq, 3-OCH(OC H$_2$CH$_3$)CH$_3$), 3.60 (dq, 3-OCH (OCH$_2$CH$_3$)CH$_3$), 1.16 (t, 3-OCH(OCH$_2$CH$_3$)CH$_3$), 1.23 (t, 3-OCH(OCH$_2$C H$_3$)CH$_3$), 1.27 (d, 3-OCH(OCH$_2$CH$_3$)CH$_3$), 1.28 (d, 3-OCH(OCH$_2$CH$_3$)CH$_3$), 4.66 (d, 1'-H), 4.99 (dd, 2'-H), 3.28 (t, 4'-H), 1.24 (d, 6'-H$_3$), 2.02, 2.04, 2.05, 2.07 (4×s, 9-OCOCH$_3$, 2'-OCOCH$_3$), 2.39 (s, 3'-N(CH$_3$)$_2$), 2.41 (s, 3'-N(CH$_3$)$_2$), 5.06 (d, 1"-H), 1.84 (dd, 2"-Hax), 2.01 (dd, 2"-Heq), 1.12 (s, 3"-CH$_3$), 4.62 (d, 4"-H), 1.13 (d, 6"-H$_3$), 1.69 (tq, 4"-OCOCH$_2$CH$_2$CH$_3$), 0.97 (t, 4"-OCOCH$_2$CH$_2$C H$_3$).

EXAMPLE 35

Process for producing compound (36H) [a compound represented by the formula (XXIII) wherein R$^1$ represents a 1-ethoxyethyl group, R$^2$ represents an acetyl group and R$^4$ represents a normal butyryl group, which is an isomer giving a higher Rf value as a result of TLC using the following developing system] and compound (36L) [a compound represented by the formula (XXIII) wherein R$^1$ represents a 1-ethoxyethyl group, R$^2$ is an acetyl group and R$^4$ is a normal butyryl group, which is an isomer giving a lower Rf value as a result of TLC using the following developing system]:

After 200 mg of the compound (35) was dissolved in a mixed solution of 6.0 ml of DMSO and 0.60 ml of acetic anhydride, the resulting mixture was allowed to react at 30° C. for 40 hours. The reaction mixture was added to 50 ml of toluene by slow degrees and washed with 50 ml portions of water three times. The toluene layer was dried over anhydrous sodium sulfate and filtered. The filtrate was concentrated under reduced pressure and 215 mg of the residue thus obtained was purified by preparative TLC [developing system: hexane/ethyl acetate (1:1)]. Thus 32 mg of the compound (36H) and 29 mg of the compound (36L).

Physicochemical properties of the compound (36H)
(1) Color and appearance: colorless solid.
(2) Molecular formula: C$_{49}$H$_{81}$NO$_{17}$S.
(3) Mass spectrum (SIMS): m/z 988 (M+H)$^+$.
(4) Rf value on TLC: 0.58 [hexane/ethyl acetate (1:1)].
(5) Specific rotation: [α]$_D^{15}$–102° (c 1.0, CHCl$_3$).
(6) Melting at around 68° to 73° C. without showing any definite melting point.
(7) $^1$H NMR spectrum (400 MHz, CDCl$_3$) δ (ppm: 3.87 (m, 3-H), 2.88 (br d, 4-H), 3.44 (s, 4-OCH$_3$), 4.20 (br d, 5-H), 1.44 (br dt, 7-H), 1.90 (m, 8-H), 5.23 (dd, 9-H), 5.58 (dd, 10-H), 6.34 (dd, 11-H), 6.02 (br dd, 12-H), 5.65 (ddd, 13-H), 2.13 (dt, 14-H), 5.15 (ddq, 15-H), 1.29 (d, 16-H$_3$), 9.88 (br s, 18-H), 1.00 (d, 19-H$_3$), 4.84 (q, 3-OC H(OCH$_2$CH$_3$)CH$_3$), 3.50 (dq, 3-OCH(OCH$_2$CH$_3$)CH$_3$), 3.60 (dq, 3-OCH(OCH$_2$CH$_3$)CH$_3$), 1.23 (t, 3-OCH(OCH$_2$C H$_3$)CH$_3$), 1.28 (d, 3-OCH(OCH$_2$CH$_3$)CH$_3$), 4.65 (d, 1'-H), 4.93 (dd, 2'-H), 2.71 (t, 3'-H), 3.16 (t, 4'-H), 3.29 (dq, 5'-H), 1.19 (d, 6'-H$_3$), 2.02, 2.03 (2×s, 9-OCOCH$_3$, 2'-OCOCH$_3$), 2.41 (s, 3'-N(CH$_3$)$_2$), 4.81 (d, 1"-H), 1.68 (dd, 2"-Hax), 2.25 (d, 2"-Heq), 1.17 (s, 3"-CH$_3$), 4.55 (dq, 5"-H), 1.04 (d, 6"-H$_3$), 4.51 (d, 3"-OCH$_2$SCH$_3$), 4.63, 4.64 (2×d, 4"-H, 3"-OCH$_2$SCH$_3$), 2.19 (s, 3"-OCH$_2$SCH$_3$), 2.37 (m, 4"-OCOCH$_2$CH$_2$CH$_3$), 1.69 (tq, 4"-OCOCH$_2$CH$_2$CH$_3$), 0.97 (t, 4"-OCOCH$_2$CH$_2$CH$_3$).

Physicochemical properties of the compound (36L)
(1) Color and appearance: colorless solid.
(2) Molecular formula: C$_{49}$H$_{81}$NO$_{17}$S.
(3) Mass spectrum (SIMS): m/z 988 (M+H)$^+$.
(4) Rf value on TLC: 0.50 [hexane/ethyl acetate (1:1)].
(5) Specific rotation: [α]$_D^{14}$–92° (c 1,0, CHCl$_3$).
(6) Melting at around 70° to 74° C. without showing any definite melting point.
(7) $^1$H NMR spectrum (400 MHz, CDCl$_3$) δ (ppm: 1.84 (m, 8-H), 5.56 (dd, 10-H), 6.24 (dd, 11-H), 6.01 (br dd, 12-H), 5.69 (ddd, 13-H), 2.13 (dt, 14-H), 1.28 (d, 16-H$_3$), 2.89 (br dd, 17-H), 9.76 (s, 18-H), 0.99 (d, 19-H$_3$), 4.90 (q, 3-OCH(OCH$_2$CH$_3$)CH$_3$), 3.48 (dq, 3-OCH(OC H$_2$CH$_3$)CH$_3$), 3.62 (dq, 3-OCH (OCH$_2$CH$_3$)C$_3$), 1.15 (t, 3-OCH(OCH$_2$CH$_3$)CH$_3$), 1.27 (d, 3-OCH (OCH$_2$CH$_3$)CH$_3$), 4.54 (d, 1'-H), 4.95 (dd, 2'-H), 2.74 (t, 3'-H), 3.17 (t, 4'-H), 1.19 (d, 6'-H$_3$), 2.03, 2.05 (2×s, 9-OCOCH$_3$, 2'-OCOCH$_3$), 2.41 (s, 3'-N(CH$_3$)$_2$), 4.82 (d, 1"-H), 1.68 (dd, 2"-Hax), 2.24 (dd, 2"-Heq), 1.17 (s, 3"-CH$_3$), 4.56 (dq, 5"-H), 1.04 (d, 6"-H$_3$), 4.51 (d, 3"-OC H$_2$SCH$_3$), 4.63, 4.64 (2×d, 4"-H, 3"-OCH$_2$SCH$_3$), 2.20 (s, 3"-OCH$_2$SCH$_3$), 2.37 (m, 4"-OCOCH$_2$CH$_2$CH$_3$), 1.69 (tq, 4"-OCOCH$_2$CH$_2$CH$_3$). 0.97 (t, 4"-OCOCH$_2$CH$_2$CH$_3$).

EXAMPLE 36

Process for producing compound (37H) [a compound represented by the formula (XXIV) wherein $R^1$ represents a 1-ethoxyethyl group, $R^2$ represents an acetyl group and $R^4$ represents a normal butyryl group, which is an isomer derived from the compound (36H)]:

Nineteen mg of the compound (36H) was dissolved in 1.9 ml of methanol and the resulting mixture was allowed to react at 30° C. for 16 hours. The reaction mixture was concentrated under reduced pressure and 18 mg of the thus obtained residue was purified by preparative TLC [developing system: hexane/ethyl acetate (1:2)]. Thus 14 mg of the compound (37H) was obtained.

Physicochemical properties of the compound (37H)
(1) Color and appearance: colorless solid.
(2) Molecular formula: $C_{47}H_{79}NO_{16}S$.
(3) Mass spectrum (SIMS): m/z 946 (M+H)$^+$.
(4) Rf value on TLC: 0.33 [chloroform/methanol (30:1)].
(5) Specific rotation: $[\alpha]_D^{16}$ –90° (c 1.0, $CH_3OH$).
(6) Melting at around 72° to 75° C. without showing any definite melting point.
(7) $^1$H NMR spectrum (400 MHz, $CDCl_3$) δ (ppm: 2.69 (dd, 2-H), 3.93 (m, 3-H), 2.95 (br d, 4-H), 3.55 (s, 4-OCH$_3$), 4.07 (br d, 5-H), 1.48 (br dt, 7-H), 1.93 (m, 8-H), 5.26 (dd, 9-H), 5.59 (dd, 10-H), 6.33 (dd, 11-H), 6.03 (br dd, 12-H), 5.66 (ddd, 13-H), 2.15 (dt, 14-H), 5.16 (ddq, 15-H), 1.28 (d, 16-H$_3$), 2.73 (br dd, 17-H), 9.89 (br s, 18-H), 1.00 (d, 19-H$_3$), 4.82 (q, 3-OC$\underline{H}$(OCH$_2$CH$_3$)CH$_3$), 3.50 (dq, 3-OCH(OC$\underline{H_2}$CH$_3$)CH$_3$), 3.60 (dq, 3-OCH(OC$\underline{H_2}$CH$_3$)CH$_3$), 1.23 (t, 3-OCH(OCH$_2$C$\underline{H_3}$)CH$_3$), 1.29 (d, 3-OCH(OCH$_2$CH$_3$)C$\underline{H_3}$), 2.03 (s, 9-OC$\overline{O}$CH$_3$), 4.56 (d, 1'-H), 3.36 (dd, 2'-H), 2.47 (t, 3'-H), 1.21 (d, 6'-H$_3$), 2.53 (s, 3'-N(CH$_3$)$_2$), 4.88 (d, 1"-H), 1.71 (dd, 2"-Hax), 2.27 (d, 2"-Heq), 1.19 (s, 3"-CH$_3$), 4.58 (dq, 5"-H), 1.06 (d, 6"-H$_3$), 4.52 (d, 3"-OC$\underline{H_2}$SCH$_3$), 4.64, 4.65 (2×d, 4"-H, 3"-OCH$_2$SCH$_3$), 2.19 (s, 3"-OCH$_2$SC$\underline{H_3}$), 2.37 (m, 4"-OCOC$\underline{H_2}$CH$_2$CH$_3$), 1.69 (tq, 4"-OCO$\overline{C}$H$_2$C$\underline{H_2}$CH$_3$), 0.97 (t, 4"-OCOCH$_2$CH$_2$C$\underline{H_3}$).

EXAMPLE 37

Process for producing compound (37L) [a compound represented by the formula (XXIV) wherein $R^1$ represents a 1-ethoxyethyl group, $R^2$ represents an acetyl group and $R^4$ represents a normal butyryl group, which is an isomer derived from the compound (36L)]:

Twenty mg of the compound (36L) was dissolved in 2.0 ml methanol followed by the reaction at 30° C. for 16 hours. The reaction mixture was concentrated under reduced pressure and 19 mg of the thus obtained residue was purified by preparative TLC [developing system: hexane/ethyl acetate (1:2)]. Thus 15 mg of the compound (37L) was obtained.

Physicochemical properties of the compound (37L)
(1) Color and appearance: colorless solid.
(2) Molecular formula: $C_{47}H_{79}NO_{16}S$.
(3) Mass spectrum (SIMS): m/z 946 (M+H)$^+$.
(4) Rf value on TLC: 0.24 [chloroform/methanol (30:1)].
(5) Specific rotation: $[\alpha]_D^{16}$ –77° (c 0.5, $CH_3OH$).
(6) Melting at around 70° to 72° C. without showing any definite melting point.
(7) $^1$H NMR spectrum (400 MHz, $CDCl_3$) δ (ppm: 2.83 (dd, 2-H), 3.47 (s, 4-OCH$_3$), 1.86 (m, 8-H), 5.29 (dd, 9-H), 5.55 (dd, 10-H), 6.21 (dd, 11-H), 6.02 (br dd, 12-H), 5.66 (ddd, 13-H), 2.13 (dt, 14-H), 5.25 (ddq, 15-H), 1.28 (d, 16-H$_3$), 2.98 (br dd, 17-H), 9.77 (s, 18-H), 0.98 (d, 19-H$_3$), 4.92 (q, 3-OC$\underline{H}$(OCH$_2$CH$_3$)CH$_3$), 3.49 (dq, 3-OCH(OC$\underline{H_2}$CH$_3$)CH$_3$), 3.59 (dq, 3-OCH (OCH$_2$CH$_3$)CH$_3$), 1.16 (t, 3-OCH(OCH$_2$C$\underline{H_3}$)CH$_3$), 1.29 (d, 3-OCH (OCH$_2$CH$_3$)C$\underline{H_3}$), 2.04 (s, 9-O$\overline{C}$OCH$_3$), 4.42 (d, 1'-H), 3.25 (t, 4'-H), 1.24 (d, 6'-H$_3$), 2.53 (s, 3'-N(CH$_3$)$_2$), 4.87 (d, 1"-H), 1.70 (dd, 2"-Hax), 2.26 (d, 2"-Heq), 1.19 (s, 3"-CH$_3$), 4.60 (dq, 5"-H), 1.06 (d, 6"-H$_3$), 4.52 (d, 3"-OC$\underline{H_2}$SCH$_3$), 4.65, 4.66 (2×d, 4"-H, 3"-OCH$_2$SCH$_3$), 2.20 (s, 3"-OCH$_2$SC$\underline{H_3}$), 2.37 (m, 4"-OCOC$\underline{H_2}$CH$_2$CH$_3$), 1.69 (tq, 4"-OCOCH$_2$C$\underline{H_2}$CH$_3$), 0.97 (t, 4"-OCOCH$_2$CH$_2$C$\underline{H_3}$).

EXAMPLE 38

Process for producing compound (38H) [a compound represented by the formula (XXV) wherein $R^1$ represents a 1-ethoxyethyl group, $R^2$ represents an acetyl group and $R^4$ represents a normal butyryl group, which is an isomer derived from the compound (37H)]:

Thirty-four mg of the compound (37H) was dissolved in 0.90 ml of ethanol. The activity of 0.90 ml of Raney nickel was controlled in the same manner as in Example 7 and it was added to the above mixture together with 0.90 ml of ethanol. After the resulting mixture was stirred vigorously at room temperature for 40 minutes, insoluble matters were filtered and washed with 4.0 ml portions of ethanol containing 1% (v/v) conc. aqueous ammonia twice. The filtrate and washings were combined and concentrated under reduced pressure. Then, 31 mg of the thus obtained residue was purified by preparative TLC [developing system: toluene/acetate (2:1)] to obtain 3.3 mg of the compound (38H).

Physicochemical properties of the compound (38H)
(1) Color and appearance: colorless solid.
(2) Molecular formula: $C_{46}H_{77}NO_{16}$.
(3) Mass spectrum (SIMS): m/z 900 (M+H)$^+$.
(4) Rf value on TLC: 0.17 [chloroform/methanol (30:1)].
(5) Specific rotation: $[\alpha]_D^{17}$ –73° (c 0.3, $CH_3OH$).
(6) Melting at around 74° to 77° C. without showing any definite melting point.
(7) $^1$H NMR spectrum (400 MHz, $CDCl_3$) δ (ppm: 2.71 (dd, 2-H), 3.92 (m, 3-H), 2.97 (br d, 4-H), 3.56 (s, 4-OCH$_3$), 4.10 (br d, 5-H), 1.50 (br dt, 7-H), 1.93 (m, 8-H), 5.26 (dd, 9-H), 5.59 (dd, 10-H), 6.33 (dd, 11-H), 6.03 (br dd, 12-H), 5.65 (ddd, 13-H), 2.15 (dt, 14-H), 5.15 (ddq, 15-H), 1.29 (d, 16-H$_3$), 2.72 (br dd, 17-H), 9.90 (br s, 18-H), 1.00 (d, 19-H$_3$), 4.83 (q, 3-OC$\underline{H}$ (OCH$_2$CH$_3$)CH$_3$), 3.50 (dq, 3-OCH(OC$\underline{H_2}$CH$_3$)CH$_3$), 3.59 (dq, 3-OCH (OC$\underline{H_2}$CH$_3$)CH$_3$), 1.23 (t, 3-OCH(OCH$_2$C$\underline{H_3}$)CH$_3$), 1.28 (d, 3-OCH (OCH$_2$CH$_3$)C$\underline{H_3}$), 2.02 (s, 9-OCOCH$_3$), 4.57 (d, 1'-H), 2.47 (t, 3'-H), 2.53 (s, 3'-N(CH$_3$)$_2$), 4.89 (d, 1"-H), 1.64 (dd, 2"-Hax), 2.27 (d, 2"-Heq), 1.09 (s, 3"-CH$_3$), 4.71 (d, 4"-H), 1.06 (d, 6"-H$_3$), 3.25 (s, 3"-OCH$_3$), 2.38 (m, 4"-OCOC$\underline{H_2}$CH$_2$CH$_3$), 1.68 (tq, 4"-OCOCH$_2$C$\underline{H_2}$CH$_3$), 0.95 (t, 4"-$\overline{O}$COCH$_2$CH$_2$C$\underline{H_3}$).

EXAMPLE 39

Process for producing compound (38L) [a compound represented by the formula (XXV) wherein $R^1$ represents a 1-ethoxyethyl group, $R^2$ represents an acetyl group and $R^4$ represents a normal butyryl group, which is an isomer derived from the compound (37L)]:

Eighteen mg of the compound (37L) was dissolved in 0.40 ml of ethanol. The activity of 0.50 ml of Raney nickel was controlled in the same manner as in Example 7 and it was added to the above mixture together with 0.50 ml of ethanol. After the resulting mixture was stirred vigorously at room temperature for 40 minutes, insoluble matters were filtered and washed with 2.0 ml portions of ethanol containing 1% (v/v) conc. aqueous ammonia twice. The filtrate and washings were combined and concentrated under reduced pressure. Then, 16 mg of the thus obtained residue was purified by preparative TLC [developing system: toluene/acetate (2:1)] to obtain 1.7 mg of the compound (38L).

Physicochemical properties of the compound (38L)

(1) Color and appearance: colorless solid.
(2) Molecular formula: $C_{46}H_{77}NO_{16}$.
(3) Mass spectrum (SIMS): m/z 900 $(M+H)^+$.
(4) Rf value on TLC: 0.10 [chloroform/methanol (30:1)].
(5) Specific rotation: $[\alpha]_D^{20}$–100° (c 0.2, $CH_3OH$).
(6) Melting at around 69° to 72° C. without showing any definite melting point.
(7) $^1$H NMR spectrum (400 MHz, $CDCl_3$) δ (ppm: 2.83 (dd, 2-H), 3.48 (s, 4-$OCH_3$), 1.85 (m, 8-H), 5.28 (dd, 9-H), 5.55 (dd, 10-H), 6.22 (dd, 11-H), 6.02 (br dd, 12-H), 5.67 (ddd, 13-H), 2.14 (dt, 14-H), 5.24 (ddq, 15-H), 2.98 (br dd, 17-H), 9.78 (br s, 18-H), 0.99 (d, 19-$H_3$), 4.92 (q, 3-OC$\underline{H}$($OCH_2CH_3$)$CH_3$), 3.49 (dq, 3-OCH($OCH_2CH_3$)$CH_3$), 3.60 (dq, 3-OCH($OCH_2CH_3$)$CH_3$), 1.16 (t, 3-$\overline{OCH}$($OCH_2C$ $\underline{H_3}$)$CH_3$), 1.28 (d, $\overline{3}$-OCH($OCH_2CH_3$)$\underline{CH_3}$), 2.04 (s, 9-OCOC$H_3$), 4.44 (d, 1'-H), 2.54 (s, 3'-N($\overline{CH}_3$)$_2$), 4.89 (d, 1"-H), 1.63 (dd, 2"-Hax), 2.27 (d, 2"-Heq), 1.09 (s, 3"-$CH_3$), 4.70 (d, 4"-H), 1.06 (d, 6"-$H_3$), 3.26 (s, 3"-$OCH_3$), 2.38 (m, 4"-OCOC$H_2CH_2CH_3$), 1.69 (tq, 4"-OCOCH$_2\underline{CH_2}$CH$_3$), 0.96 (t, 4"-$\overline{O}$COCH$_2$C$_2\underline{CH_3}$).

EXAMPLE 40

Process (1) for producing compound (39) [a compound represented by the formula (I) wherein $R^1$ represents a hydrogen atom, $R^2$ represents an acetyl group, $R^3$ represents a hydrogen atom and $R^4$ represents a normal butyryl group] (9-O-acetyl-3"-O-methylleucomycin $A_5$):

In a mixed solution of 3.0 ml of a 5% solution of acetic acid and 1.0 ml of acetonitrile was dissolved 4.0 mg of the compound (38H) and the mixture was allowed to react at room temperature for 16 hours. After the reaction mixture was concentrated under reduced pressure, the thus obtained residue was added to 10 ml of chloroform and successively washed with 10 ml of a saturated sodium hydrogencarbonate solution three times and 10 ml of a saturated aqueous solution of sodium chloride. The chloroform layer was dried over anhydrous sodium sulfate and filtered. The filtrate was concentrated under reduced pressure and 4.5 mg of the residue thus obtained was purified by preparative TLC [developing system: chloroform/methanol (10:1)]. Thus 3.0 mg of the compound (39) was obtained.

Physicochemical properties of the compound (39)

(1) Color and appearance: colorless solid.
(2) Molecular formula: $C_{42}H_{69}NO_{15}$.
(3) Mass spectrum (EIMS): m/z 828 $(M+H)^+$.
(4) Specific rotation: $[\alpha]_D^{17}$–75° (c 0.6, $CH_3OH$).
(5) Melting at around 102° to 105° C. without showing any definite melting point.
(6) $^1$H NMR spectrum (400 MHz, $CDCl_3$) δ (ppm: 2.22 (br d, 2-H), 2.71 (dd, 2-H), 3.79 (br d, 3-H), 3.09 (br d, 4-H), 3.54 (s, 4-$OCH_3$), 4.14 (br d, 5-H), 1.62 (br dt, 7-H), 1.99 (m, 8-H), 5.17 (dd, 9-H), 5.60 (dd, 10-H), 6.40 (dd, 11-H), 6.03 (br dd, 12-H), 5.65 (ddd, 13-H), 2.12 (dt, 14-H), 2.50 (br dt, 14-H), 5.29 (ddq, 15-H), 1.30 (d, 16-$H_3$), 2.46 (br dd, 17-H), 2.82 (br dd, 17-H), 9.80 (s, 18-H), 0.98 (d, 19-$H_3$), 2.00 (s, 9-OCOC$H_3$), 4.57 (d, 1'-H), 3.20 (dd, 2'-H), 2.42 (t, 3'-H), 3.45 (t, 4'-H), 3.27 (dq, 5'-H), 1.20 (d, 6'-$H_3$), 2.57 (s, 3'-N($CH_3$)$_2$), 4.93 (d, 1"-H), 1.67 (dd, 2"-Hax), 2.30 (d, 2"-Heq), 1.10 (s, 3"-$CH_3$), 4.72 (d, 4"-H), 4.54 (dq, 5"-H), 1.08 (d, 6"-$H_3$), 3.26 (s, 3"-$OCH_3$), 2.39 (m, 4"-OCOC$H_2CH_2CH_3$), 1.68 (tq, 4"-OCOCH$_2\underline{CH_2}$CH$_3$), 0.96 (t, 4"-OCOCH$_2$CH$_2\underline{CH_3}$).

EXAMPLE 41

Process (2) for producing compound (39) [a compound represented by the formula (I) wherein $R^1$ represents a hydrogen atom, $R^2$ represents an acetyl group, $R^3$ represents a hydrogen atom and $R^4$ represents a normal butyryl group] (9-O-acetyl-3"-O-methylleucomycin $A_5$):

In a mixed solution of 1.2 ml of a 5% solution of acetic acid and 0.30 ml of acetonitrile was dissolved 1.6 mg of the compound (38L) and the mixture was allowed to react at room temperature for 16 hours. After the reaction mixture was concentrated under reduced pressure, the thus obtained residue was added to 5.0 ml of chloroform and successively washed with 5.0 ml of a saturated sodium hydrogencarbonate solution three times and 5.0 ml of a saturated aqueous solution of sodium chloride. The chloroform layer was dried over anhydrous sodium sulfate and filtered. The filtrate was concentrated under reduced pressure to obtain 1.2 mg of the compound (39).

EXAMPLE 42

Process for producing compound (40) [a compound represented by the formula (I) wherein $R^1$ represents a hydrogen atom, $R^2$ represents a propionyl group, $R^3$ represents a hydrogen atom and $R^4$ represents a normal butyryl group] (9-O-propionyl-3"-O-methylleucomycin $A_5$):

Ten mg of the compound (33) was dissolved in 0.50 ml of anhydrous toluene and 4.4 µl of anhydrous pyridine and 4.8 µl of propionyl chloride were successively added thereto followed by stirring at room temperature for 20 minutes. To the reaction mixture was added 10 ml of ethyl acetate and 4.1 µl of triethylamine for extraction. The ethyl acetate layer was washed with 10 ml of water twice, dried over anhydrous sodium sulfate and filtered. The filtrate was concentrated under reduced pressure and 10 mg of the residue thus obtained was purified by preparative TLC [developing system: chloroform/methanol/conc. aqueous ammonia (10:1:0.1)]. Thus 4.0 mg of the compound (40) was obtained.

Physicochemical properties of the compound (40)

(1) Color and appearance: colorless solid.
(2) Molecular formula: $C_{43}H_{71}NO_{15}$.
(3) Mass spectrum (FDMS): m/z 841 $(M)^+$.
(4) Specific rotation: $[\alpha]_D^{19}$–73° (c 0.3, $CH_3OH$).
(5) Melting at around 99° to 103° C. without showing any definite melting point.
(6) $^1$H NMR spectrum (400 MHz, $CDCl_3$) δ (ppm: 2.22 (br d, 2-H), 2.70 (dd, 2-H), 3.79 (br d, 3-H), 3.09 (br d, 4-H), 3.54 (s, 4-$OCH_3$), 4.14 (br d, 5-H), 1.62 (br dt, 7-H), 2.00 (m, 8-H), 5.18 (dd, 9-H), 5.61 (dd, 10-H), 6.40 (dd, 11-H), 6.03 (br dd, 12-H), 5.65 (ddd, 13-H), 2.12 (dt, 14-H), 2.51 (br dt, 14-H), 5.29 (ddq, 15-H), 1.30 (d, 16-$H_3$), 2.47 (br dd, 17-H), 2.82 (br dd, 17-H), 9.80 (s, 18-H), 0.98 (d, 19-$H_3$), 2.39 (q, 9-OCOC$H_2$CH$_3$), 1.09 (t, 9-OCOCH$_2\underline{CH_3}$), 4.57 (d, 1'-H), 3.21 (dd, 2'-H), 3.45 (t, 4'-H), 3.28 (dq, 5'-$\overline{H}$), 1.20 (d, 6'-$H_3$), 2.57 (s, 3'-N($CH_3$)$_2$), 4.93 (d, 1"-H), 1.67 (dd, 2"-Hax), 2.28 (d, 2"-Heq), 1.09 (s, 3"-$CH_3$), 4.72 (d, 4"-H), 4.54 (dq, 5"-H), 1.07 (d, 6"-$H_3$), 3.26 (s, 3"-$OCH_3$), 2.39 (m, 4"-OCOC$H_2CH_2CH_3$), 1.69 (tq, 4"-OCOCH$_2\underline{CH_2}$CH$_3$), 0.96 (t, 4"-$\overline{O}$COCH$_2$CH$_2\underline{CH_3}$).

REFERENCE EXAMPLE

Process for producing compound (41) [a compound represented by the formula (XXVI) wherein $R^3$ represents an acetyl group and $R^4$ represents a propionyl group] (JP-B-53-30718):

Three hundred ml of acetonitrile was added to 10.0 g of leucomycin $A_7$ to dissolve it and 2.7 g of anhydrous acetic acid was added thereto followed by stirring at room temperature for 24 hours. To the reaction mixture was added 500 ml of a saturated aqueous solution of sodium hydrogencarbonate by slow degrees. The resulting mixture was stirred at room temperature for 30 minutes and extracted with 500 ml of methylene chloride twice. The organic layer was washed with 500 ml of a saturated sodium chloride solution twice, dried over anhydrous sodium sulfate and filtered. The filtrate was concentrated under reduced pressure to obtain 10.55 g of the crude compound (41).

EXAMPLE 43

Process for producing compound (42) [a compound represented by the formula (XXVIII) wherein $R^2$ represents a TBDMS group, $R^3$ represents an acetyl group, $R^4$ represents a propionyl group and $R^5$ represents a TBDMS group]:

One hundred ml of dry DMF was added to 10.55 g of the crude compound (41) to dissolve it and 5.97 g of TBDMSCl and 5.39 g of imidazole were added thereto followed by stirring at 45° C. for 24 hours. To the reaction mixture was added 500 ml of a saturated aqueous solution of sodium hydrogencarbonate by slow degrees. The resulting mixture was stirred at room temperature for 30 minutes and extracted with 500 ml of methylene chloride twice. The organic layer was washed with 500 ml of a saturated sodium chloride solution twice, dried over anhydrous sodium sulfate and filtered. The filtrate was concentrated under reduced pressure to obtain 13.2 g of the crude compound (42). Fifty mg of the compound was purified by preparative TLC (developing system: hexane/ethyl acetate (1:1)) to obtain 28 mg of the compound (42).

Physicochemical properties of the compound (42)
  (1) Color and appearance: colorless solid.
  (2) Molecular formula: $C_{52}H_{93}NO_{15}Si_2$.
  (3) Mass spectrum (SIMS): m/z 1028 $(M+H)^+$.
  (4) Specific rotation: $[\alpha]_D^{14}$–24° (c 1.0, $CHCl_3$).
  (5) Melting at around 103° to 107° C. without showing any definite melting point.
  (6) $^1H$ NMR spectrum (400 MHz, $CDCl_3$) δ (ppm: 2.67 (dd, 2-H), 4.13 (br dd, 3-H), 2.94 (br s, 4-H), 3.40 (s, 4-$OCH_3$), 3.30 (br d, 5-H), 2.28 (m, 6-H), 0.40 (br dd, 7-H), 1.52 (m, 8-H), 4.17 (m, 9-H), 5.95 (m, 10-H), 5.95 (m, 11-H), 6.31 (br dd, 12-H), 5.47 (ddd, 13-H), 4.64 (ddq, 15-H), 1.29 (d, 16-$H_3$), 1.46 (br d, 17-H), 1.62 (dt, 17-H), 4.53 (br d, 18-H), 0.91 (d, 19-$H_3$), 4.26 (d, 1'-H), 5.10 (dd, 2'-H), 2.74 (t, 3'-H), 3.30 (t, 4'-H), 3.30 (dq, 5'-H), 1.29 (d, 6'-$H_3$), 2.11 (s, 2'-$OCOCH_3$), 2.41 (s, 3'-$N(CH_3)_2$), 5.09 (d, 1''-H), 1.85 (dd, 2''-Hax), 2.00 (d, 2''-Heq), 1.11 (s, 3''-$CH_3$), 4.62 (d, 4''-H), 4.37 (dq, 5''-H), 1.14 (d, 6''-$H_3$), 2.43 (apparent q, 4''-$OCOCH_2CH_3$), 2.44 (apparent q, 4''-$OCOCH_2CH_3$), 1.17 (t, 4''-$OCOCH_2CH_3$).

EXAMPLE 44

Process for producing compound (43) [a compound represented by the formula (XXIX) wherein $R^2$ represents a TBDMS group, $R^3$ represents an acetyl group and $R^5$ represents a TBDMS group]:

To 6.68 g of the crude compound (42) was added 334 ml of benzene to dissolve it and 167 ml of a 50% aqueous solution of sodium hydroxide and 2.19 g of tetra-n-butyl ammonium hydrogensulfate were added thereto followed by stirring at room temperature for 1 hour. The benzene layer was isolated, successively washed with 500 ml of purified water twice and the same volume of a saturated sodium chloride solution twice, dried over anhydrous sodium sulfate and filtered. The filtrate was concentrated under reduced pressure to obtain 5.33 g of the crude compound (43). Fifty mg of the compound was purified by preparative TLC (developing system: chloroform/methanol (20:1)) to obtain 25 mg of the compound (43).

Physicochemical properties of the compound (43)
  (1) Color and appearance: colorless solid.
  (2) Molecular formula: $C_{49}H_{89}NO_{14}Si_2$.
  (3) Mass spectrum (SIMS): m/z 972 $(M+H)^+$.
  (4) Specific rotation: $[\alpha]_D^{14}$–24° (c 1.0, $CHCl_3$).
  (5) Melting at around 102° to 106° C. without showing any definite melting point.
  (6) $^1H$ NMR spectrum (400 MHz, $CDCl_3$) δ (ppm: 2.66 (dd, 2-H), 4.18 (br dd, 3-H), 2.94 (br s, 4-H), 3.40 (s, 4-$OCH_3$), 3.42 (m, 5-H), 2.28 (m, 6-H), 0.40 (br dd, 7-H), 1.52 (m, 8-H), 4.18 (m, 9-H), 5.95 (m, 10-H), 5.95 (m, 11-H), 6.31 (br dd, 12-H), 5.47 (ddd, 13-H), 4.64 (ddq, 15-H), 1.45 (br d, 17-H), 1.62 (dt, 17-H), 4.52 (br d, 18-H), 0.91 (d, 19-$H_3$), 4.26 (d, 1'-H), 5.08 (dd, 2'-H), 2.73 (t, 3'-H), 3.29 (t, 4'-H), 3.29 (dq, 5'-H), 2.11 (s, 2'-$OCOCH_3$), 2.39 (s, 3'-$N(CH_3)_2$), 5.10 (d, 1''-H), 1.77 (dd, 2''-Hax), 2.02 (d, 2''-Heq), 1.23 (s, 3''-$CH_3$), 2.94 (d, 4''-H), 3.98 (dq, 5''-H).

EXAMPLE 45

Process for producing compound (44) [a compound represented by the formula (XXX) wherein $R^2$ represents a TBDMS group, $R^3$ represents an acetyl group, $R^4$ represents a normal valeryl group and $R^5$ represents a TBDMS group]:

To 500 mg of the crude compound (43) was added 5.0 ml of dry pyridine to dissolve it and 185 mg of normal valeryl chloride was added thereto followed by stirring at room temperature for 55 minutes. To the reaction mixture was added 50 ml of a saturated aqueous solution of sodium hydrogencarbonate and extracted with 50 ml portions of chloroform twice. The chloroform layer was washed with 50 ml of a saturated sodium chloride solution twice, dried over anhydrous sodium sulfate and filtered. The filtrate was concentrated under reduced pressure and dried to obtain 670 mg of the crude compound (44). Forty mg of the compound was purified by preparative TLC (developing system: chloroform/methanol (40:1)) to obtain 15 mg of the compound (44).

Physicochemical properties of the compound (44)
  (1) Color and appearance: colorless solid.
  (2) Molecular formula: $C_{54}H_{97}NO_{15}Si_2$.
  (3) Mass spectrum (SIMS): m/z 1056 $(M+H)^+$.
  (4) Specific rotation: $[\alpha]_D^{13}$–23° (c 1.0, $CHCl_3$).
  (5) Melting at around 80° to 83° C. without showing any definite melting point.
  (6) $^1H$ NMR spectrum (400 MHz, $CDCl_3$) δ (ppm: 2.67 (dd, 2-H), 4.12 (br dd, 3-H), 2.94 (br s, 4-H), 3.40 (s, 4-$OCH_3$), 3.30 (br d, 5-H), 2.28 (m, 6-H), 0.40 (br dd, 7-H), 1.52 (m, 8-H), 4.18 (m, 9-H), 5.94 (m, 10-H), 5.94 (m, 11-H), 6.30 (br dd, 12-H), 5.47 (ddd, 13-H), 4.64 (ddq, 15-H), 1.28 (d, 16-$H_3$), 1.45 (br d, 17-H), 1.62 (dt, 17-H), 4.53 (br d, 18-H), 0.91 (d, 19-$H_3$), 4.26 (d, 1'-H), 5.10 (dd, 2'-H), 2.74 (t, 3'-H), 3.30 (t, 4'-H), 3.30 (dq, 5'-H), 1.28 (d, 6'-$H_3$), 2.10 (s, 2'-$OCOCH_3$), 2.41 (s, 3'-$N(CH_3)_2$), 5.09 (d, 1''-H), 1.85 (dd, 2''-Hax), 2.00 (d, 2''-Heq), 1.11 (s, 3''-$CH_3$), 4.62 (d, 4''-H), 4.37 (dq, 5''-H), 1.14 (d, 6''-$H_3$), 2.39 (apparent t, 4''-$OCOCH_2CH_2CH_3$), 2.40 (apparent t, 4''-$OCOCH_2CH_2CH_3$), 1.62 (m, 4''-$OCOCH_2CH_2CH_3$), 1.36 (tq, 4''-$OCOCH_2CH_2CH_3$), 0.91 (t, 4''-$OCOCH_2CH_2CH_3$).

EXAMPLE 46

Process for producing compound (45) [a compound represented by the formula (VII) wherein $R^2$ represents a TBDMS group, R³ represents an acetyl group, R⁴ represents a normal valeryl group and R⁵ represents a TBDMS group]:

To a mixed solution of 19 ml of dry DMSO and 1.9 ml of acetic anhydride was added 630 mg of the crude compound (44) and the mixture was allowed to react at 45° C. for 5 days. After 200 ml of benzene was added thereto, the resulting mixture was successively washed with 200 ml portions of purified water twice and the same volume of a saturated sodium chloride solution twice. The organic layer was dried over anhydrous sodium sulfate and filtered. The filtrate was concentrated under reduced pressure and 650 mg of the thus obtained residue was purified by silica gel column chromatography (50 g: hexane/ethyl acetate (2:1)) to obtain 105 mg of the compound (45).

Physicochemical properties of the compound (45)
(1) Color and appearance: colorless solid.
(2) Molecular formula: $C_{56}H_{101}NO_{15}SSi_2$.
(3) Mass spectrum (SIMS): m/z 1116 (M+H)⁺.
(4) Specific rotation: $[\alpha]_D^{18}$ –36° (c 1.0, CHCl₃).
(5) Melting at around 65° to 68° C. without showing any definite melting point.
(6) ¹H NMR spectrum (400 MHz, CDCl₃) δ (ppm: 2.66 (dd, 2-H), 4.12 (br dd, 3-H), 2.94 (br s, 4-H), 3.40 (s, 4-OCH₃), 3.28 (br d, 5-H), 0.40 (br dd, 7-H), 1.50 (m, 8-H), 4.17 (br dd, 9-H), 5.94 (m, 10-H), 5.94 (m, 11-H), 6.30 (br dd, 12-H), 5.45 (ddd, 13-H), 4.62 (ddq, 15-H), 1.28 (d, 16-H₃), 1.43 (br d, 17-H), 4.52 (br d, 18-H), 0.90 (d, 19-H₃), 4.24 (d, 1'-H), 5.05 (dd, 2'-H), 2.74 (t, 3'-H), 3.15 (t, 4'-H), 3.26 (dq, 5'-H), 1.23 (d, 6'-H₃), 2.09 (s, 2'-OCOCH₃), 2.41 (s, 3'-N(CH₃)₂), 4.82 (d, 1"-H), 1.68 (dd, 2"-Hax), 2.24 (d, 2"-Heq), 1.17 (s, 3"-CH₃), 4.67 (d, 4"-H), 4.58 (dq, 5"-H), 1.04 (d, 6"-H₃), 4.52 (d, 3"-OCH₂SCH₃), 4.63 (d, 3"-OCH₂SCH₃), 2.20 (s, 3"-OCH₂SCH₃), 2.37 (apparent t, 4"-OCOCH₂CH₂CH₂CH₃), 2.39 (apparent t, 4"-OCOCH₂CH₂CH₂CH₃), 1.62 (m, 4"-OCOCH₂CH₂CH₂CH₃), 1.35 (tq, 4"-OCOCH₂CH₂CH₂CH₃), 0.90 (t, 4"-OCOCH₂CH₂CH₂CH₃).

EXAMPLE 47

Process for producing compound (46) [a compound represented by the formula (XXXI) wherein R² represents a TBDMS group, R⁴ represents a normal valeryl group and R⁵ represents a TBDMS group]:

In 10 ml of methanol was dissolved 105 mg of the compound (45) and the mixture was allowed to react at 40° C. for 2 days. The resulting mixture was concentrated under reduced pressure to obtain 100 mg of the compound (46).

Physicochemical properties of the compound (46)
(1) Color and appearance: colorless solid.
(2) Molecular formula: $C_{54}H_{99}NO_{14}SSi_2$.
(3) Mass spectrum (SIMS): m/z 1074 (M+H)⁺.
(4) Specific rotation: $[\alpha]_D^{15}$ –17° (c 1.0, CH₃OH).
(5) Melting at around 63° to 66° C. without showing any definite melting point.
(6) ¹H NMR spectrum (400 MHz, CDCl₃) δ (ppm: 4.03 (br dd, 3-H), 3.24 (br s, 4-H), 3.44 (s, 4-OCH₃), 3.48 (br d, 5-H), 2.16 (m, 6-H), 0.42 (br dd, 7-H), 1.60 (m, 8-H), 4.18 (br dd, 9-H), 5.70 (br dd, 10-H), 6.09 (m, 11-H), 6.09 (m, 12-H), 5.61 (dt, 13-H), 2.28 (m, 14-H), 4.82 (ddq, 15-H), 1.30 (d, 16-H₃), 1.44 (br d, 17-H), 1.66 (dt, 17-H), 4.56 (br d, 18-H), 0.89 (d, 19-H₃), 4.27 (d, 1'-H), 3.42 (dd, 2'-H), 3.24 (t, 4'-H), 3.24 (dq, 5'-H), 1.20 (d, 6'-H₃), 2.54 (s, 3-N(CH₃)₂), 4.87 (d, 1"-H), 1.70 (dd, 2"-Hax), 2.25 (d, 2"-Heq), 1.17 (s, 3"-CH₃), 4.67 (d, 4"-H), 4.60 (dq, 5"-H), 1.06 (d, 6"-H₃), 4.51 (d, 3"-OCH₂SCH₃), 4.64 (d, 3"-OCH₂SCH₃), 2.18 (s, 3"-OCH₂SCH₃), 2.38 (apparent t, 4"-OCOCH₂CH₂CH₂CH₃), 2.39 (apparent t, 4"-OCOCH₂CH₂CH₂CH₃), 1.63 (m, 4"-OCOCH₂CH₂CH₂CH₃), 1.35 (tq, 4"-OCOCH₂CH₂CH₂CH₃), 0.91 (t, 4"-OCOCH₂CH₂CH₂CH₃).

EXAMPLE 48

Process for producing compound (47) [a compound represented by the formula (XXXII) wherein R² represents a TBDMS group, R⁴ represents an normal valeryl group and R⁵ represents a TBDMS group]:

Ninety-five mg of the compound (46) was dissolved in 2.0 ml of ethanol. The activity of 6.0 ml of Raney nickel was controlled in the same manner as in Example 7 and it was added to the above mixture together with 2.0 ml of ethanol. After the resulting mixture was stirred vigorously at room temperature for 40 minutes, insoluble matters were filtered and the filtrate was concentrated under reduced pressure. Then, 95 mg of the thus obtained residue was purified by preparative TLC [developing system: chloroform/methanol/conc. aqueous ammonia (300:10:1)] to obtain 36 mg of the compound (47).

Physicochemical properties of the compound (47)
(1) Color and appearance: colorless solid.
(2) Molecular formula: $C_{53}H_{97}NO_{14}Si_2$.
(3) Mass spectrum (SIMS): m/z 1028 (M+H)⁺.
(4) Specific rotation: $[\alpha]_D^{15}$ –16° (c 1.0, CH₃OH).
(5) Melting at around 70° to 72° C. without showing any definite melting point.
(6) ¹H NMR spectrum (400 MHz, CDCl₃) δ (ppm: 4.04 (br dd, 3-H), 3.44 (s, 4-OCH₃), 3.47 (br d, 5-H), 2.17 (m, 6-H), 0.42 (br dd, 7-H), 4.18 (br dd, 9-H), 5.71 (br dd, 10-H), 6.10 (m, 11-H), 6.10 (m, 12-H), 5.62 (dt, 13-H), 2.30 (m, 14-H), 4.82 (ddq, 15-H), 1.30 (d, 16-H₃), 1.42 (br d, 17-H), 1.67 (dt, 17-H), 4.56 (br d, 18-H), 0.92 (d, 19-H₃), 4.29 (d, 1'-H), 3.38 (dd, 2'-H), 3.31 (t, 4'-H), 1.22 (d, 6'-H₃), 2.54 (s, 3'-N(CH₃)₂), 4.90 (d, 1"-H), 2.27 (d, 2"-Heq), 1.08 (s, 3"-CH₃), 4.70 (d, 4"-H), 4.58 (dq, 5"-H), 1.06 (d, 6"-H₃), 3.25 (s, 3"-OCH₃), 2.39 (apparent t, 4"-OCOCH₂CH₂CH₂CH₃), 2.40 (apparent t, 4"-OCOCH₂CH₂CH₂CH₃), 1.63 (m, 4"-OCOCH₂CH₂CH₂CH₃), 1.35 (tq, 4"-OCOCH₂CH₂CH₂CH₃), 0.89 (t, 4"-OCOCH₂CH₂CH₂CH₃).

EXAMPLE 49

Process for producing compound (48) [a compound represented by the formula (I) wherein R¹ represents a hydrogen atom, R² represents a hydrogen atom, R³ represents a hydrogen atom and R⁴ represents an normal valeryl group] (3"-O-methyl-4"-O-n-valerylleucomycin V):

Thirty-five mg of the compound (47) was dissolved in 255 μl of a 2M TBAF/THF solution and the resulting mixture was allowed to react at 45° C. for 1 hour. After the reaction mixture was cooled to room temperature, 1.0 ml of a 5% potassium hydrogensulfate was added dropwise thereto and extraction was carried out with 10 ml portions of chloroform twice. The chloroform layer was combined and successively washed with 20 ml portions of a saturated sodium hydrogencarbonate solution twice and 20 ml portions of a saturated sodium chloride solution twice. The mixture was dried over anhydrous sodium sulfate and filtered. The filtrate was concentrated under reduced pressure and the residue thus obtained was purified by preparative TLC [developing system: chloroform/methanol/conc. aqueous ammonia (400:20:1)]. Thus 7.0 mg of the compound (48) was obtained.

Physicochemical properties of the compound (48)

(1) Color and appearance: colorless solid.
(2) Molecular formula: $C_{41}H_{69}NO_{14}$.
(3) Mass spectrum (EIMS): m/z 799 (M)$^+$.
(4) Specific rotation: $[\alpha]_D{}^{17}$ –68° (c 0.5, $CH_3OH$).
(5) Melting at around 98° to 102° C. without showing any definite melting point.
(6) $^1H$ NMR spectrum (400 MHz, $CDCl_3$) δ (ppm: 2.21 (d, 2-H), 2.69 (dd, 2-H), 3.78 (br d, 3-H), 3.08 (br d, 4-H). 3.53 (s, 4-$OCH_3$), 4.10 (br d, 5-H), 1.58 (br dt, 7-H), 1.90 (m, 8-H), 4.09 (dd, 9-H), 5.67 (dd, 10-H), 6.25 (dd, 11-H), 6.02 (br dd, 12-H), 5.60 (ddd, 13-H), 2.10 (dt, 14-H), 2.49 (br dt, 14-H), 5.28 (ddq, 15-H), 1.29 (d, 16-$H_3$), 2.33 (br dd, 17-H), 2.86 (br dd, 17-H), 9.79 (br s, 18-H), 0.98 (d, 19-$H_3$), 4.57 (d, 1'-H), 3.21 (dd, 2'-H), 3.43 (t, 4'-H), 3.27 (dq, 5'-H), 1.18 (d, 6'-$H_3$), 2.55 (s, 3'-$N(CH_3)_2$), 4.92 (d, 1"-H), 1.65 (dd, 2"-Hax), 2.28 (d, 2"-Heq), 1.09 (s, 3"-$CH_3$), 4.70 (d, 4"-H), 4.52 (dq, 5"-H), 1.06 (d, 6"-$H_3$), 3.24 (s, 3"-$OCH_3$), 2.39 (apparent t, 4"-$OCOCH_2CH_2CH_2CH_3$), 2.40 (apparent t, 4"-$OCOCH_2CH_2CH_2C\underline{H}_3$), 1.62 (m, 4"-$OCOCH_2C\underline{H}_2CH_2CH_3$), 1.34 (tq, 4"-$OCOCH_2CH_2C\underline{H}_2CH_3$), 0.90 (t, 4"-$OCOCH_2CH_2CH_2C\underline{H}_3$).

EXAMPLE 50

Process for producing compound (49) [a compound represented by the formula (XXX) wherein $R^2$ represents a TBDMS group, $R^3$ represents an acetyl group, $R^4$ represents an isobutyryl group and $R^5$ represents a TBDMS group]:

To 500 mg of the compound (43) was added 5.0 ml of dry pyridine to dissolve it and 164 mg of isobutyryl chloride was added thereto followed by stirring at room temperature for 15 minutes. Fifty ml of a saturated sodium hydrogencarbonate solution was added thereto and extraction was carried out with 50 ml portions of chloroform twice. The chloroform layer was washed with 50 ml portions of a saturated sodium chloride solution twice, dried over anhydrous sodium sulfate and filtered. The filtrate was concentrated under reduced pressure and dried to obtain 544 mg of the crude compound (49). Forty mg of the residue thus obtained was purified by preparative TLC [developing system: chloroform/methanol/ (40:1)]. Thus 21 mg of the compound (49) was obtained.

Physicochemical properties of the compound (49)
(1) Color and appearance: colorless solid.
(2) Molecular formula: $C_{53}H_{95}NO_{15}Si_2$.
(3) Mass spectrum (SIMS): m/z 1042 (M+H)$^+$.
(4) Specific rotation: $[\alpha]_D{}^{13}$ –20° (c 1.0, $CHCl_3$).
(5) Melting at around 103° to 106° C. without showing any definite melting point.
(6) $^1H$ NMR spectrum (400 MHz, $CDCl_3$) δ (ppm: 2.67 (dd, 2-H), 4.12 (br dd, 3-H), 2.94 (br s, 4-H), 3.40 (s, 4-$OCH_3$), 3.30 (br d, 5-H), 2.28 (m, 6-H), 0.40 (br dd, 7-H), 1.52 (m, 8-H), 4.18 (m, 9-H), 5.95 (m, 10-H), 5.95 (m, 11-H), 6.31 (br dd, 12-H), 5.47 (ddd, 13-H), 4.64 (ddq, 15-H), 1.29 (d, 16-$H_3$), 1.45 (br d, 17-H), 1.62 (dt, 17-H), 4.52 (br d, 18-H), 0.91 (d, 19-$H_3$), 4.26 (d, 1'-H), 5.10 (dd, 2'-H), 2.74 (t, 3'-H), 3.30 (t, 4'-H), 3.30 (dq, 5'-H), 1.29 (d, 6'-$H_3$), 2.10 (s, 2'-$OCOCH_3$), 2.41 (s, 3'-$N(CH_3)_2$), 5.09 (d, 1"-H), 1.84 (dd, 2"-Hax), 1.99 (d, 2"-Heq), 1.10 (s, 3"-$CH_3$), 4.60 (d, 4"-H), 4.38 (dq, 5"-H), 1.13 (d, 6"-$H_3$), 2.68 (septet, 4"-$OCOC\underline{H}(CH_3)_2$), 1.19 (d, 4"-$OCOCH(C\underline{H}_3)_2$), 1.20 (d, 4"-$OCOCH(C\underline{H}_3)_2$).

EXAMPLE 51

Process for producing compound (50) [a compound represented by the formula (VII) wherein $R^2$ represents a TBDMS group, $R^3$ represents an acetyl group, $R^4$ represents an isobutyryl group and $R^5$ represents a TBDMS group]:

To a mixed solution of 15.0 ml of dry DMSO and 1.5 ml of acetic anhydride was added 505 mg of the crude compound (49) and the mixture was allowed to react at 45° C. for 5 days. After 200 ml of benzene was added thereto, the resulting mixture was successively washed with 200 ml portions of purified water twice and the same volume of a saturated sodium chloride solution twice. The organic layer was dried over anhydrous sodium sulfate and filtered. The filtrate was concentrated under reduced pressure and 500 mg of the thus obtained residue was purified by silica gel column chromatography (50 g: hexane/ethyl acetate (2:1)) to obtain 54 mg of the compound (50).

Physicochemical properties of the compound (50)
(1) Color and appearance: colorless solid.
(2) Molecular formula: $C_{55}H_{99}NO_{15}SSi_2$.
(3) Mass spectrum (SIMS): m/z 1102 (M+H)$^+$.
(4) Specific rotation: $[\alpha]_D{}^{16}$ –42° (c 1.0, $CHCl_3$).
(5) Melting at around 71° to 73° C. without showing any definite melting point.
(6) $^1H$ NMR spectrum (400 MHz, $CDCl_3$) δ (ppm: 2.67 (dd, 2-H), 4.13 (br dd, 3-H), 2.95 (br s, 4-H), 3.41 (s, 4-$OCH_3$), 3.28 (br d, 5-H), 0.40 (br dd, 7-H), 1.51 (m, 8-H), 4.17 (br dd, 9-H), 5.94 (m, 10-H), 5.94 (m, 11-H), 6.30 (br dd, 12-H), 5.46 (ddd, 13-H), 4.63 (ddq, 15-H), 1.28 (d, 16-$H_3$), 1.44 (br d, 17-H), 4.52 (br d, 18-H), 4.25 (d, 1'-H), 5.05 (dd, 2'-H), 2.75 (t, 3'-H), 3.16 (t, 4'-H), 3.26 (dq, 5'-H), 1.24 (d, 6'-$H_3$), 2.10 (s, 2'-$OCOCH_3$), 2.41 (s, 3'-$N(CH_3)_2$), 4.83 (d, 1"-H), 1.69 (dd, 2"-Hax), 2.23 (d, 2"-Heq), 1.18 (s, 3"-$CH_3$), 4.67 (d, 4"-H), 4.59 (dq, 5"-H), 1.04 (d, 6"-$H_3$), 4.51 (d, 3"-$OCH_2SCH_3$), 4.62 (d, 3"-$OCH_2SCH_3$), 2.21 (s, 3"-$OCH_2SC\underline{H}_3$), 2.65 (septet, 4"-$OCOC\underline{H}(CH_3)_2$).

EXAMPLE 52

Process for producing compound (51) [a compound represented by the formula (XXXI) wherein $R^2$ represents a TBDMS group, $R^4$ represents an isobutyryl group and $R^5$ represents a TBDMS group]:

In 6.0 ml of methanol was dissolved 54 mg of the compound (50) and the mixture was allowed to react at 40° C. for 2 days. The resulting mixture was concentrated under reduced pressure to obtain 50 mg of the compound (51).

Physicochemical properties of the compound (51)
(1) Color and appearance: colorless solid.
(2) Molecular formula: $C_{53}H_{97}NO_{14}SSi_2$.
(3) Mass spectrum (SIMS): m/z 1060 (M+H)$^+$.
(4) Specific rotation: $[\alpha]_D{}^{15}$ –30° (c 1.0, $CH_3OH$).
(5) Melting at around 70° to 72° C. without showing any definite melting point.
(6) $^1H$ NMR spectrum (400 MHz, $CDCl_3$) δ (ppm: 4.04 (br dd, 3-H), 3.25 (br s, 4-H), 3.44 (s, 4-$OCH_3$), 3.48 (br d, 5-H), 2.16 (m, 6-H), 0.42 (br dd, 7-H), 1.60 (m, 8-H), 4.19 (br dd, 9-H), 5.71 (br dd, 10-H), 6.10 (m, 11-H), 6.10 (m, 12-H), 5.62 (dt, 13-H), 2.29 (m, 14-H), 4.82 (ddq, 15-H), 1.30 (d, 16-$H_3$), 1.43 (br d, 17-H), 1.67 (dt, 17-H), 4.57 (br d, 18-H), 0.92 (d, 19-$H_3$), 4.28 (d, 1'-H), 3.42 (dd, 2'-H), 3.25 (t, 4'-H), 3.25 (dq, 5'-H), 2.55 (s, 3'-$N(CH_3)_2$), 4.89 (d, 1"-H), 1.71 (dd, 2"-Hax), 2.24 (d, 2"-Heq), 1.17 (s, 3"-$CH_3$), 4.65 (d, 4"-H), 4.61 (dq, 5"-H), 1.06 (d, 6"-$H_3$), 4.50 (d, 3"-$OCH_2SCH_3$), 4.63 (d, 3"-$OCH_2SCH_3$), 2.18 (s, 3"-$OCH_2SC\underline{H}_3$), 2.64 (m, 4"-$OCOC\underline{H}(CH_3)_2$), 1.19 (d, 4"-$OCOCH(C\underline{H}_3)_2$).

EXAMPLE 53

Process for producing compound (52) [a compound represented by the formula (XXXII) wherein $R^2$ represents a TBDMS group, R⁴ represents an isobutyryl group and R⁵ represents a TBDMS group]:

After 115 mg of the compound (51) was dissolved in 2.4 ml of ethanol, the activity of 7.3 ml of Raney nickel was controlled in the same manner as in Example 7 and it was added to the above mixture together with 2.4 ml of ethanol. After the resulting mixture was stirred vigorously at room temperature for 35 minutes, insoluble matters were filtered and the filtrate was concentrated under reduced pressure. Then, 110 mg of the thus obtained residue was purified by preparative TLC [developing system: chloroform/methanol/conc. aqueous ammonia (300:10:1)] to obtain 45 mg of the compound (52).

Physicochemical properties of the compound (52)
  (1) Color and appearance: colorless solid.
  (2) Molecular formula: $C_{52}H_{95}NO_{14}Si_2$.
  (3) Mass spectrum (SIMS): m/z 1014 (M+H)⁺.
  (4) Specific rotation: $[\alpha]_D^{15}$ −20° (c 1.0, $CH_3OH$).
  (5) Melting at around 82° to 85° C. without showing any definite melting point.
  (6) ¹H NMR spectrum (400 MHz, $CDCl_3$) δ (ppm: 4.04 (br dd, 3-H), 3.44 (s, 4-OCH₃), 3.48 (br d 5-H), 2.17 (m, 6-H), 0.42 (br dd, 7-H), 1.61 (m, 8-H), 4.19 (br dd, 9-H), 5.71 (br dd, 10-H), 6.10 (m, 11-H), 6.10 (m, 12-H), 5.62 (dt, 13-H), 2.30 (m, 14-H), 4.82 (ddq, 15-H), 1.31 (d, 16-H₃), 1.43 (br d, 17-H), 1.68 (dt, 17-H), 4.57 (br d, 18-H), 0.94 (d, 19-H₃), 4.30 (d, 1'-H), 3.38 (dd, 2'-H), 3.32 (t, 4'-H), 1.22 (d, 6'-H₃), 2.55 (s, 3'-N(CH₃)₂), 4.90 (d, 1"-H), 1.65 (dd, 2"-Hax), 1.08 (S, 3"-CH₃), 4.69 (d, 4"-H), 4.59 (dq, 5"-H), 1.07 (d, 6"-H₃), 3.25 (s, 3"-OCH₃), 2.67 (septet, 4"-OCOCH(CH₃)₂), 1.19 (d, 4"-OCOCH(CH₃)₂), 1.20 (d, 4"-OCOCH(CH₃)₂).

EXAMPLE 54

Process for producing compound (53) [a compound represented by the formula (I) wherein R¹ represents a hydrogen atom, R² represents a hydrogen atom, R³ represents a hydrogen atom and R⁴ represents an isobutyryl group] (4"-O-isobutyryl-3"-Omethylleucomycin V):

Forty-five mg of the compound (52) was dissolved in 333 μl of a 2M TBAF/THF solution and the resulting mixture was allowed to react at 45° C. for 50 minutes. After the reaction mixture was cooled to room temperature, 1.0 ml of a 5% potassium hydrogensulfate was added dropwise thereto and extraction was carried out with 10 ml portions of chloroform twice. The chloroform layer was combined and successively washed with 20 ml portions of a saturated sodium hydrogen-carbonate solution twice and 20 ml portions of a saturated sodium chloride solution twice. The mixture was dried over anhydrous sodium sulfate and filtered. The filtrate was concentrated under reduced pressure and the residue thus obtained was purified by preparative TLC [developing system: chloroform/methanol/conc. aqueous ammonia (400:20:1)]. Thus 9.0 mg of the compound (53) was obtained.

Physicochemical properties of the compound (53)
  (1) Color and appearance: colorless solid.
  (2) Molecular formula: $C_{40}H_{67}NO_{14}$.
  (3) Mass spectrum (EIMS): m/z 785 (M)⁺.
  (4) Specific rotation: $[\alpha]_D^{17}$ −71° (c 0.5, $CH_3OH$).
  (5) Melting at around 98° to 102° C. without showing any definite melting point.
  (6) ¹H NMR spectrum (400 MHz, $CDCl_3$) δ (ppm: 2.20 (d, 2-H), 2.69 (dd, 2-H), 3.77 (br dd, 3-H), 3.08 (br d, 4-H), 3.53 (s, 4-OCH₃), 4.09 (br d, 5-H), 0.93 (br ddd, 7-H), 1.58 (br dt, 7-H), 1.89 (m, 8-H), 4.08 (dd, 9-H), 5.67 (dd, 10-H), 6.25 (dd, 11-H), 6.02 (br dd, 12-H), 5.59 (ddd, 13-H), 2.10 (dt, 14-H), 2.49 (br dt, 14-H), 5.28 (ddq, 15-H), 1.29 (d, 16-H₃), 2.32 (br dd, 17-H), 2.86 (br dd, 17-H), 9.79 (br s, 18-H), 0.97 (d, 19-H₃), 4.57 (d, 1'-H), 3.22 (dd, 2'-H), 2.47 (t, 3'-H), 3.44 (t, 4'-H), 3.27 (dq, 5'-H), 2.57 (s, 3'-N(CH₃)₂), 4.92 (d, 1"-H), 1.66 (dd, 2"-Hax), 2.26 (d, 2"-Heq), 1.08 (s, 3"-CH₃), 4.69 (d, 4"-H), 4.52 (dq, 5"-H), 1.05 (d, 6"-H₃), 3.24 (s, 3"-OCH₃), 2.67 (septet, 4"-OCOCH(CH₃)₂), 1.18 (d, 4"-OCOCH(CH₃)₂), 1.19 (d, 4"-OCOCH(CH₃)₂).

EXAMPLE 55

Process for producing compound (54) [a compound represented by the formula (XXX) wherein R² represents a TBDMS group, R³ represents an acetyl group, R⁴ represents an isovaleryl group and R⁵ represents a TBDMS group]:

To 500 mg of the compound (43) was added 5.0 ml of dry pyridine to dissolve it and 185 mg of isovaleryl chloride was added thereto followed by stirring at room temperature for 25 minutes. Fifty ml of a saturated sodium hydrogencarbonate solution was added thereto and extraction was carried out with 50 ml portions of chloroform twice. The chloroform layer was washed with 50 ml portions of a saturated sodium chloride solution twice, dried over anhydrous sodium sulfate and filtered. The filtrate was concentrated under reduced pressure and dried to obtain 650 mg of the crude compound (54). Thirty mg of the residue thus obtained was purified by preparative TLC [developing system: chloroform/methanol (40:1)]. Thus 17 mg of the compound (54) was obtained.

Physicochemical properties of the compound (54)
  (1) Color and appearance: colorless solid.
  (2) Molecular formula: $C_{54}H_{97}NO_{15}Si_2$.
  (3) Mass spectrum (SIMS): m/z 1056 (M+H)⁺.
  (4) Specific rotation: $[\alpha]_D^{14}$ −19° (c 1.0, $CHCl_3$).
  (5) Melting at around 101° to 105° C. without showing any definite melting point.
  (6) ¹H NMR spectrum (400 MHz, $CDCl_3$) δ (ppm: 2.65 (dd, 2-H), 4.12 (br dd, 3-H), 2.94 (br s, 4-H), 3.39 (s, 4-OCH₃), 3.29 (br d, 5-H), 0.40 (br dd, 7-H), 1.51 (m, 8-H), 4.17 (m, 9-H), 5.94 (m, 10-H), 5.94 (m, 11-H), 6.30 (br dd, 12-H), 5.46 (ddd, 13-H), 4.63 (ddq, 15-H), 1.28 (d, 16-H₃), 1.44 (br d, 17-H), 1.61 (dt, 17-H), 4.52 (br d, 18-H), 0.90 (d, 19-H₃), 4.26 (d, 1'-H), 5.09 (dd, 2'-H), 2.73 (t, 3'-H), 3.29 (t, 4'-H), 3.29 (dq, 5'-H), 1.28 (d, 6'-H₃), 2.10 (s, 2'-OCOCH₃), 2.40 (s, 3'-N(CH₃)₂), 5.08 (d, 1"-H), 1.84 (dd, 2"-Hax), 1.98 (d, 2"-Heq), 1.10 (s, 3"-CH₃), 4.61 (d, 4"-H), 4.37 (dq, 5"-H), 1.14 (d, 6"-H₃), 2.28 (dd, 4"-OCOCH₂CH(CH₃)₂), 2.13 (m, 4"-OCOCH₂CH(CH₃)₂), 0.96 (d, 4"-OCOCH₂CH(CH₃)₂).

EXAMPLE 56

Process for producing compound (55) [a compound represented by the formula (VII) wherein R² represents a TBDMS group, R³ represents an acetyl group, R⁴ represents an isovaleryl group and R⁵ represents a TBDMS group]:

After 650 mg of the crude compound (54) was dissolved in a mixed solution of 20 ml of dry DMSO and 2.0 ml of acetic anhydride, the mixture was allowed to react at 45° C. for 5 days. Two hundred ml of benzene was added thereto, the resulting mixture was successively washed with 200 ml portions of purified water twice and the same volume of a saturated sodium chloride solution twice. The organic layer was dried over anhydrous sodium sulfate and filtered. The filtrate was concentrated under reduced pressure and 655 mg of the thus obtained residue was purified by silica gel column chromatography (50 g: hexane/ethyl acetate (2:1)) to obtain 170 mg of the compound (55).

Physicochemical properties of the compound (55)
(1) Color and appearance: colorless solid.
(2) Molecular formula: $C_{56}H_{101}NO_{15}SSi_2$.
(3) Mass spectrum (SIMS): m/z 1116 (M+H)$^+$.
(4) Specific rotation: $[\alpha]_D^{13}$ –39° (c 1.0, CHCl$_3$).
(5) Melting at around 80° to 82° C. without showing any definite melting point.
(6) $^1$H NMR spectrum (400 MHz, CDCl$_3$) δ (ppm: 2.67 (dd, 2-H), 4.13 (br dd, 3-H), 2.95 (br s, 4-H), 3.42 (s, 4-OCH$_3$), 3.29 (br d, 5-H), 0.41 (br dd, 7-H), 1.51 (m, 8-H), 4.18 (br dd, 9-H), 5.95 (m, 10-H), 5.95 (m, 11-H), 6.31 (br dd, 12-H), 5.46 (ddd, 13-H), 4.64 (ddq, 15-H), 1.29 (d, 16-H$_3$), 1.45 (br d, 17-H), 1.62 (dt, 17-H), 4.52 (br d, 18-H), 0.91 (d, 19-H$_3$), 4.25 (d, 1'-H), 5.05 (dd, 2'-H), 2.75 (t, 3'-H), 3.15 (t, 4'-H), 3.27 (dq, 5'-H), 1.24 (d, 6'-H$_3$), 2.10 (s, 2'-OCOCH$_3$), 2.42 (s, 3'-N(CH$_3$)$_2$), 4.83 (d, 1"-H), 1.69 (dd, 2"-Hax), 1.18 (s, 3"-CH$_3$), 4.68 (d, 4"-H), 4.59 (dq, 5"-H), 1.06 (d, 6"-H$_3$), 4.52 (d, 3"-OC$\underline{H}_2$SCH$_3$), 4.64 (s, 3"-OCH$_2$SCH$_3$), 2.20 (s, 3"-OCH$_2$SC$\underline{H}_3$), 2.27 (dd, 4"-OCOC$\underline{H}_2$CH(CH$_3$)$_2$), 2.14 (m, 4"-OCOCH$_2$C$\underline{H}$(CH$_3$)$_2$), 0.97 (d, 4"-OCOCH$_2$CH(C$\underline{H}_3$)$_2$).

EXAMPLE 57

Process for producing compound (56) [a compound represented by the formula (XXXI) wherein R$^2$ represents a TBDMS group, R$^4$ represents an isovaleryl group and R$^5$ represents a TBDMS group]:

In 20 ml of methanol was dissolved 170 mg of the compound (55) and the mixture was allowed to react at 40° C. for 2 days. The reaction mixture was concentrated under reduced pressure to obtain 160 mg of the compound (56).

Physicochemical properties of the compound (56)
(1) Color and appearance: colorless solid.
(2) Molecular formula: $C_{54}H_{99}NO_{14}SSi_2$.
(3) Mass spectrum (SIMS): m/z 1074 (M+H)$^+$.
(4) Specific rotation: $[\alpha]_D^{18}$ –21° (c 1.0, CH$_3$OH).
(5) Melting at around 72° to 75° C. without showing any definite melting point.
(6) $^1$H NMR spectrum (400 MHz, CDCl$_3$) δ (ppm: 4.04 (br dd, 3-H), 3.24 (br s, 4-H), 3.45 (s, 4-OCH$_3$), 3.49 (br d, 5-H), 2.14 (m, 6-H), 0.43 (br dd, 7-H), 1.61 (m, 8-H), 4.19 (br dd, 9-H), 5.72 (br dd, 10-H), 6.10 (m, 11-H), 6.10 (m, 12-H), 5.62 (dt, 13-H), 2.29 (m, 14-H), 4.83 (ddq, 15-H), 1.31 (d, 16-H$_3$), 1.44 (br d, 17-H), 1.67 (dt, 17-H), 4.57 (br d, 18-H), 0.93 (d, 19-H$_3$), 4.28 (d, 1'-H), 3.42 (dd, 2'-H), 3.24 (t, 4'-H), 3.24 (dq, 5'-H), 1.22 (d, 6'-H$_3$), 2.54 (s, 3'-N(CH$_3$)$_2$), 4.88 (d, 1"-H), 1.72 (dd, 2"-Hax), 2.26 (d, 2"-Heq), 1.18 (s, 3"-CH$_3$), 4.67 (d, 4"-H), 4.61 (dq, 5"-H), 1.07 (d, 6 "-H$_3$), 4.52 (d, 3"-OC$\underline{H}_2$SCH$_3$) 4.65 (d, 3"-OC$\underline{H}_2$SCH$_3$), 2.18 (s, 3"-OCH$_2$SC$\underline{H}_3$), 2.27 (dd, 4"-OCOC$\underline{H}_2$CH(CH$_3$)$_2$), 2.15 (m, 4"-OCOCH$_2$C$\underline{H}$(CH$_3$)$_2$), 0.97 (d, 4-OCOCH$_2$CH(CH$\underline{H}_3$)$_2$).

EXAMPLE 58

Process (1) for producing compound (57) [a compound represented by the formula (XXXII) wherein R$^2$ represents a TBDMS group, R$^4$ represents an isovaleryl group and R$^5$ represents a TBDMS group]:

After 160 mg of the compound (56) was dissolved in 3.4 ml of ethanol, the activity of 10 ml of Raney nickel was controlled in the same manner as in Example 7 and it was added to the above mixture together with 3.4 ml of ethanol. After the resulting mixture was stirred vigorously at room temperature for 30 minutes, insoluble matters were filtered and the filtrate was concentrated under reduced pressure. Then, 150 mg of the thus obtained residue was purified by preparative TLC [developing system: chloroform/methanl/conc. aqueous ammonia (300:10:1)] to obtain 41 mg of the compound (57).

Physicochemical properties of the compound (57)
(1) Color and appearance: colorless solid.
(2) Molecular formula: $C_{53}H_{97}NO_{14}Si_2$.
(3) Mass spectrum (SIMS): m/z 1028 (M+H)$^+$.
(4) Specific rotation: $[\alpha]_D^{16}$ –24° (c 1.0, CH$_3$OH).
(5) Melting at around 75° to 78° C. without showing any definite melting point.
(6) $^1$H NMR spectrum (400 MHz, CDCl$_3$) δ (ppm: 4.04 (br dd, 3-H), 3.44 (s, 4-OCH$_3$), 3.48 (br d, 5-H), 2.17 (m, 6-H), 0.42 (br dd, 7-H), 1.60 (m, 8-H), 4.19 (br dd, 9-H), 5.71 (br dd, 10-H), 6.10 (m, 11-H), 6.10 (m, 12-H), 5.62 (dt, 13-H), 4.82 (ddq, 15-H), 1.30 (d, 16-H$_3$), 1.42 (br d, 17-H), 1.67 (dt, 17-H), 4.57 (br d, 18-H), 4.30 (d, 1'-H), 3.39 (dd, 2'-H), 3.31 (t, 4'-H), 1.22 (d, 6'-H$_3$), 2.54 (s, 3'-N(CH$_3$)$_2$), 4.90 (d, 1"-H), 1.63 (dd, 2"-Hax), 2.27 (d, 2"-Heq), 1.09 (s, 3"-CH$_3$), 4.71 (d, 4"-H), 4.59 (dq, 5"-H), 1.07 (d, 6"-H$_3$), 3.25 (s, 3"-OCH$_3$), 2.28 (dd, 4"-OCOC$\underline{H}_2$CH(CH$_3$)$_2$).

EXAMPLE 59

Process for producing compound (58) [a compound represented by the formula (I) wherein R$^1$ represents a hydrogen atom, R$^2$ represents a hydrogen atom, R$^3$ represents a hydrogen atom and R$^4$ represents an isovaleryl group] (3"-O-methylleucomycin A$_1$):

Forty-one mg of the compound (57) was dissolved in 300 μl of a 2M TBAF/THF solution and the resulting mixture was allowed to react at 45° C. for 50 minutes. After the reaction mixture was cooled to room temperature, 1.0 ml of a 5% potassium hydrogensulfate solution was added dropwise thereto and extraction was carried out with 10 ml portions of chloroform twice. The chloroform layer was combined and successively washed with 20 ml portions of a saturated sodium hydrogencarbonate solution twice and 20 ml portions of a saturated sodium chloride solution twice. The mixture was dried over anhydrous sodium sulfate and filtered. The filtrate was concentrated under reduced pressure and the residue thus obtained was purified by preparative TLC [developing system: chloroform/methanol/conc. aqueous ammonia (400:20:1)]. Thus 9.0 mg of the compound (58) was obtained.

Physicochemical properties of the compound (58)
(1) Color and appearance: colorless solid.
(2) Molecular formula: $C_{41}H_{69}NO_{14}$.
(3) Mass spectrum (EIMS): m/z 799 (M)$^+$.
(4) Specific rotation: $[\alpha]_D^{18}$ –66° (c 0.5, CH$_3$OH).
(5) Melting at around 100° to 104° C. without showing any definite melting point.
(6) $^1$H NMR spectrum (400 MHz, CDCl$_3$) δ (ppm: 2.20 (d, 2-H), 2.69 (dd, 2-H), 3.78 (br d, 3-H), 3.08 (br d, 4-H), 3.53 (s, 4-OCH$_3$), 4.10 (br d, 5-H), 0.98 (br ddd, 7-H), 1.58 (br dt, 7-H), 1.99 (m, 8-H), 4.08 (dd, 9-H), 5.67 (dd, 10-H), 6.25 (dd, 11-H), 6.02 (br dd, 12-H), 5.59 (ddd, 13-H), 2.10 (dt, 14-H), 2.50 (br dt, 14-H), 5.28 (ddq, 15-H), 1.29 (d, 16-H$_3$), 2.32 (br d, 17-H), 2.86 (br dd, 17-H), 9.79 (br s, 18-H), 0.97 (d, 19-H$_3$), 4.57 (d, 1'-H), 3.22 (dd, 2'-H), 2.42 (t, 3'-H), 3.44 (t, 4'-H), 3.27 (dq, 5'-H), 1.18 (d, 6'-H$_3$), 2.56 (s, 3'-N(CH$_3$)$_2$), 4.92 (d, 1"-H), 1.65 (dd, 2"-Hax), 2.27 (d, 2"-Heq), 1.09 (s, 3"-CH$_3$), 4.71 (d, 4"-H), 4.53 (dq, 5"-H), 1.07 (d, 6"-H$_3$), 3.24 (s, 3"-OCH$_3$), 2.28 (dd, 4"-OCOC$\underline{H}_2$CH(CH$_3$)$_2$), 2.13 (m, 4"-OCOCH$_2$C$\underline{H}$(CH$_3$)$_2$), 0.95 (d, 4"-OCOCH$_2$CH(C$\underline{H}_3$)$_2$).

EXAMPLE 60

Process for producing compound (59) [a compound represented by the formula (VII) wherein $R^2$ represents a TBDMS group, $R^3$ represents an acetyl group, $R^4$ represents a propionyl group and $R^5$ represents a TBDMS group]:

After 1.0 g of the crude compound (42) was dissolved in a mixed solution of 30 ml of dry DMSO and 3.0 ml of acetic anhydride, the mixture was allowed to react at 45° C. for 5 days. Four hundred ml of benzene was added thereto, the resulting mixture was successively washed with 400 ml portions of purified water twice and the same volume of a saturated sodium chloride solution twice. The organic layer was dried over anhydrous sodium sulfate and filtered. The filtrate was concentrated under reduced pressure and 1.1 g of the thus obtained residue was purified by silica gel column chromatography (100 g: hexane/ethyl acetate (2:1)) to obtain 612 mg of the compound (59).

Physicochemical properties of the compound (59)
  (1) Color and appearance: colorless solid.
  (2) Molecular formula: $C_{54}H_{97}NO_{15}SSi_2$.
  (3) Mass spectrum (FDMS): m/z 1088 $(M+H)^+$.
  Specific rotation: $[\alpha]_D^{21} -28°$ (c 1.0, $CHCl_3$).
  (5) Melting at around 96° to 100° C. without showing any definite melting point.
  (6) $^1H$ NMR spectrum (400 MHz, $CDCl_3$) δ (ppm: 2.66 (dd, 2-H), 4.13 (br dd, 3-H), 2.95 (br s, 4-H), 3.41 (s, 4-$OCH_3$), 3.28 (br d, 5-H), 0.40 (br dd, 7-H), 1.51 (m, 8-H), 4.17 (br dd, 9-H), 5.94 (m, 10-H), 5.94 (m, 11-H), 6.30 (br dd, 12-H), 5.46 (ddd, 13-H), 4.64 (ddq, 15-H), 1.29 (d, 16-$H_3$), 1.44 (br d, 17-H), 1.63 (dt, 17-H), 4.52 (br d, 18-H), 0.91 (d, 19-$H_3$), 4.25 (d, 1'-H), 5.05 (dd, 2'-H), 2.75 (t, 3'-H), 3.15 (t, 4'-H), 3.26 (dq, 5'-H), 1.24 (d, 6'-$H_3$), 2.09 (s, 2'-$OCOCH_3$), 2.42 (s, 3'-$N(CH_3)_2$), 4.83 (d, 1"-H), 1.70 (dd, 2"-Hax), 1.17 (s, 3"-$CH_3$), 4.67 (d, 4"-H), 4.58 (dq, 5"-H), 1.05 (d, 6"-$H_3$), 4.52 (d, 3"-$OCH_2SCH_3$), 4.64 (d, 3"-OC$\underline{H_2}SCH_3$), 2.21 (s, 3"-$OCH_2SC\underline{H_3}$), 2.41 (dq, 4"-OCOC$\underline{H_2}CH_3$), 1.17 (t, 4"-$OCOCH_2C\underline{H_3}$).

EXAMPLE 61

Process for producing compound (60) [a compound represented by the formula (XXXI) wherein $R^2$ represents a TBDMS group, $R^4$ represents a propionyl group and $R^5$ represents a TBDMS group]:

In 60 ml of methanol was dissolved 580 mg of the compound (59) and the mixture was allowed to react at 40° C. for 2 days. The reaction mixture was concentrated under reduced pressure to obtain 550 mg of the compound (60).

Physicochemical properties of the compound (60)
  (1) Color and appearance: colorless solid.
  (2) Molecular formula: $C_{52}H_{95}NO_{14}SSi_2$.
  (3) Mass spectrum (SIMS): m/z 1046 $(M+H)^+$.
  (4) Specific rotation: $[\alpha]_D^{21} -17°$ (c 1.0, $C^1H_3OH$).
  (5) Melting at around 75° to 78° C. without showing any definite melting point.
  (6) $^1H$ NMR spectrum (400 MHz, $CDCl_3$) δ (ppm: 4.02 (br dd, 3-H), 3.23 (br s, 4-H), 3.43 (s, 4-$OCH_3$), 3.47 (br d, 5-H), 2.15 (m, 6-H), 0.41 (br dd, 7-H), 1.59 (m, 8-H), 4.18 (br dd, 9-H), 5.70 (br dd, 10-H), 6.08 (m, 11-H), 6.08 (m, 12-H), 5.60 (dt, 13-H), 2.27 (m, 14-H), 4.81 (ddq, 15-H), 1.29 (d, 16-$H_3$), 1.42 (br d, 17-H), 1.65 (dt, 17-H), 4.55 (br d, 18-H), 0.91 (d, 19-$H_3$), 4.26 (d, 1'-H), 3.41 (dd, 2'-H), 3.23 (t, 4'-H), 3.23 (dq, 5'-H), 1.20 (d, 6'-$H_3$), 2.53 (s, 3'-$N(CH_3)_2$), 4.87 (d, 1"-H), 1.70 (dd, 2"-Hax), 2.24 (d, 2"-Heq), 1.17 (s, 3"-$CH_3$), 4.65 (d, 4"-H), 4.59 (dq, 5"-H), 1.05 (d, 6"-$H_3$), 4.50 (d, 3"-OC$\underline{H_2}SCH_3$), 4.63 (d, 3"-OC$\underline{H_2}SCH_3$), 2.17 (s, 3"-$OCH_2SCH_3$), 2.40 (dq, 4"-OCOC$\underline{H_2}CH_3$), 1.16 (t, 4"-$OCOCH_2C\underline{H_3}$).

EXAMPLE 62

Process for producing compound (61) [a compound represented by the formula (XXXII) wherein $R^2$ represents a TBDMS group, $R^4$ represents a propionyl group and $R^5$ represents a TBDMS group]:

After 550 mg of the compound (60) was dissolved in 12.5 ml of ethanol, the activity of 25.0 ml of Raney nickel was controlled in the same manner as in Example 7 and it was added to the above mixture together with 12.5 ml of ethanol. After the resulting mixture was stirred vigorously at room temperature for 90 minutes, insoluble matters were filtered and the filtrate was concentrated under reduced pressure. Then, 540 mg of the thus obtained residue was purified by preparative TLC [developing system: chloroform/methanol/conc. aqueous ammonia (300:10:1)] to obtain 166 mg of the compound (61).

Physicochemical properties of the compound (61)
  (1) Color and appearance: colorless solid.
  (2) Molecular formula: $C_{51}H_{93}NO_{14}Si_2$.
  (3) Mass spectrum (SIMS): m/z 1000 $(M+H)^+$.
  (4) Specific rotation: $[\alpha]_D^{21} -4°$ (c 1.0, $CH_3OH$).
  (5) Melting at around 68° to 70° C. without showing any definite melting point.
  (6) $^1H$ NMR spectrum (400 MHz, $CDCl_3$) δ (ppm: 4.04 (br dd, 3-H), 3.44 (s, 4-$OCH_3$), 3.48 (br d, 5-H), 2.17 (m, 6-H), 0.42 (br dd, 7-H), 1.60 (m, 8-H), 4.19 (br dd, 9-H), 5.71 (br dd, 10-H), 6.10 (m, 11-H), 6.10 (m, 12-H), 5.62 (dt, 13-H), 2.30 (m, 14-H), 4.82 (ddq, 15-H), 1.30 (d, 16-$H_3$), 1.43 (br d, 17-H), 1.67 (dt, 17-H), 4.57 (br d, 18-H), 0.92 (d, 19-$H_3$), 4.30 (d, 1'-H), 3.38 (dd, 2'-H), 2.47 (t, 3'-H), 3.31 (t, 4'-H), 1.22 (d, 6'-$H_3$), 2.54 (s, 3'-$N(CH_3)_2$), 4.90 (d, 1"-H), 1.64 (dd, 2"-Hax), 2.27 (d, 2"-Heq), 1.09 (s, 3"-$CH_3$), 4.71 (d, 4"-H), 4.59 (dq, 5"-H), 1.07 (d, 6"-$H_3$), 3.26 (s, 3"-$OCH_3$), 2.42 (apparent q, 4"-OCOC$\underline{H_2}CH_3$), 2.43 (apparent q, 4"-OCOC$\underline{H_2}CH_3$). 1.16 (t, 4"-OC̄OC$H_2C\underline{H_3}$.

EXAMPLE 63

Process (2) for producing compound (2) [a compound represented by the formula (I) wherein $R^1$ represents a hydrogen atom, $R^2$ represents a hydrogen atom, $R^3$ represents a hydrogen atom and $R^4$ represents a propionyl group] (3"-O-methylleucomycin $A_7$):

To 163 mg of the compound (61) was added 1.22 ml of a 2M TBAF/THF solution and the resulting mixture was allowed to react at 45° C. for 1 hours. After the reaction mixture was cooled to room temperature, 4.0 ml of a 5% potassium hydrogensulfate solution was added dropwise thereto and extraction was carried out with 40 ml portions of chloroform twice. The chloroform layer was combined and successively washed with 80 ml portions of a saturated sodium hydrogencarbonate solution twice and 80 ml portions of a saturated sodium chloride solution twice. The mixture was dried over anhydrous sodium sulfate and filtered. The filtrate was concentrated under reduced pressure and the residue thus obtained was purified by preparative TLC [developing system: chloroform/methanol/conc. aqueous ammonia (400:20:1)]. Thus 50 mg of the compound (2) was obtained.

REFERENCE EXAMPLE 2

Process for producing compound (62) [a compound represented by the formula (XXVIII) wherein $R^2$ represents a TBDMS group, $R^3$ represents a TBDMS group, $R^4$ represents a propionyl group and $R^5$ represents a TBDMS group] (Japanese Patent Application No. Hei-5-206731):

To 1.00 g of leucomycin $A_7$ was added 12 ml of dry DMF to dissolve it and 1.18 g of TBDMSCl and 1.08 g of imidazole were added thereto followed by stirring at 50° C. for 24 hours. After the reaction mixture was cooled to room temperature, 50 ml of methanol was added thereto, the resulting mixture was stirred at room temperature for 30 minutes and then concentrated under reduced pressure. The thus obtained residue was extracted with 500 ml of benzene and the benzene layer was successively washed with 500 ml portions of a saturated sodium hydrogencarbonate solution twice and 500 ml of a saturated sodium chloride solution twice. The organic layer was dried over anhydrous sodium sulfate and filtered. The filtrate was concentrated under reduced pressure to obtain 1.22 g of the crude compound (62).

REFERENCE EXAMPLE 3

Process for producing compound (63) [a compound represented by the formula (XXIX) wherein $R^2$, $R^3$ and $R^5$ each represents a TBDMS group] (Japanese Patent Application No. Hei-5-206731):

To 1.16 g of the crude compound (62) was added 130 ml of benzene to dissolve it and 65 ml of a 25% aqueous solution of sodium hydroxide and 358 mg of tetra-n-butyl ammonium hydrogensulfate were added thereto followed by stirring at room temperature for 2 hours. The benzene layer was isolated, successively washed with 150 ml portions of a saturated sodium chloride solution twice, dried over anhydrous sodium sulfate and filtered. The filtrate was concentrated under reduced pressure and the residue thus obtained was purified by silica gel column chromatography (200 g: chloroform/methanol (30:1)) to obtain 795 mg of the compound (63).

EXAMPLE 64

Process for producing compound (64) [a compound represented by the formula (XXX) wherein $R^2$ represents a TBDMS group, $R^3$ represents a TBDMS group, $R^4$ represents an isovaleryl group and $R^5$ represents a TBDMS group]:

To 430 mg of the compound (63) was added 4.3 ml of dry pyridine to dissolve it and 248 mg of isovaleryl chloride was added thereto followed by stirring at room temperature for 10 minutes. Fifty ml of a saturated sodium hydrogencarbonate solution was added thereto and extraction was carried out with 50 ml portions of chloroform twice. The chloroform layer was washed with 50 ml portions of a saturated sodium chloride solution twice, dried over anhydrous sodium sulfate and filtered. The filtrate was concentrated under reduced pressure and dried. Then, 650 mg of the residue thus obtained was purified by preparative TLC [developing system: hexane/ethyl acetate (2:1)]. Thus 326 mg of the compound (64) was obtained.

Physicochemical properties of the compound (64)
  (1) Color and appearance: colorless solid.
  (2) Molecular formula: $C_{58}H_{109}NO_{14}Si_3$.
  (3) Mass spectrum (SIMS): m/z 1128 $(M+H)^+$.
  (4) Specific rotation: $[\alpha]_D^{14}$ –17° (c 1.0, $CH_3OH$).
  (5) Melting at around 78° to 81° C. without showing any definite melting point.
  (6) $^1H$ NMR spectrum (400 MHz, $CDCl_3$) δ (ppm: 2.38 (dd, 2-H), 2.61 (dd, 2-H), 4.22 (m, 3-H), 3.14 (br s, 4-H), 3.38 (s, 4-$OCH_3$), 3.42 (br dd, 5-H), 0.41 (br dd, 7-H), 1.70 (m, 8-H), 4.23 (m, 9-H), 5.74 (br dd, 10-H), 6.11 (m, 11-H), 6.11 (m, 12-H), 5.62 (dt, 13-H), 2.45 (m, 14-H), 4.84 (ddq, 15-H), 1.30 (d, 16-$H_3$), 1.38 (dt, 17-H), 1.65 (br d, 17-H), 4.63 (br dd, 18-H), 0.93 (d, 19-$H_3$), 4.20 (d, 1'-H), 3.53 (dd, 2'-H), 2.55 (t, 3'-H), 3.34 (t, 4'-H), 3.30 (dq, 5'-H), 1.25 (d, 6'-$H_3$), 2.53 (s, 3'-$N(CH_3)_2$), 5.10 (d, 1"-H), 1.85 (dd, 2"-Hax), 2.00 (d, 2"-Heq), 1.10 (s, 3"-$CH_3$), 4.62 (d, 4"-H), 4.37 (dq, 5"-H), 1.14 (d, 6"-$H_3$), 2.29 (d, 4"-OCO$CH_2$CH$(CH_3)_2$), 2.13 (m, 4"-OCOCH$_2$C$\underline{H}$$(CH_3)_2$), 0.97 (d, 4"-OCOCH$_2$CH$(\underline{CH_3})_2$).

EXAMPLE 65

Process for producing compound (65) [a compound represented by the formula (VII) wherein $R^2$ represents a TBDMS group, $R^3$ represents a TBDMS group, $R^4$ represents an isovaleryl group and $R^5$ represents a TBDMS group]:

After 326 mg of the compound (64) was dissolved in a mixed solution of 9.8 ml of dry DMSO and 0.98 ml of acetic anhydride, the mixture was allowed to react at 45° C. for 5 days. One hundred ml of benzene was added thereto, the resulting mixture was successively washed with 100 ml portions of purified water twice and the same volume of a saturated sodium chloride solution twice. The organic layer was dried over anhydrous sodium sulfate and filtered. The filtrate was concentrated under reduced pressure and the thus obtained residue was purified by preparative TLC (developing system: hexane/ethyl acetate (4:1)) to obtain 95 mg of the compound (65).

Physicochemical properties of the compound (65)
  (1) Color and appearance: colorless solid.
  (2) Molecular formula: $C_{60}H_{113}NO_{14}SSi_3$.
  (3) Mass spectrum (SIMS): m/z 1188 $(M+H)^+$.
  (4) Specific rotation: $[\alpha]_D^{14}$ –22° (c 1.0, $CH_3OH$).
  (5) Melting at around 90° to 92° C. without showing any definite melting point.
  (6) $^1H$ NMR spectrum (400 MHz, $CDCl_3$) δ (ppm: 2.42 (dd, 2-H), 2.60 (dd, 2-H), 4.19 (m, 3-H), 3.14 (br s, 4-H), 3.40 (s, 4-$OCH_3$), 0.38 (br dd, 7-H), 1.66 (m, 8-H), 4.21 (m, 9-H), 5.74 (dd, 10-H), 6.11 (m, 11-H), 6.11 (m, 12-H), 5.61 (dt, 13-H), 4.80 (ddq, 15-H), 1.31 (d, 16-$H_3$), 1.41 (dt, 17-H), 1.62 (br d, 17-H), 4.60 (br dd, 18-H), 0.92 (d, 19-$H_3$), 4.17 (d, 1'-H), 2.48 (t, 3'-H), 1.22 (d, 6'-$H_3$), 2.50 (s, 3'-$N(CH_3)_2$), 4.98 (d, 1"-H), 1.74 (dd, 2"-Hax), 2.25 (d, 2"-Heq), 1.20 (s, 3"-$CH_3$), 4.71 (d, 4"-H), 4.55 (dq, 5"-H), 1.08 (d, 6"-$H_3$), 4.52 (d, 3"-$OCH_2SCH_3$), 4.65 (d, 3"-OC$H_2SCH_3$), 2.18 (S, 3"-OCH$_2S\underline{CH_3}$). 2.27 (d, 4"-OCO$\underline{H_2}$CH$(CH_3)_2$), 2.13 (m, 4"-OCO$\overline{CH_2}$C$\underline{H}$$(CH_3)_2$), 0.97 (d, 4"-OCOCH$_2$CH$(\underline{CH_3})_2$)

EXAMPLE 66

Process (2) for producing compound (57) [a compound represented by the formula (XXXII) wherein $R^2$ represents a TBDMS group, $R^4$ represents an isovaleryl group and $R^5$ represents a TBDMS group]:

After 160 mg of the compound (65) was dissolved in 3.4 ml of ethanol, the activity of 10 ml of Raney nickel was controlled in the same manner as in Example 7 and it was added to the above mixture together with 3.4 ml of ethanol. After the resulting mixture was stirred vigorously at room temperature for 30 minutes, insoluble matters were filtered and the filtrate was concentrated under reduced pressure. Then, 150 mg of the thus obtained residue was dissolved in 5.7 ml of chloroform and 26 mg of m-chloroperbenzoic acid was added thereto followed by stirring at room temperature for 5 minutes. The reaction mixture was added dropwise to 30 ml of a 10% sodium thiosulfate solution and extracted with 60 ml of chloroform. The chloroform layer was washed successively with 60 ml portions of a saturated sodium hydrogencarbonate solution twice and 60 ml portions of a saturated sodium chloride solution twice, dried over anhydrous sodium sulfate and filtered. The filtrate was concentrated under reduced pressure and the residue thus obtained was charged on preparative TLC to allow it to stand for 3 days. Then, the purification was carried out by development [developing system: chloroform/methanol/conc. aqueous ammonia (300:10:1)] to obtain 41 mg of the compound (57).

REFERENCE EXAMPLE 4

Process for producing compound (66) [a compound represented by the formula (XXVII) wherein $R^2$ represents an acetyl group, $R^3$ represents an acetyl group and $R^4$ represents a propionyl group] (Pharmazie, 39(6), 414, JP-B-53-30718):

To 5.0 g of Leucomycin A7 was added 100 ml of dry pyridine to dissolve it and 2.7 g of acetic anhydride was added thereto followed by stirring at room temperature for 2 days. After 500 ml of a saturated sodium hydrogencarbonate solution was added thereto by slow degrees, the mixture was stirred at room temperature for 30 minutes and extracted with 500 ml portions of methylene chloride twice. The organic layer was washed with 500 ml portions of a saturated sodium chloride solution twice, dried over anhydrous sodium sulfate and filtered. The filtrate was concentrated under reduced pressure and the residue thus obtained was purified by silica gel column chromatography [300 g: hexane/ethyl acetate (1:3)]. Thus 3.3 g of the compound (66) was obtained.

EXAMPLE 67

Process for producing compound (67) [a compound represented by the formula (XXVIII) wherein $R^2$ represents an acetyl group, $R^3$ represents an acetyl group, $R^4$ represents a propionyl group and $R^5$ represents a TBDMS group]:

After 3.05 g of the compound (66) was dissolved in 30 ml of dry DMF and 1.10 g of TBDMSCl and 989 mg of imidazole were added thereto followed by stirring at 45° C. for 24 hours. The resulting mixture was cooled to room temperature and concentrated under reduced pressure. Three hundred ml of methylene chloride was added to the resulting residue to dissolve it and 300 ml of a saturated sodium hydrogen-carbonate solution was further added thereto followed by stirring at room temperature for 30 minutes. The organic layer was isolated, washed with 300 ml of a saturated sodium chloride solution twice, dried over anhydrous sodium sulfate and filtered. The filtrate was concentrated under reduced pressure and the thus obtained residue was purified by silica gel column chromatography (300 g: hexane/ethyl acetate (2:1)) to obtain 1.85 g of the compound (67).

Physicochemical properties of the compound (67)
  (1) Color and appearance: colorless solid.
  (2) Molecular formula: $C_{48}H_{81}NO_{16}Si$.
  (3) Mass spectrum (FDMS): m/z 955 $(M)^+$.
  (4) Specific rotation: $[\alpha]_D^{17}$ –35° (c 1.0, $CHCl_3$).
  (5) Melting at around 100° to 102° C. without showing any definite melting point.
  (6) $^1H$ NMR spectrum (400 MHz, $CDCl_3$) δ (ppm: 2.60 (dd, 2-H), 3.99 (br dd, 3-H), 3.04 (br d, 4-H), 3.40 (s, 4-$OCH_3$), 3.32 (br d, 5-H), 0.55 (br dd, 7-H), 2.18 (m, 7-H), 1.74 (m, 8-H), 5.35 (br d, 9-H), 2.14 (s, 9-$OCOCH_3$), 5.70 (dd, 10-H), 6.16 (br dd, 11-H), 6.04 (br dd, 12-H), 5.56 (dt, 13-H), 4.77 (ddq, 15-H), 1.28 (d, 16-$H_3$), 1.54 (m, 17-H), 4.54 (br d, 18-H), 0.92 (d, 19-$H_3$), 4.37 (d, 1'-H), 5.06 (dd, 2'-H), 2.74 (t, 3'-H), 3.32 (t, 4'-H), 3.32 (dq, 5'-H), 1.29 (d, 6'-$H_3$), 2.08 (s, 2'-$OCOCH_3$), 2.41 (s, 3'-$N(CH_3(_2)$), 5.08 (d, 1"-H), 1.84 (dd, 2"-Hax), 1.99 (d, 2"-Heq), 1.10 (s, 3"-$CH_3$), 4.61 (d, 4"-H), 4.41 (dq, 5"-H), 1.12 (d, 6"-$H_3$), 1.16 (t, 4"-$OCOCH_2\underline{CH_3}$).

EXAMPLE 68

Process for producing compound (68) [a compound represented by the formula (VII) wherein $R^2$ represents an acetyl group, $R^3$ represents an acetyl group, $R^4$ represents a propionyl group and $R^5$ represents a TBDMS group]:

After 1.80 g of the compound (67) was dissolved in a mixed solution of 54 ml of dry DMSO and 5.4 ml of acetic anhydride, the mixture was allowed to react at 45° C. for 3 days. Three hundred ml of benzene was added thereto, the resulting mixture was successively washed with 300 ml portions of purified water twice and the same volume of a saturated sodium chloride solution twice. The organic layer was dried over anhydrous sodium sulfate and filtered. The filtrate was concentrated under reduced pressure and the thus obtained residue was purified by silica gel column chromatography (180 g: hexane/ethyl acetate (2:1)) to obtain 440 mg of the compound (68).

Physicochemical properties of the compound (68)
  (1) Color and appearance: colorless solid.
  (2) Molecular formula: $C_{50}H_{85}NO_{16}SSi$.
  (3) Mass spectrum (FDMS): m/z 1015 $(M)^+$.
  (4) Specific rotation: $[\alpha]_D^{17}$ –44° (c 1.0, $CHCl_3$).
  (5) Melting at around 77° to 81° C. without showing any definite melting point.
  (6) $^1H$ NMR spectrum (400 MHz, $CDCl_3$) δ (ppm: 2.61 (dd, 2-H), 4.02 (br dd, 3-H), 3.04 (br d, 4-H), 3.42 (s, 4-$OCH_3$), 3.39 (br d, 5-H), 0.55 (br dd, 7-H), 1.74 (m, 8-H), 5.35 (br d, 9-H), 2.13 (s, 9-$OCOCH_3$), 5.72 (dd, 10-H), 6.18 (dd, 11-H), 6.03 (br dd, 12-H), 5.56 (dt, 13-H), 4.75 (ddq, 15-H), 1.28 (d, 16-$H_3$), 4.55 (br d, 18-H), 0.91 (d, 19-$H_3$), 4.35 (d, 1'-H), 5.02 (dd, 2'-H), 2.75 (t, 3'-H), 3.20 (t, 4'-H), 3.27 (dq, 5'-H), 1.25 (d, 6'-$H_3$), 2.07 (s, 2'-$OCOCH_3$), 2.42 (s, 3'-$N(CH_3(_2)$), 4.84 (d, 1"-H), 1.69 (dd, 2"-Hax), 2.24 (d, 2"-Heq), 1.16 (s, 3"-$CH_3$), 4.67 (d, 4"-H), 4.59 (dq, 5"-H), 1.04 (d, 6"-$H_3$), 4.52 (d, 3"-$OCH_2SCH_3$), 4.63 (d, 3"-O$H_2SCH_3$), 2.20 (s, 3"-$OCH_2S\underline{CH_3}$), 1.16 (t, 4"-$OCOCH_2C\underline{H_3}$).

EXAMPLE 69

Process for producing compound (69) [a compound represented by the formula (XXXI) wherein $R^2$ represents an acetyl group, $R^4$ represents a propionyl group and $R^5$ represents a TBDMS group]:

In 42 ml of methanol was dissolved 420 mg of the compound (68) and the mixture was allowed to react at 40° C. for 2 days. The reaction mixture was concentrated under reduced pressure to obtain 400 mg of the compound (69).

Physicochemical properties of the compound (69)
  (1) Color and appearance: colorless solid.
  (2) Molecular formula: $C_{48}H_{83}NO_{15}SSi$.
  (3) Mass spectrum (FDMS): m/z 973 $(M)^+$.
  (4) Specific rotation: $[\alpha]_D^{17}$ –21° (c 1.0, $CH_3OH$).
  (5) Melting at around 75° to 78° C. without showing any definite melting point.
  (6) $^1H$ NMR spectrum (400 MHz, $CDCl_3$) δ (ppm: 2.67 (dd, 2-H), 3.99 (br dd, 3-H), 3.28 (br d, 4-H), 3.47 (s, 4-$OCH_3$), 3.59 (br d, 5-H), 0.67 (br dd, 7-H), 1.86 (m, 8-H), 5.40 (br d, 9-H), 2.13 (s, 9-$OCOCH_3$), 5.61 (dd, 10-H), 6.06 (m, 11-H), 6.06 (m, 12-H), 5.67 (dt, 13-H), 4.87 (ddq, 15-H), 1.29 (d, 16-$H_3$), 1.40 (br dt, 17-H), 1.79 (br dd, 17-H), 4.58

(br d, 18-H), 0.93 (d, 19-H$_3$), 4.32 (d, 1'-H), 3.39 (dd, 2'-H), 2.48 (t, 3'-H), 3.37 (t, 4'-H), 3.27 (dq, 5'-H), 1.23 (d, 6'-H$_3$), 2.55 (s, 3'-N(CH$_3$($_2$), 4.91 (d, 1"-H), 1.72 (dd, 2"-Hax), 2.26 (d, 2"-Heq), 1.18 (s, 3"-CH$_3$), 4.66 (d, 4"-H), 4.59 (dq, 5"-H), 1.06 (d, 6"-H$_3$), 4.51 (d, 3"-OCH$_2$SCH$_3$), 4.64 (d, 3"-OCH$_2$SCH$_3$), 2.17 (s, 3"-OCH$_2$S$\underline{C}$H$_3$), 1.17 (t, 4"-OCOCH$_2$C$\underline{H}_3$).

EXAMPLE 70

Process for producing compound (70) [a compound represented by the formula (XXXII) wherein R$^2$ represents an acetyl group, R$^4$ represents a propionyl group and R$^5$ represents a TBDMS group]:

After 400 mg of the compound (69) was dissolved in 10 ml of ethanol, the activity of 10 ml of Raney nickel was controlled in the same manner as in Example 7 and it was added to the above mixture together with 10 ml of ethanol. After the resulting mixture was stirred vigorously at room temperature for 45 minutes, insoluble matters were filtered and the filtrate was concentrated under reduced pressure. Then, 360 mg of the thus obtained residue was purified by preparative TLC [developing system: chloroform/methanol/ conc. aqueous ammonia (300:10:1)] to obtain 150 mg of the compound (70).

Physicochemical properties of the compound (70)
  (1) Color and appearance: colorless solid.
  (2) Molecular formula: C$_{47}$H$_{81}$NO$_{15}$Si.
  (3) Mass spectrum (FDMS): m/z 927 (M)$^+$.
  (4) Specific rotation: [α]$_D^{17}$–14° (c 1.0, CH$_3$OH).
  (5) Melting at around 80° to 83° C. without showing any definite melting point.
  (6) $^1$H NMR spectrum (400 MHz, CDCl$_3$) (ppm): 2.66 (dd, 2-H), 4.00 (br dd, 3-H), 3.28 (br d, 4-H), 3.47 (s, 4-OCH$_3$), 3.58 (br d, 5-H), 0.67 (br dd, 7-H), 1.85 (m, 8-H), 5.39 (br d, 9-H), 2.12 (s, 9-OCOCH$_3$), 5.61 (dd, 10-H), 6.06 (m, 11-H), 6.06 (m, 12-H), 5.67 (dt, 13-H), 4.86 (ddq, 15-H), 1.29 (d, 16-H$_3$), 1.39 (br dt, 17-H), 1.78 (br dd, 17-H), 4.58 (br d, 18-H), 0.92 (d, 19-H$_3$), 4.35 (d, 1'-H), 3.35 (dd, 2'-H), 3.42 (t, 4'-H), 1.24 (d, 6'-H$_3$), 2.55 (s, 3'-N(CH$_3$($_2$), 4.92 (d, 1"-H), 1.64 (dd, 2"-Hax), 2.27 (d, 2"-Heq), 1.08 (s, 3"-CH$_3$), 4.70 (d, 4"-H), 4.60 (dq, 5"-H), 1.05 (d, 6"-H$_3$), 3.25 (s, 3"-OCH$_3$), 2.41 (apparent q, 4"-OCOC$\underline{H}_2$CH$_3$), 2.42 (apparent q, 4"-OCOC$\underline{H}_2$CH$_3$), 1.15 (t, 4"-OCOCH$_2$C$\underline{H}_3$).

EXAMPLE 71

Process (2) for producing compound (6) [a compound represented by the formula (I) wherein R$^1$ represents a hydrogen atom, R$^2$ represents an acetyl group, R$^3$ represents a hydrogen atom and R$^4$ represents a propionyl group] (9-O-acetyl-3"-O-methylleucomycin A$_7$):

To 127 mg of the compound (70) was added 685 μl of a 2M TBAF/THF solution and the resulting mixture was allowed to react at 45° C. for 35 minutes. After the reaction mixture was cooled to room temperature, 3.0 ml of a 5% potassium hydrogensulfate solution was added dropwise thereto and extraction was carried out with 30 ml portions of chloroform twice. The chloroform layer was combined and successively washed with 50 ml portions of a saturated sodium hydrogencarbonate solution twice and 50 ml portions of a saturated sodium chloride solution twice. The mixture was dried over anhydrous sodium sulfate and filtered. The filtrate was concentrated under reduced pressure and the residue thus obtained was purified by preparative TLC [developing system: chloroform/methanol/conc. aqueous ammonia (400:20 1)]. Thus 68 mg of the compound (6) was obtained.

EXAMPLE 72

Process for producing compound (71) [a compound represented by the formula (I) wherein R$^1$ represents a hydrogen atom, R$^2$ represents a propionyl group, R$^3$ represents a hydrogen atom and R$^4$ represents a propionyl group] (3"-O-methyl-9-O-propionylleucomycin A$_7$):

To 15 mg of the compound (2) was added 1.3 ml of toluene to dissolve it and 14 μl of dry pyridine and 14 μl of propionyl chloride were added thereto followed by stirring at room temperature for 1 hour. Twenty ml of a saturated sodium hydrogencarbonate solution was added thereto and extraction was carried out with 20 ml portions of chloroform twice. The chloroform layer was washed with 40 ml portions of a saturated sodium chloride solution twice, dried over anhydrous sodium sulfate and filtered. The filtrate was concentrated under reduced pressure and the residue thus obtained was purified by preparative TLC [developing system: chloroform/methanol/conc. aqueous ammonia (400:20:1)]. Thus 15 mg of the compound (71) was obtained.

Physicochemical properties of the compound (71)
  (1) Color and appearance: colorless solid.
  (2) Molecular formula: C$_{42}$H$_{69}$NO$_{15}$.
  (3) Mass spectrum (EIMS): m/z 827 (M)$^+$.
  (4) Specific rotation: [α]$_D^{18}$–50° (c 1.0, CH$_3$OH).
  (5) Melting at around 128° to 132° C. without showing any definite melting point.
  (6) $^1$H NMR spectrum (400 MHz, CDCl$_3$) δ (ppm: 2.20 (d, 2-H), 2.69 (dd, 2-H), 3.77 (br d, 3-H), 3.07 (br d, 4-H), 3.52 (s, 4-OCH$_3$), 4.12 (br d, 5-H), 0.96 (br ddd, 7-H), 1.61 (br dt, 7-H), 1.98 (m, 8-H), 5.16 (dd, 9-H), 2.26 (q, 9-OCOC$\underline{H}_2$CH$_3$), 1.09 (t, 9-OCOCH$_2$C$\underline{H}_3$), 5.59 (dd, 10-H), 6.38 (dd, 11-H), 6.02 (br dd, 12-H), 5.63 (ddd, 13-H), 2.11 (dt, 14-H), 2.49 (br dt, 14-H), 5.27 (ddq, 15-H), 1.29 (d, 16-H$_3$), 2.81 (br dd, 17-H), 9.78 (br s, 18-H), 0.96 (d, 19-H$_3$), 4.55 (d, 1'-H), 3.19 (dd, 2'-H), 3.43 (t, 4'-H), 3.26 (dq, 5'-H), 1.18 (d, 6'-H$_3$), 2.56 (s, 3'-N(CH$_3$($_2$), 4.92 (d, 1"-H), 1.65 (dd, 2"-Hax), 2.28 (d, 2"-Heq), 1.09 (s, 3"-CH$_3$), 4.70 (d, 4"-H), 4.52 (dq, 5"-H), 1.06 (d, 6"-H$_3$), 3.24 (s, 3"-OCH$_3$), 2.41 (apparent q, 4"-OCOC$\underline{H}_2$CH$_3$), 2.42 (apparent q, 4"-OCOC$\underline{H}_2$CH$_3$), 1.16 (t, 4"-OCOCH$_2$C$\underline{H}_3$).

While the invention has been described in detail and with reference to specific embodiments thereof, it will be apparent to one skilled in the art that various changes and modification can be made therein without departing from the spirit and scope thereof.

What is claimed is:

1. A compound represented by the formula (I):

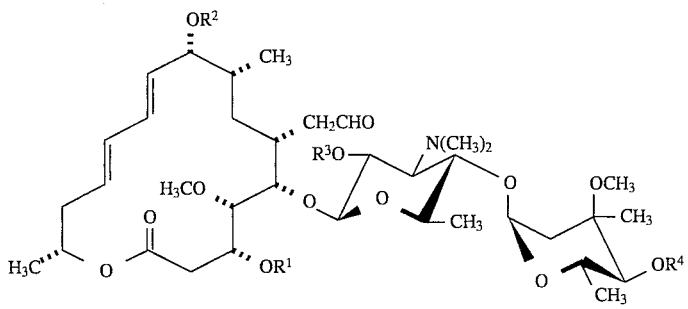

(I)

wherein $R^1$ represents a hydrogen atom or a substituent group which protects a hydroxyl group; $R^2$ represents a hydrogen atom or a substituent group which protects a hydroxyl group; $R^3$ represents a hydrogen atom or a straight-chain aliphatic acyl group having 2 to 4 carbon atoms; and $R^4$ represents a hydrogen atom or a straight-chain aliphatic or aromatic acyl group having up to 10 carbon atoms; or a pharmaceutically acceptable salt thereof.

2. The compound as claimed in claim 1, wherein the substituent group which protects a hydroxyl group is an aliphatic acyl group having 2 to 4 carbon atoms.

3. The compound as claimed in claim 1, wherein $R^3$ represents a hydrogen atom or a straight-chain aliphatic acyl group having 2 to 3 carbon atoms.

4. The compound as claimed in claim 1, wherein $R^4$ represents a hydrogen atom or a straight-chain aliphatic or aromatic acyl group having up to 7 carbon atoms.

5. The compound as claimed in claim 1, wherein $R^1$ is a hydrogen atom, an acetyl group, a propionyl group or a 1-ethoxyethyl group, $R^2$ is a hydrogen atom, an acetyl group, a propionyl group, a butyryl group or a 1-ethoxyethyl group, $R^3$ is a hydrogen atom, an acetyl group or a propionyl group and $R^4$ is a hydrogen atom, an acetyl group, a propionyl group, a normal butyryl group, an isobutyryl group, a normal valeryl group, an isovaleryl group or a benzoyl group, or a pharmaceutically acceptable salt thereof.

6. The compound as claimed in claim 1, wherein $R^1$ is a propionyl group, $R^2$ is a hydrogen atom, $R^3$ is a hydrogen atom and $R^4$ is a propionyl group or a pharmaceutically acceptable salt thereof.

7. The compound as claimed in claim 1, wherein $R^1$ is a hydrogen atom, $R^2$ is a hydrogen atom, $R^3$ is a hydrogen atom and $R^4$ is a propionyl group or a pharmaceutically acceptable salt thereof.

8. The compound as claimed in claim 1, wherein $R^1$ is a propionyl group, $R^2$ is a hydrogen atom, $R^3$ is a hydrogen atom and $R^4$ is a hydrogen atom or a pharmaceutically acceptable salt thereof.

9. The compound as claimed in claim 1, wherein $R^1$ is a hydrogen atom, $R^2$ is a hydrogen atom, $R^3$ is a hydrogen atom and $R^4$ is a hydrogen atom or a pharmaceutically acceptable salt thereof.

10. The compound as claimed in claim 1, wherein $R^1$ is a propionyl group, $R^2$ is an acetyl group, $R^3$ is a hydrogen atom and $R^4$ is a propionyl group or a pharmaceutically acceptable salt thereof.

11. The compound as claimed in claim 1, wherein $R^1$ is a hydrogen atom, $R^2$ is an acetyl group, $R^3$ is a hydrogen atom, $R^4$ is a propionyl group or a pharmaceutically acceptable salt thereof.

12. The compound as claimed in claim 1, wherein $R^1$ is an acetyl group, $R^2$ is an acetyl group, $R^3$ is a hydrogen atom, $R^4$ is an isovaleryl group or a pharmaceutically acceptable salt thereof.

13. The compound as claimed in claim 1, wherein $R^1$ is a propionyl group, $R^2$ is a 1-ethoxyethyl group, $R^3$ is a hydrogen atom and $R^4$ is a propionyl group or a pharmaceutically acceptable salt thereof.

14. The compound as claimed in claim 1, wherein $R^1$ is an acetyl group, $R^2$ is a 1-ethoxyethyl group, $R^3$ is a hydrogen atom and $R^4$ is an isovaleryl group or a pharmaceutically acceptable salt thereof.

15. The compound as claimed in claim 1, wherein $R^1$ is an acetyl group, $R^2$ is a hydrogen atom, $R^3$ is a hydrogen atom and $R^4$ is an isovaleryl group or a pharmaceutically acceptable salt thereof.

16. The compound as claimed in claim 1, wherein $R^1$ is an acetyl group, $R^2$ is a propionyl group, $R^3$ is a hydrogen atom and $R^4$ is an isovaleryl group or a pharmaceutically acceptable salt thereof.

17. The compound as claimed in claim 1, wherein $R^1$ is a propionyl group, $R^2$ is a propionyl group, $R^3$ is a hydrogen atom, $R^4$ is a propionyl group or a pharmaceutically acceptable salt thereof.

18. The compound as claimed in claim 1, wherein $R^1$ is a hydrogen atom, $R^2$ is a hydrogen atom, $R^3$ is a hydrogen atom and $R^4$ is a normal butyryl group or a pharmaceutically acceptable salt thereof.

19. The compound as claimed in claim 1, wherein $R^1$ is a hydrogen atom, $R^2$ is an acetyl group, $R^3$ is a hydrogen atom and $R^4$ is a normal butyryl group or a pharmaceutically acceptable salt thereof.

20. The compound as claimed in claim 1, wherein $R^1$ is a hydrogen atom, $R^2$ is a propionyl group, $R^3$ is a hydrogen atom and $R^4$ is a normal butyryl group or a pharmaceutically acceptable salt thereof.

21. The compound as claimed in claim 1, wherein $R^1$ is a 1-ethyoxyethyl group, $R^2$ is an acetyl group, $R^3$ is a hydrogen atom and $R^4$ is a normal butyryl group, or an isomer thereof, or a pharmaceutically acceptable salt thereof.

22. The compound as claimed in claim 1, wherein $R^1$ is a hydrogen atom, $R^2$ is a hydrogen atom, $R^3$ is a hydrogen atom and $R^4$ is a normal valeryl group or a pharmaceutically acceptable salt thereof.

23. The compound as claimed in claim 1, wherein $R^1$ is a hydrogen atom, $R^2$ is a hydrogen atom, $R^3$ is a hydrogen atom and $R^4$ is an isobutyryl group or a pharmaceutically acceptable salt thereof.

24. The compound as claimed in claim 1, wherein $R^1$ is a hydrogen atom, $R^2$ is a hydrogen atom, $R^3$ is a hydrogen atom and $R^4$ is an isovaleryl group or a pharmaceutically acceptable salt thereof.

25. The compound as claimed in claim 1, wherein $R^1$ is a hydrogen atom, $R^2$ is a propionyl group, $R^3$ is a hydrogen atom, $R^4$ is a propionyl group or a pharmaceutically acceptable salt thereof.

26. A antimicrobial composition comprising a compound represented by the formula (I):

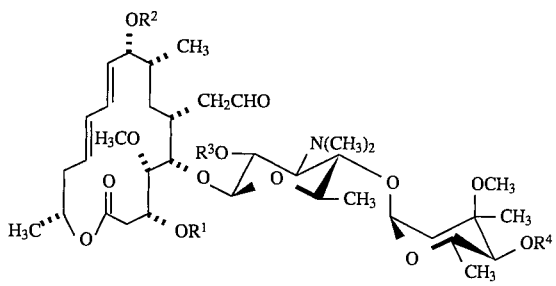

wherein $R^1$ represents a hydrogen atom or a substituent group which protects a hydroxyl group; $R^2$ represents a hydrogen atom or a substituent group which protects a hydroxyl group; $R^3$ represents a hydrogen atom or a straight-chain aliphatic acyl group having 2 to 4 carbon atoms; and $R^4$ represents a hydrogen atom or a straight-chain aliphatic or aromatic acyl group having up to 10 carbon atoms;

or a pharmaceutically acceptable salt thereof in combination with a pharmaceutically acceptable carrier.

* * * * *